(12) United States Patent
Eddington et al.

(10) Patent No.: US 11,366,103 B2
(45) Date of Patent: Jun. 21, 2022

(54) MULTI-WELL MICROPATTERNING BY ABLATION

(71) Applicant: Massachusetts Institute of Technology, Cambridge, MA (US)

(72) Inventors: David T. Eddington, Wheaton, IL (US); Sangeeta N. Bhatia, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 41 days.

(21) Appl. No.: 16/741,423

(22) Filed: Jan. 13, 2020

(65) Prior Publication Data
US 2020/0256852 A1    Aug. 13, 2020

Related U.S. Application Data

(60) Division of application No. 15/291,857, filed on Oct. 12, 2016, now Pat. No. 10,571,461, which is a
(Continued)

(51) Int. Cl.
*B01L 3/00*    (2006.01)
*C12M 3/00*    (2006.01)
(Continued)

(52) U.S. Cl.
CPC ...... *G01N 33/5067* (2013.01); *B01J 19/0046* (2013.01); *B01L 3/5025* (2013.01);
(Continued)

(58) Field of Classification Search
CPC ..... C12M 23/12; C12M 23/20; B01L 3/5025; G01N 33/5008; G01N 33/5067
See application file for complete search history.

(56) References Cited

U.S. PATENT DOCUMENTS

| 4,591,570 A | 5/1986 | Chang |
| 5,391,463 A | 2/1995 | Ligler et al. |

(Continued)

FOREIGN PATENT DOCUMENTS

| EP | 1188481 A2 | 3/2002 |
| EP | 1364702 A2 | 11/2003 |
| WO | 2006112709 A2 | 10/2006 |

OTHER PUBLICATIONS

Bhatia, S. N. et al. Faseb J 1999,13,1883-1900.
(Continued)

*Primary Examiner* — Nathan A Bowers
(74) *Attorney, Agent, or Firm* — McCarter & English, LLP

(57) ABSTRACT

The present invention is drawn to the generation of micropatterns of biomolecules and cells on standard laboratory materials through selective ablation of a physisorbed biomolecule with oxygen plasma. In certain embodiments, oxygen plasma is able to ablate selectively physisorbed layers of biomolecules (e.g., type-I collagen, fibronectin, laminin, and Matrigel) along complex non-linear paths which are difficult or impossible to pattern using alternative methods. In addition, certain embodiments of the present invention relate to the micropatterning of multiple cell types on curved surfaces, multiwell plates, and flat bottom flasks. The invention also features kits for use with the subject methods.

23 Claims, 40 Drawing Sheets

Related U.S. Application Data continuation of application No. 14/226,599, filed on Mar. 26, 2014, now abandoned, which is a continuation of application No. 11/974,341, filed on Oct. 12, 2007, now abandoned.

(60) Provisional application No. 60/851,101, filed on Oct. 12, 2006.

(51) Int. Cl.

| | |
|---|---|
| *G01N 33/50* | (2006.01) |
| *C12M 1/32* | (2006.01) |
| *C12M 1/00* | (2006.01) |
| *C12M 1/12* | (2006.01) |
| *G01N 33/543* | (2006.01) |
| *B01J 19/00* | (2006.01) |
| *C12N 5/071* | (2010.01) |

(52) U.S. Cl.
CPC ............ *C12M 23/12* (2013.01); *C12M 23/20* (2013.01); *C12M 25/04* (2013.01); *C12N 5/0671* (2013.01); *G01N 33/5008* (2013.01); *G01N 33/5436* (2013.01); *G01N 33/54353* (2013.01); *B01J 2219/00317* (2013.01); *B01J 2219/00587* (2013.01); *B01J 2219/0898* (2013.01); *B01L 2200/0647* (2013.01); *B01L 2200/12* (2013.01); *B01L 2300/0636* (2013.01); *C12N 2502/14* (2013.01); *C12N 2535/10* (2013.01)

(56) References Cited

U.S. PATENT DOCUMENTS

| | | | | |
|---|---|---|---|---|
| 6,699,665 | B1* | 3/2004 | Kim | B01L 3/5025 435/288.4 |
| 7,579,179 | B2 | 8/2009 | Bryhan et al. | |
| 10,571,461 | B2 | 2/2020 | Eddington et al. | |
| 2001/0023073 | A1 | 9/2001 | Bhatia et al. | |
| 2002/0182633 | A1 | 12/2002 | Chen et al. | |
| 2003/0073228 | A1 | 4/2003 | Duffy et al. | |
| 2005/0158880 | A1 | 7/2005 | Ostuni et al. | |
| 2006/0160066 | A1 | 7/2006 | Bhatia et al. | |
| 2006/0237080 | A1* | 10/2006 | Jon | B01L 3/502707 137/883 |
| 2008/0220516 | A1 | 9/2008 | Eddington et al. | |
| 2015/0065389 | A1 | 3/2015 | Eddington et al. | |

OTHER PUBLICATIONS

Bhatia, S. N. et al. J Biomed Mater Res 1997, 34,189-199.
Bhatia, S., et al., Methods in Molecular Medicine, 18:349-363 (1999).
Chen et al. Science 1997, 276, 1425-1428.
Chiu et al. Proceedings of the National Academy of Science 2000, 97, 2408-2413.
Duffy, D., et al., Analytical Chemistry 1998, 70, 4974.
Flaim et al. Nature Methods 2005, 2, 119-125.
Flounders, et al., Biosens Bioelectron. 1997; 12(6):447-56.
Folch et al. Journal of Biomedical Materials Research 2000, 52, 346-353.
Galbraith et al. Current Opinion in Cell Biology 1998, 10,566-571.
Gurdak, E.; et al., Langmuir 2005, 21, 10684-10692.
Hamaguchi et al. Experimental Biology and Medicine 2003,228,1227-1233.
Kan et al. Asaio J 1998,44, M441-444.
Khademhosseini et al. PNAS 2006,103,2480-2487.
Montesano et al. Journal of Cell Biology 1983, 97, 935-939.
Mooney et al. J Cell Physiol 1992, 151,497-505.
Nelson et al. Febs Letters 2002,514,238-242.
Pardo et al. American Chemical Society 2003,19,1462-1466.
Reid et al. Hepatology 1992,15,1198-1203.
Schwartz et al. Nature Cell Biology 2002, 4, E65-E68.
Seglen, Methods Cell Biol, 1976, 13, 29-83.
Singhvi et al. Science 1994, 264, 696-698.
Tan et al. Proceedings of the National Academy of Sciences of the United States of America 2003,100,1484-1489.
Wang, De-Yao et al., J. Biomed. Mater. Res. Part B: Appl. Biomater., vol. 80B:447-453 (2007).
U.S. Appl. No. 11/974,341, filed Oct. 12, 2007, David T. Eddington.
U.S. Appl. No. 14/226,599, filed Mar. 26, 2014, David T. Eddington.
U.S. Appl. No. 15/291,857, filed Oct. 12, 2016, David T. Eddington.
U.S. Appl. No. 11/974,341, Feb. 25, 2013, N. Bowers.
U.S. Appl. No. 11/974,341, Jun. 14, 2012, N. Bowers.
U.S. Appl. No. 11/974,341, Dec. 16, 2010, N. Bowers.
U.S. Appl. No. 11/974,341, Apr. 29, 2010, N. Bowers.
U.S. Appl. No. 14/226,599, Apr. 12, 2016, N. Bowers.
U.S. Appl. No. 14/226,599, Sep. 24, 2015, N. Bowers.
U.S. Appl. No. 15/291,857, Oct. 9, 2019, N. Bowers.
U.S. Appl. No. 15/291,857, Mar. 26, 2019, N. Bowers.
U.S. Appl. No. 15/291,857, Sep. 13, 2018, N. Bowers.
U.S. Appl. No. 15/291,857, Apr. 2, 2018, N. Bowers.

\* cited by examiner

Fig. 1A
PDMS Etch Mask
Fig. 1B
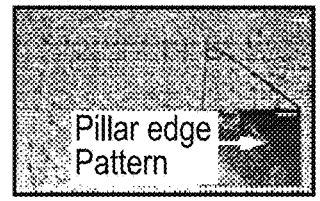
Fig. 1C
Insert etch mask into multiwell plate and compress etch mask onto plate surface
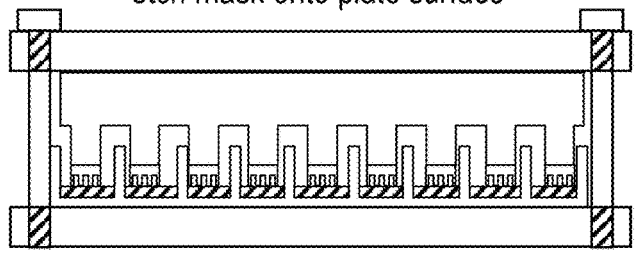
Fig. 1D
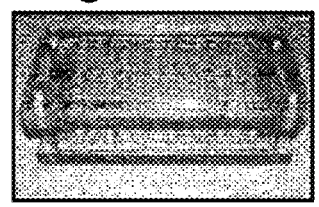
Fig. 1E
Etch unmasked protein with oxygen plasma
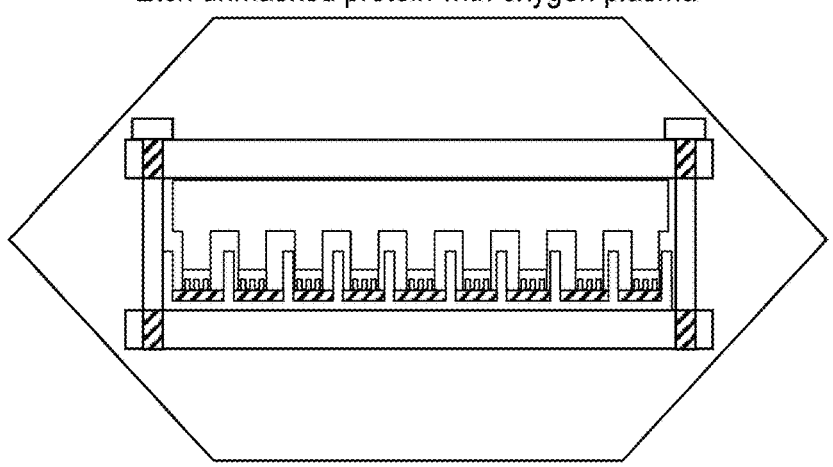
Fig. 1F
Remove etch mask
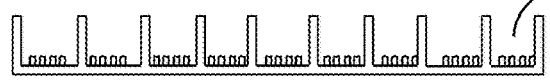
Fig. 1G
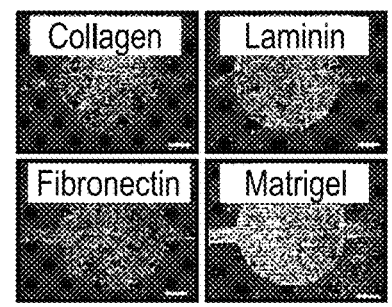

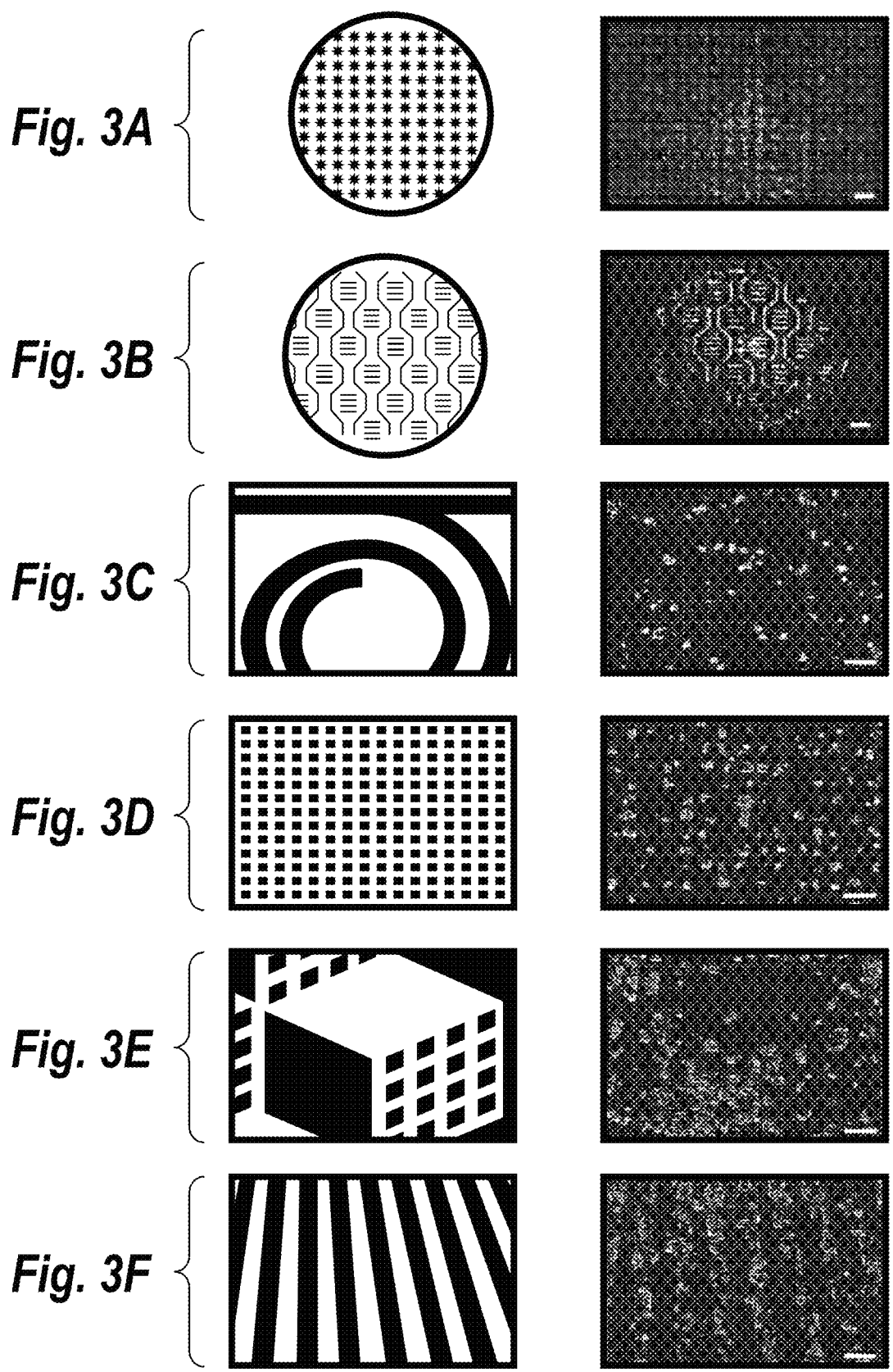

*Fig. 8B*
 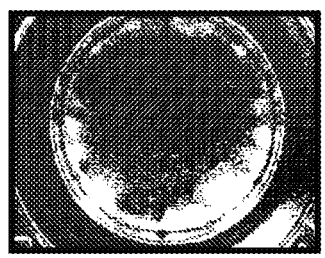 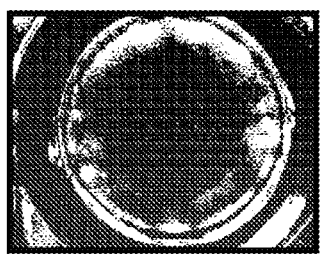
  
[A]　　　　　　　[B]　　　　　　　[C]
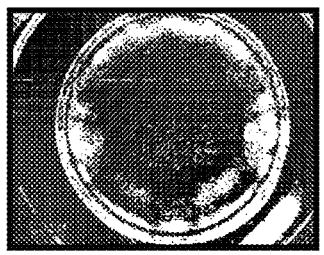 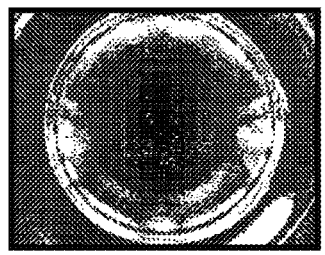 
  
[D]　　　　　　　[E]　　　　　　　[F]

Pure Hepatocytes (Day 1)    Pure Hepatocytes (Week 1)    Micropatterned Co-culture (Week 1)

*Fig. 19A*
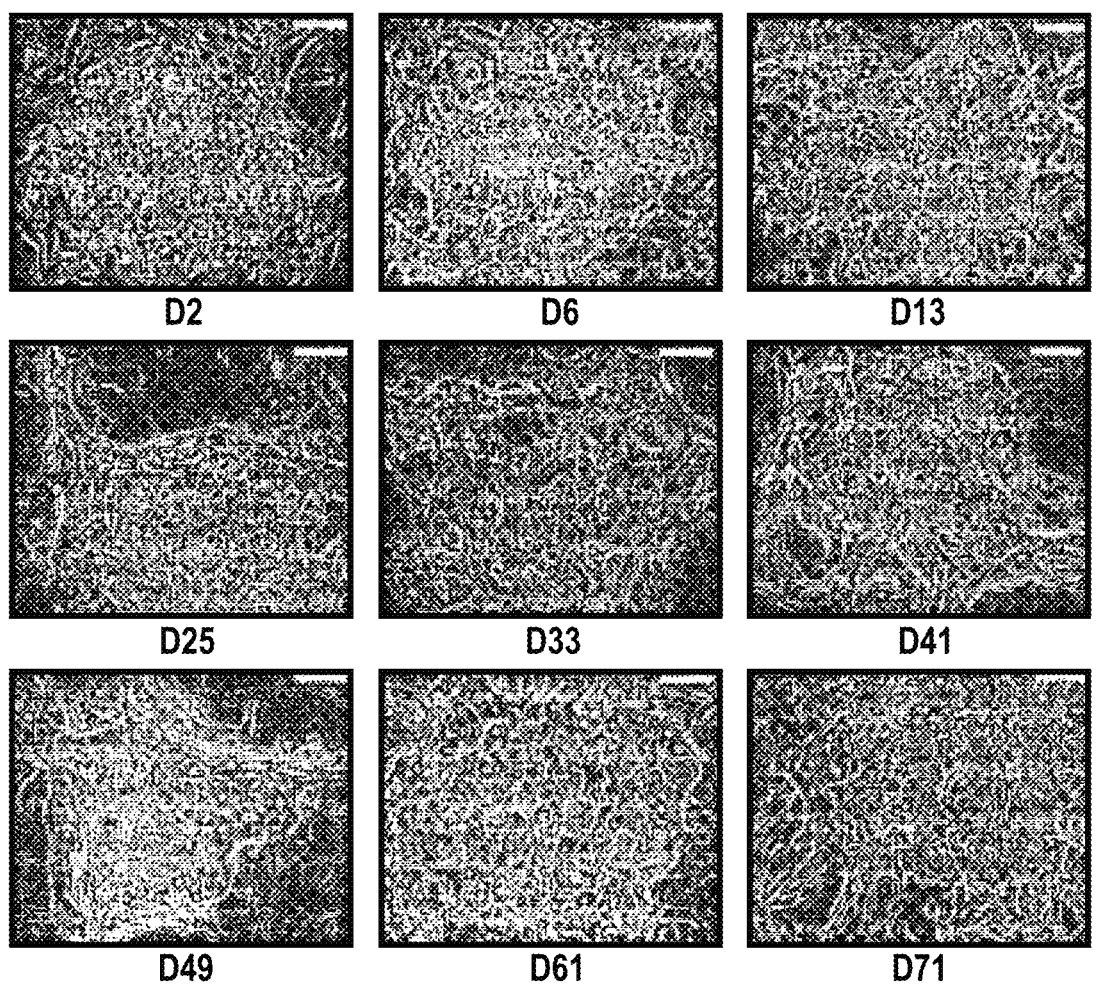
*Fig. 19B*
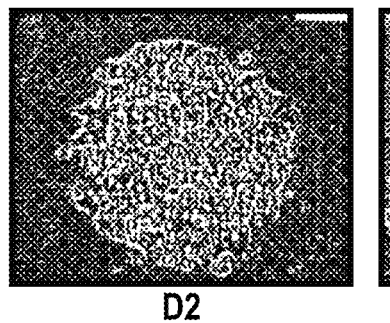
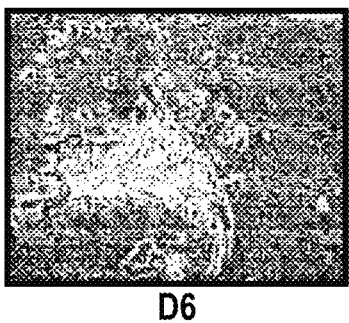
*Fig. 19C*
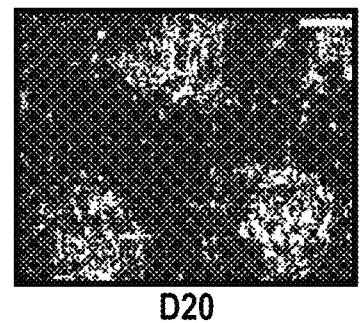

MULTI-WELL MICROPATTERNING BY ABLATION

CROSS-REFERENCE

This application is a divisional application of U.S. application Ser. No. 15/291,857, filed on Oct. 12, 2016, now pending, which application is a continuation of U.S. application Ser. No. 14/226,599, filed on Mar. 26, 2014, now abandoned, which is a continuation of U.S. application Ser. No. 11/974,341, filed on Oct. 12, 2007, now abandoned, which claims the benefit of U.S. Provisional Application No. 60/851,101, filed Oct. 12, 2006. The contents of the aforementioned applications are hereby incorporated by reference.

BACKGROUND OF THE INVENTION

The growth and function of anchorage dependent cells is closely tied to local microenvironmental cues surrounding the cell including the nature of the underlying substrate, the degree of cell-cell contact (both homotypic and heterotypic), paracrine signaling, and physical forces. Mooney, D.; Hansen, L.; Vacanti, J.; Langer, R; Farmer, S.; Ingber, D. *J Cell Physiol* 1992, 151, 497-505; Reid, L. M.; Fiorino, A. S.; Sigal, S. H.; Brill, S.; Holst, P. A. *Hepatology* 1992, 15, 1198-1203; Nelson, C. M.; Chen, C. S. *Febs Letters* 2002, 514, 238-242; Bhatia, S, N.; Balis, U. J.; Yarmush, M. L.; Toner, M. *Faseb J* 1999, 13, 1883-1900; Tan, J. L.; Tien, J.; Pirone, D. M.; Gray, D. S.; Bhadriraju, K.; Chen, C. S. *Proceedings of the National Academy of Sciences of the United States of America* 2003, 100, 1484-1489; Galbraith, C. G.; Sheetz, M. P. *Current Opinion in Cell Biology* 1998, 10, 566-571. Cell adhesion to culture materials can be modulated through adsorption of extra cellular matrix (ECM) components which interact with the cell through various integrin signaling pathways. Chen, C. S.; Mrksich, M.; Huang, S.; Whitesides, G. M.; Ingber, D. E. *Science* 1997, 276, 1425-1428; Flaim, C. J.; Chien, S.; Bhatia S. N. *Nature Methods* 2005, 2, 119-125. In addition, the degree of cell-cell interaction can influence their fate and function through both contact-mediated and soluble signals from neighboring cells. Schwartz, M. A.; Ginsberg, M. H. *Nature Cell Biology* 2002, 4, E65-E68. Traditional tools to address this microenvironmental parameter space are limited to bulk manipulations of the culture conditions. Kan, P.; Miyoshi, H.; Yanagi, K; Ohshima, N. *Asaio J* 1998, 44, M441-444. Adsorbing biomolecules such as ECM components to the substrate can modulate cell-matrix interactions. Cell-cell interactions are probed through seeding densities (higher densities increase homotypic interactions and lower densities reduce homotypic interactions), or co-cultivation with other cell types at various ratios to alter the homotypic and heterotypic interface. Hamaguchi, K.; Utsunomiya, N.; Takaki, R.; Yoshimatsu, H.; Sakata, T. *Experimental Biology and Medicine* 2003, 228, 1227-1233. While these techniques have yielded valuable experimental data and insight, engineering microenvironmental cues through micropatterning in high throughput biological formats enables precise experimentation not currently available using traditional techniques. Montesano, R; Mouron, P.; Amherdt, M.; Orci, L. *Journal of Cell Biology* 1983, 97, 935-939.

Recently, various methods to control cell-matrix and cell-cell interactions through protein and cellular micropatterning have been demonstrated. Khademhosseini, A.; Langer, R.; Borenstein, J.; Vacanti, J. P. PNAS 2006, 103, 2480-2487. Some examples include microcontact printing, microfluidic patterning, photolithographic patterning, stencil patterning, and ink-jet printing. Singhvi, R.; Kumar, A.; Lopez, G. P.; Stephanopoulos, G. N.; Wang, D. I. C.; Whitesides, G. M.; Ingber, D. E. *Science* 1994, 264, 696-698; Chiu D. T.; Jeon, N. L.; Huang, S.; Kane, R. S.; Wargo, C. J.; Choi, I. S.; Ingber, D. E.; Whitesides, G. M. *Proceedings of the National Academy of Science* 2000, 97, 2408-2413; Bhatia, S. N.; Yarmush, M. L.; Toner, M. *J Biomed Mater Res* 1997, 34, 189-199; Folch, A; Jo, B. H.; Hurtado, 0.; Beebe, D. J.; Toner, M. *Journal of Biomedical Materials Research* 2000, 52, 346-353; Pardo, L.; Wilson, W. C.; Boland, T. Langmuir 2003, 19, 1462-1466. However, these techniques often require specific substrates (gold for microcontact printing or ink jet printing), are limited to simple geometries (microfluidic and stencil patterning) and flat surfaces (glass or silicon for photolithography), and cannot be utilized in high-throughput platforms such as multi-well plates.

Precise engineering of cellular microenvironments is an exciting new addition to the biologist's toolkit; however, the fabrication complexity of many techniques impedes their implementation in standard biological labs. Accordingly, a need exists for a method for etching of physisorbed biomolecules utilizing inexpensive, easily accessible off-the-shelf cell culture materials including multi-well plates, flasks, and bottles, which method would empower biological investigations through streamlined micropatterning.

SUMMARY OF THE INVENTION

Micropatterning biomolecules and cells allows precise experimentation investigating the role of the microenvironment on cellular fate and function; however, the fabrication complexity of many micropatterning techniques limits the practicality of integration with high throughput formats. Successful large scale biological investigations require simple procedures and standard materials in order to integrate seamlessly into the process flow of the biological research lab. By merging micropatterning with standard lab materials, large scale experimentation can exploit the benefits of micropatterning without increasing experimental complexity.

One aspect of the invention described herein relates to techniques which can be used to generate micropatterns of biomolecules and cells on standard laboratory materials through selective ablation of a physisorbed biomolecule with oxygen plasma. In certain embodiments, oxygen plasma is able to ablate selectively physisorbed layers of biomolecules (e.g., type-I collagen, fibronectin, laminin, and Matrigel) along complex non-linear paths which are difficult or impossible to pattern using alternative methods. In addition, certain embodiments of the present invention relate to the micropatterning of multiple cell types on curved surfaces, multiwell plates, and flat bottom flasks. Importantly, the techniques described herein integrate seamlessly into many biological protocols through adapting to commonly used materials.

BRIEF DESCRIPTION OF THE FIGURES

FIGS. 1A-1F depict a flow chart showing one embodiment of the multi-well micropatterning method of the invention: FIG. 1A shows a schematic cross section of the PDMS etch mask; FIG. 1B shows an image of a 96 well etch mask with an insert showing the micropatterned surface of a pillar (scale bars are 8 mm in the large picture and 500 µm in the inset); FIGS. 1C and 1D show how the etch mask can be inserted into a multi-well plate and compressed with a clamp, and the clamped, masked, multi-well plate can be inserted into the barrel of a plasma asher and exposed to oxygen plasma; FIG. 1E schematically shows how the multi-well plate can be removed from the clamp, leaving the masked biomolecules behind; and FIGS. 1F and 1G show examples of fluorescently labeled collagen type-I, fibronectin, lamanin, and Matrigel micropatterned in a 96-well plate.

FIGS. 3A-3F depict a 96-well plate which was patterned with multiple geometries and seeded with primary hepatocytes. The left column represents the etch mask and the right column shows the micropatterned cells. FIGS. 3A and 3B show the complete well patterned with stars of varying points (FIG. 3A) and perpendicular lines (FIG. 3B; scale bar is 500 μm). FIGS. 3C-3F depict magnification of subregions within wells patterned with spirals (FIG. 3C; some of the spiral is not shown in the field), 20 μm squares (FIG. 3D), various sized rhomboids (FIG. 3E), and radially projecting lines (FIG. 3F).

FIG. 4A shows an image of the entire micropatterned 96-well plate; FIG. 4B shows four wells magnified to better visualize the micropattern; and FIG. 4C shows a fluorescence image showing hepatocyte islands (green) surrounded by fibroblasts (blue). The methods of the invention were also used to micropattern the inside of a flat bottom flask (FIG. 4D) and bottle (FIG. 4E) with MTT stained hepatocytes.

FIGS. 8A and 8B depict patterning in a 96-well plate with different spacing (hepatocytes on collagen and fibronectin). Each panel (A-F) shows a picture of one entire well on top and a 100× magnified view of micropatterned hepatocytes on bottom. Panel A shows micropatterned hepatocyte islands (500 micron in diameter) spaced 100 microns apart (center-to-center), while panel B shows islands spaced 100 microns apart with 50 micron hepatocyte 'bridges' connecting each island. Panels C and D are similar to panels A and B except that the center-to-center spacing between hepatocyte islands has been increased to 300 microns. Panels E and F are similar to panels A and B except the center-to-center spacing has been increased to 700 microns.

FIG. 11A shows tiny plastic (500 μm in diameter) posts for patterning collagen while FIGS. 11B and 11C show (different views) of a 24-well mold.

FIG. 12A shows morphology of primary human hepatocytes in micropatterned co-cultures over time is shown (representative micrographs at day 0 and week 1). Morphology of pure hepatocytes at week 1 is shown for comparison. Scale bars are 250 μm. FIG. 12B shows rates of albumin secretion and urea synthesis in micropatterned co-cultures and pure hepatocyte cultures over several weeks. FIG. 12C shows activities of phase I (CYP450) and phase II (conjugation) enzymes measured via fluorometric (BFC, MFC, Coumarin, 7-HC) and conventional probe substrates (Bupropion HCL and Testosterone) in micropatterned co-cultures at baseline (i.e. un-induced) over several weeks. Enzyme activities in pure hepatocytes on day 0 (6 hours after plating) and day 11 are shown for comparison. Arrows pointing to the x-axis indicate undetectable substrate metabolism in pure hepatocytes on day 11. Specific activities of CYP 3A4, 2B6 and 2A6 were measured using testosterone 6 β-hydroxylation, bupropion hydroxylation and coumarin 7-hydroxylation, respectively (see Supplemental Methods online). Phase II activity was assessed by measuring the amount of 7-Hydroxycoumarin (7-HC) conjugated with glucuronide and sulfate groups. MFC, 7-methoxy-4-trifluoromethylcoumarin; BFC, 7-benzyloxy-4-trifluoromethylcoumarin; COU, Coumarin; BUPRO; Bupropion HCL; TEST; Testosterone. All error bars represent SEM (n=3). FIG. 12D shows phase III transporter activity in micropatterned co-cultures. Cultures were incubated with 5-(and 6)-carboxy-2',7'-dichlorofluorescein diacetate, which gets internalized by hepatocytes, cleaved by esterases and excreted into bile canaliculi by Multi-drug resistance protein 2 (MRP-2).

FIG. 13A shows a global scatter plot comparing gene expression intensities in human hepatocytes purified from 6 week old micropatterned co-cultures to expression intensities in freshly isolated hepatocytes in suspension prior to plating. Similar results were obtained when gene expression intensities from hepatocytes purified from micropatterned co-cultures were compared to intensities in a fresh universal mixture of all cell types of the liver (UMIX, $R^2$=0.73, Slope=0.87). FIG. 13B shows quantitative comparison of phase I (i.e. CYP450) mRNA in hepatocytes from micropatterned co-cultures (day 42) to mRNA in freshly isolated hepatocytes. All data was normalized to gene expression levels in UMIX controls (i.e. expression level of 1). FMO, flavin containing monooxygenase; MAO, monoamine oxidase; AO, Aldehyde oxidase; EPHX1, Epoxide Hydrolase 1. FIG. 13C shows quantitative comparison as in FIG. 13B, except that various Phase II genes are displayed. UGT, UDP glycosyltransferase; SULT, sulfotransferase; COMT, catechol-O-methyltransferase; TPMT, thiopurine S-methyltransferase; HNMT, histamine N-methyltransferase; NNMT, nicotinamide N-methyltransferase, NAT, N-acetyltransferase; GST, glutathione S-transferase; MGST, microsomal glutathione S-transferase. FIG. 13D shows quantitative comparison as in FIG. 13C, except that various liver-specific genes (nuclear receptors, liver-enriched transcription factors, transporter genes) are displayed. AHR, aryl hydrocarbon receptor; CAR, constitutive androstane receptor; PXR, pregnane X receptor; RXR, retinoid X receptor; HNF, hepatocyte nuclear factor; CEBP, CCAAT/ enhancer binding protein; P-gp, P-glycoprotein; MRP3, multi-drug resistance protein 3; OCT, organic cation transporter; NTCP, sodium-dependent bile acid transporter. FIG. 13E shows a global scatter plot comparing gene expression intensities in human hepatocytes purified from micropatterned co-cultures 1 and 3 weeks after plating. FIG. 13F shows comparison of expression levels of various liver-specific transcripts in three models, which include: freshly isolated hepatocytes in suspension, pure hepatocytes 1 week after plating, and hepatocytes purified from 1 week old micropatterned co-cultures. ALB, Albumin. All data was normalized to gene expression intensities in freshly isolated hepatocytes in suspension.

FIG. 14A shows rank ordering of a panel of compounds including several known hepatotoxins by TC50—defined as the toxic concentration of drug which produces 50% decrease in mitochondrial activity after 24 hours of exposure to 1-week old tissues (acute toxicity). Mitochondrial toxicity was evaluated using the MTT assay. Inset classifies relative toxicity of structurally-related PPARγ agonists in the thiazolidinediones class (24 hour exposure at 400 µM). All data were normalized to a vehicle-only control. FIG. 14B shows time and dose-dependent chronic toxicity of Troglitazone in micropatterned co-cultures (2-3 week old). Tissues were dosed repeatedly every 48 hours. All data was normalized to mitochondrial activity in untreated cultures (100% activity). Phase micrographs show human hepatocyte morphology under untreated conditions and after treatment with 100 µM of Troglitazone for 24 hours (scale bars are 100 µm).

FIG. 15A shows dose-dependent acute toxicity profiles of model hepatotoxins after acute exposure (24 hrs). Mitochondrial activity was measured via the MTT assay. All data was normalized to vehicle controls. FIG. 15B shows dose and time-dependent induction in CYP1A activity upon incubation of micropatterned co-cultures for 1 or 3 days with β-Naphthoflavone. ER, Ethoxy-resurufin. FIG. 15C shows dose-dependent inhibition of CYP2A6 activity upon treatment of micropatterned co-cultures with Methoxsalen. Sulfaphenazole (CYP2C9 inhibitor) did not inhibit CYP2A6 activity even at a 25 µM dose. All error bars represent sEM (n=3).

FIG. 16A shows induction of CYP450 activity in micropatterned co-cultures via prototypic clinical inducers. Cultures were treated for 3-4 days before incubation with fluorometric or conventional CYP450 substrates. All data was normalized to vehicle-only controls (fold change of 1). MFC, 7-methoxy-4-trifluoromethylcoumarin; BFC, 7-benzyloxy-4-trifluoromethylcoumarin; TEST, Testosterone; ER, Ethoxy-resorufin; BUPRO, Bupropion HCL; COU, Coumarin. FIG. 16B shows inhibition of CYP450 and Phase II activities using specific inhibitors. Substrate/inhibitor combinations: BFC/ ketoconazole (CYP3A4), MFC/sulfaphenazole (CYP2C9), Coumarin/methoxsalen (CYP2A6), and 7-Hydroxycoumarin/Salicylamide (Glucuronidation). FIG. 16C shows increase in Acetaminophen (APAP) toxicity to 2 week old micropatterned co-cultures due to drug-drug interactions. CYP450s were induced in micropatterned co-cultures with Phenobarbital or glucuronidation was blocked with Probenecid prior to administration of APAP for 24 hours. FIG. 16D shows species-specific induction of CYP1A isoforms in rat and human micropatterned co-cultures. Data were normalized to vehicle-only controls.

FIG. 18A shows rates of albumin secretion and urea synthesis in the various culture models expressed as a percentage of the first 24 hour secretion values (day 1). Values from a representative day 17 are shown. FIG. 18B shows activities of CYP450 and Phase II enzymes in the various hepatocytes culture models expressed as a percentage of activities in a pure hepatocyte monolayer on day 0. Values from representative days (end of week 1 for COU, BUPRO, 7-HC and end of week 2 for TEST) are shown. COU, Coumarin; BUPRO, Buprorion HCL; TEST; Testosterone; 7 H—C, 7-Hydroxycoumarin. CYP3A4 activity was assessed by measuring production of 6 beta-hydroxytestosterone from testosterone, CYP2B6 activity by measuring production of Hydroxybupropion from bupropion HCL and CYP2A6 was assessed using the Coumarin 7-hydroxylation reaction. Phase II activity was assessed by measuring the amount of 7-hydroxycoumarin that was glucuronidated and sulfated. Arrows pointing to the x-axis indicate undetectable substrate metabolism in corresponding culture model.

FIGS. 19A-19B depict the maintenance of hepatocyte morphology in long-term micropatterned co-cultures. Elastomeric stencils (see Chapter 5 for details) were used to generate micropatterned co-cultures of primary rat hepatocytes and 3T3-J2 murine embryonic fibroblasts (500 μm islands, 1200 μm center-to-center spacing) in a multi-well format. FIG. 19A shows hepatocyte morphology remained relatively stable over time in co-cultures (phase contrast micrographs shown here up to Day 71). Hepatocytes maintained their polygonal shape, distinct nuclei and nucleoli, and visible bile canaliculi. FIG. 19B shows hepatocytes in pure cultures declined in viability and those surviving spread-out to adopt a 'fibroblastic' morphology (Days 2 & 6 shown to show the drastic differences). FIG. 19C shows pattern fidelity was well-maintained for the duration of the co-cultures (Day 20 'out-of-phase' micrograph shown).

FIG. 20A shows time-course of albumin secretion in pure hepatocyte cultures and hepatocyte-fibroblast co-cultures (random and micropatterned). FIG. 20B shows time-course as in FIG. 20A except urea synthesis is shown.

FIG. 21A shows CYP1A1 activity over 75 days in micropatterned co-cultures is compared to activity in randomly distributed co-cultures. Dealkylation of ethoxy-resorufin (EROD Activity) into fluorescent resorufin was used to assess CYP1A1 activity. Co-cultures were treated with 3 μM 3-Methylcholanthrene for 72 hours prior to assessment of CYP450 activity in order to induce enzyme levels to detectable levels. FIG. 21B shows time-course data as in 'A', except methoxy-resorufin (MR) was used as a substrate for CYP1A2.

FIG. 22A shows the rate at which CYP450 enzymes in micropatterned cocultures dealkylate substrates, MFC and BFC, into fluorescent 7-HFC. MFC, 7-methoxy-4-trifluoromethylcoumarin; BFC, 7-benzyloxy-4-trifluoromethylcoumarin; 7-HFC, 7-hydroxy-4-trifluoromethylcoumarin. Data from a single representative day (14) is shown. FIG. 22B shows phase II-mediated conjugation of glucuronic acid and sulfate groups to 7-Hydroxycoumarin (7-HC) in micropatterned co-cultures.

FIG. 24A shows induction of CYP1A enzymes in cocultures. Cocultures were incubated with 3-Methylcholanthrene (3-MC) for 3 consecutive days to induce CYP1A enzyme levels. CYP1A1 and CYP1A2 activities were assessed by the dealkylation of ethoxy-resorufin (ER) and methoxy-resorufin (MR) into fluorescent resorufin, respectively. To calculate fold induction, levels of resorufin in 3-MC treated co-cultures were normalized to levels in solvent-only (dimethylsulfoxide) treated controls. FIG. 24B shows inhibition of CYP450-mediated substrate metabolism. Co-cultures were either incubated with CYP450 substrate, 7-benzyloxy-4-trifluoromethylcoumarin (BFC), or BFC in the presence of a CYP3A inhibitor, Ketoconazole. Dealkylation of BFC into fluorescent 7-hydroxy-4-trifluoromethylcoumarin (7-HFC) was quantified via a fluorimeter.

FIG. 25A shows APAP was toxic only when co-cultures were pre-treated with DEX for 2 days. Dosing co-cultures with higher DEX concentrations further enhanced APAP-mediated toxicity. Inclusion of a CYP3A inhibitor, Troleandomycin (TAO, 100 μM), reversed the toxic effects. FIG. 25B shows hepatocyte morphology remained relatively unchanged (see arrows in pictures) upon treatment with APAP or DEX. However, in co-cultures treated with DEX and APAP, severe changes in hepatocyte morphology were seen. These changes were reversed with TAO.

FIG. 26A shows co-cultures pre-treated with EtOH were more susceptible to the toxic effects of APAP only in the presence of Caffeine. Inclusion of a CYP3A inhibitor, Troleandomycin (TAO, 100 μM), in the incubation mixture reversed the observed toxicity. FIG. 26B shows caffeine enhanced APAP-mediated toxicity in co-cultures pre-treated with different doses of DEX. TAO protected co-cultures only to a limited degree from such enhancement.

FIG. 27A shows viability in co-cultures following repeated exposures with increasing doses of acetaminophen (APAP). Co-cultures were treated with fresh toxin every 2 days. Viability was assessed via the MTT assay (see Methods). FIG. 27B shows phase contrast micrographs of co-cultures treated with varying doses of APAP for 6 days. Progressive changes in hepatocyte morphology (see arrows in select pictures) occurred with increasing APAP doses.

FIG. 28A shows viability in co-cultures following repeated exposures with increasing doses of methapyrilene. Cocultures were treated with fresh toxin every 2 days. Viability was assessed via the MTT assay. FIG. 28B shows phase contrast micrographs of co-cultures treated with varying doses of methapyrilene for 1 day. Progressive changes in hepatocyte morphology occurred with increasing toxin concentration (see arrows in select pictures).

FIG. 29A shows viability in cocultures following repeated exposures with increasing doses of pyrilamine. See text for additional details. FIG. 29B shows phase contrast micrographs of untreated co-cultures (first row) and those treated with a 100 μM dose of pyrilamine for several days. Severe changes in hepatocyte morphology were seen in pyrilamine-treated co-cultures (see arrows in select pictures).

FIG. 30A shows phase contrast micrographs demonstrating cellular morphology in co-cultures treated with varying doses of troglitazone for 1 or 5 days. FIG. 30B shows bar graphs showing viability in troglitazone-treated co-cultures. For troglitazone doses less than or equal to 113 μM, viability was not affected even after 5 days of repeated exposure.

FIG. 33A shows rate of BFC and MFC dealkylation in untreated (baseline) micropatterned rat and human co-cultures. FIG. 33B shows rate of coumarin 7-hydroxylation (CYP2A specific) in micropatterned rat and human cocultures. FIG. 33C shows rate at which 7-HC is conjugated with glucuronic acid and sulfate groups by Phase II enzymes in micropatterned rat and human co-cultures. Data from a single representative day is shown. MFC, 7-methoxy-4-trifluoromethylcoumarin; BFC, 7-benzyloxy-4-trifluoromethylcoumarin; 7-HC, 7-Hydroxycoumarin.

FIG. 34A shows a time-course of albumin secretion in the different cultures models. FIG. 34B shows phase contrast micrographs showing morphology of cells in the different culture models.

DETAILED DESCRIPTION OF THE INVENTION

Figure 2A:
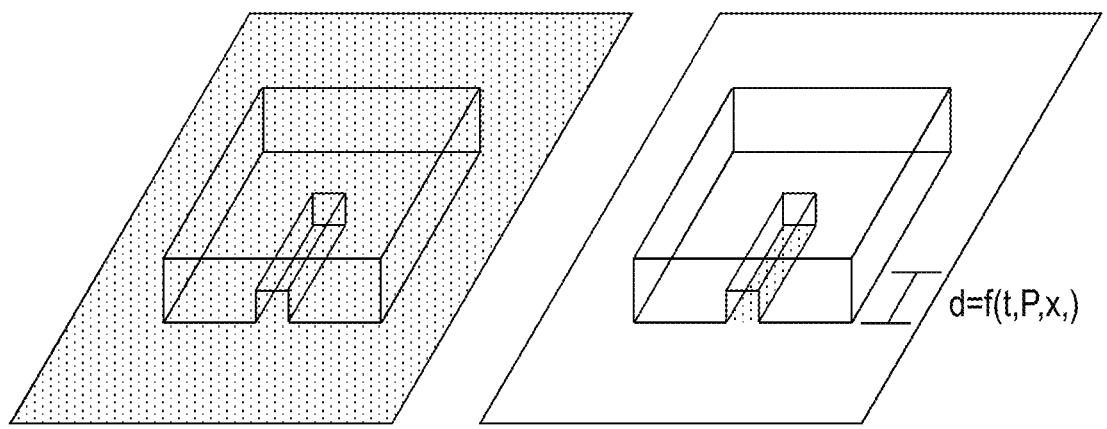
FIG. 2A depicts a schematic representation of the etch quantification. The left schematic depicts a channel etch mask on a substrate with a physisorbed biomolecule (represented as grey). The right schematic depicts the substrate after etching for a given time; notice the transition from etched (white) to not etched (grey).

Merging micropatterning techniques with high-throughput biological experimentation facilitates biological discovery through enabling precise control over microenvironmental cues not attainable through traditional techniques. Therefore, an object of the present invention is to distill micropatterning into the simplest form to facilitate broad use in standard research labs. Transitioning new technologies, such as micropatterning, into standard research labs is facilitated through the use of materials and platforms common to these fields. It follows that a method which incorporates micropatterning with the ubiquitous plastic multi-well plate would reduce the hurdle to implement such a technique in biological experimentation.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and the components that are described in the publications which might be used in connection with the presently described invention.

As summarized above, one embodiment of the invention relates to the use of an etch mask to micropattern molecules in a multi-well plate. Once an etch mask is fabricated, generating the micropatterned multi-well plate is accomplished in two simple steps: first molecules (e.g., biomolecules) are physisorbed to the surface followed by selective ablation (e.g., with oxygen plasma). FIG. 1 depicts a flow chart showing one embodiment of the multi-well micropatterning method of the invention. Panel (A) shows a schematic cross section of the PDMS etch mask and Panel (B) provides an image of a 96 well etch mask with an insert showing the micropatterned surface of a pillar. Panels (C) and (D) demonstrate how the etch mask can be inserted into a multi-well plate and compressed with a clamp. Once compressed by the clamp, the masked, multi-well plate can be inserted into the barrel of a plasma asher and exposed to oxygen plasma. The multi-well plate can be removed from the clamp as depicted in Panel (E) thereby, leaving the masked biomolecules behind. Panels (F) and (G) show examples of fluorescently labeled collagen type-I, fibronectin, lamanin, and Matrigel micropatterned in a 96-well plate.

Figure 11A:
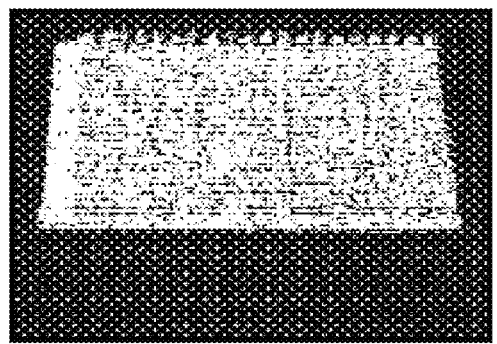
FIGS. 11A, 11B, and 11C depict exemplary solid plastic molds.
Figure 11B:
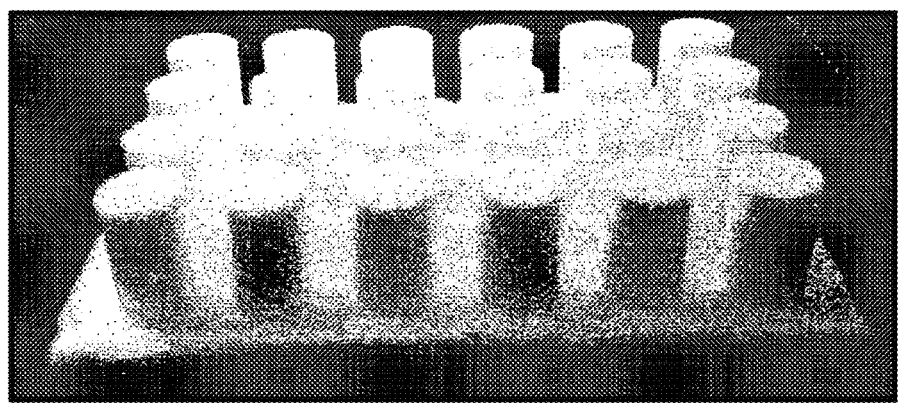
Figure 11C:
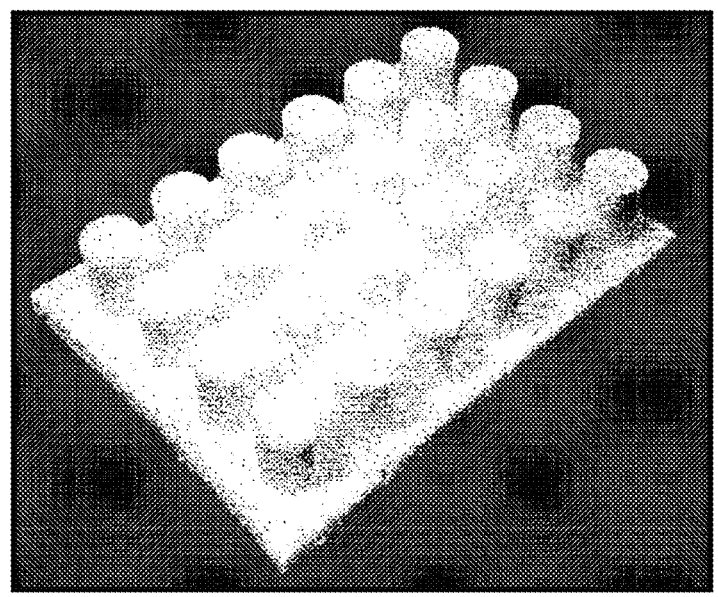

In certain embodiments, an elastomeric etch mask can be used. Two of the advantages of using an elastomeric etch mask are that it easily conforms to the substrate and it protects the physisorbed molecules from ablation. In certain embodiments, the etch mask can be formed of PDMS, rubber, chrome, or plastic. For example, FIG. 11 depicts exemplary solid plastic molds: (A) shows tiny plastic (500 μm in diameter) posts for patterning collagen while (B) and (C) show (different views) of a 24-well mold. The subject molds can be made out of solid and rubber materials (so long as it can be micromachined or molded), for example in 384-well format 24-well format and 96-well formats to date. The plates onto which patterns are created can be off-the-shelf or custom-made glass or plastic plates. In certain aspects, the etch mask may range from 10 μm to 35 mm.

Certain embodiment of the present invention require that the material which is etched can physisorb from solution and can withstand air drying. In certain embodiments, the material used is a biomaterial. In addition, in certain embodiments of the invention the concentrations of solutions used should be above 25 μg/mL as some physisorbed material may adhere to the etch mask upon removal. Due to this, etch masks should be dedicated to specific biomolecules to reduce the risk of cross-contamination. However, the adhering of biomolecules to the etch mask can be exploited to generate patterns without the use of oxygen plasma, by using the etch mask of the invention as a flexible mask.

In certain aspects, a biomolecule is adsorbed onto the surface of a substrate. The biomolecule may be a peptide, polypeptide, nucleic acid, nucleic acid binding partners, proteins, receptors, antibodies, enzymes, carbohydrates, oligosaccharids, polysaccharids, cells, cell aggregates, cell components, lipids, arrays of ligands, non-protein ligands, liposomes, and microorganisms, such as bacteria or viruses.

Any particular cell may be micropatterned according to the subject invention so long as the specific cell type requires an extracellular matrix or at least some other protein or peptide derived from the matrix for attachment such as hepatocytes or endothelial cells. Additional examples of various cell types include but are not limited to cells derived from other organs such as kidney, muscle, pancreas, epithelium cells, tissue/skin cells, intestinal cells etc. or stem-cell derived cells such as hepatocyte-like cells derived from embryonic stem cells.

For example, FIG. 3 depicts a 96-well plate which was patterned with multiple geometries and seeded with primary hepatocytes. The left column represents the etch mask and the right column shows the micropatterned cells. Panels (A) and (B) show the complete well patterned with (A) stars of varying points and (B) perpendicular lines. Panels (C) to (F) depict magnification of subregions within wells patterned with (C) spirals (some of the spiral is not shown in the field), (D) 20 μm squares, (E) various sized rhomboids, and (F) radially projecting lines.

In certain embodiments, more than one type of cell is micropatterned according to the subject invention. In this aspect, the subject methods would be employed to micropattern at least two different types of cells.

In other aspects, different coatings may be used with different pattern configurations. For example, one large post of a multi-well mold can have a different pattern configuration (i.e., one well can have 100 micron islands and another well can have 500 micron islands). As such, each well may have a different coating of a biomolecule (or other material). For example, hepatic tissue may be coated with one particular pattern on fibronectin and a different pattern on collagen or one well may have patterned hepatic tissue and another well may have kidney cells with a different pattern. In certain aspects, the coating may range from 10 nm to 1 mm.

In another aspect of the invention, the coatings do not necessarily have to be a biomolecule. For example, a virus may be patterned onto the substrate such as lentivirus. As such, when cells attach to lentivirus spots, the cells get transfected with the nucleotides the lentivirus is carrying for over-expression or knockdown of RNA and proteins. Therefore, this type of platform may be used for screening lentiviral libraries in a high-throughput format (e.g., 384 well plate). In addition this platform may also be used to deliver drugs or other agents via the micropatterned microparticles to cells. As such, the subject invention may be further employed to pattern any material, biology or non-biology related so long as the material can be protected by the posts in select regions, while the remaining regions are susceptible to plasma.

Further, in another embodiment of the invention, the etch masks of the invention can be used, as shown in FIG. 9, panels (A)-(G), to form wells, thereby providing yet another method of forming micropatterned surfaces.

In certain embodiments, the material of the invention is etched with a gas plasma. Gas plasmas, the fourth state of matter, consist of a mixture of electrons, ions, radicals, and photons and can be created by the application of RF power to a gas under vacuum. RF power excites free electrons to gain sufficient kinetic energy to causing the collision with other molecules to generate ions and radicals. These reactive radical species oxidize and ablate the adsorbed molecules (e.g., a carbon based biomolecule) and this oxidation can pattern through application of a etch mask (e,g., a PDMS etch mask). Previously, oxygen plasma micropatterning has been demonstrated for patterning biomolecules on glass substrates with selective ablation through PDMS stencils. Tourovskaia, A.; Barber, T.; Wickes, B. T.; Hirdes, D.; Grin, B.; Castner, D. G.; Healy, K. E.; Folch, A. 2003, 19, 4754-4764. Remarkably, herein it is disclosed that the plasma can penetrate more than 10 cm along non-linear paths so that the surface to be patterned does not need to be directly exposed to the oxygen plasma; this fact greatly expands the functionality of oxygen plasma based micropatterning. The technique is adaptable to any oxygen plasma system; however, the etching rate will vary with power and configuration. Importantly, this aspect of the invention enables micropatterning on standard biological materials, such as multi-well plates and flat bottom flasks, which would not be attainable through other techniques.

As such, the gas plasma used in the subject invention may be oxygen plasma, nitrogen plasma, hydrogen plasma, argon plasma, or halogen plasma. In a particular embodiment, the gas plasma is oxygen plasma.

In certain aspects, the material to be coated may be patterned by other methods. For example, the material, e.g., biomolecule, may be patterned onto the substrate by stamping techniques or pin-spotting techniques. For example, a microtechnology-based process utilizing elastomeric stencils may be employed to miniaturize and characterize human liver tissue in an industry-standard multiwell format. This approach incorporates 'soft lithography,' a set of techniques utilizing reusable, elastomeric, polymer (Polydimethylsiloxane, PDMS) molds of microfabricated structures to overcome limitations of photolithography. A process uses PDMS stencils consisting of 300 μm thick membranes with through-holes at the bottom of each well in a 24-well mold. In order to micropattern all wells simultaneously, the assembly was sealed against a polystyrene plate. Collagen-I was adsorbed to exposed polystyrene, the stencil was removed, and a 24-well PDMS 'blank' was applied. Co-cultures were 'micropatterned' by selective adhesion of primary hepatocytes to collagen-coated domains, which were then surrounded by supportive murine 3T3-J2 fibroblasts.

Figure 8A:
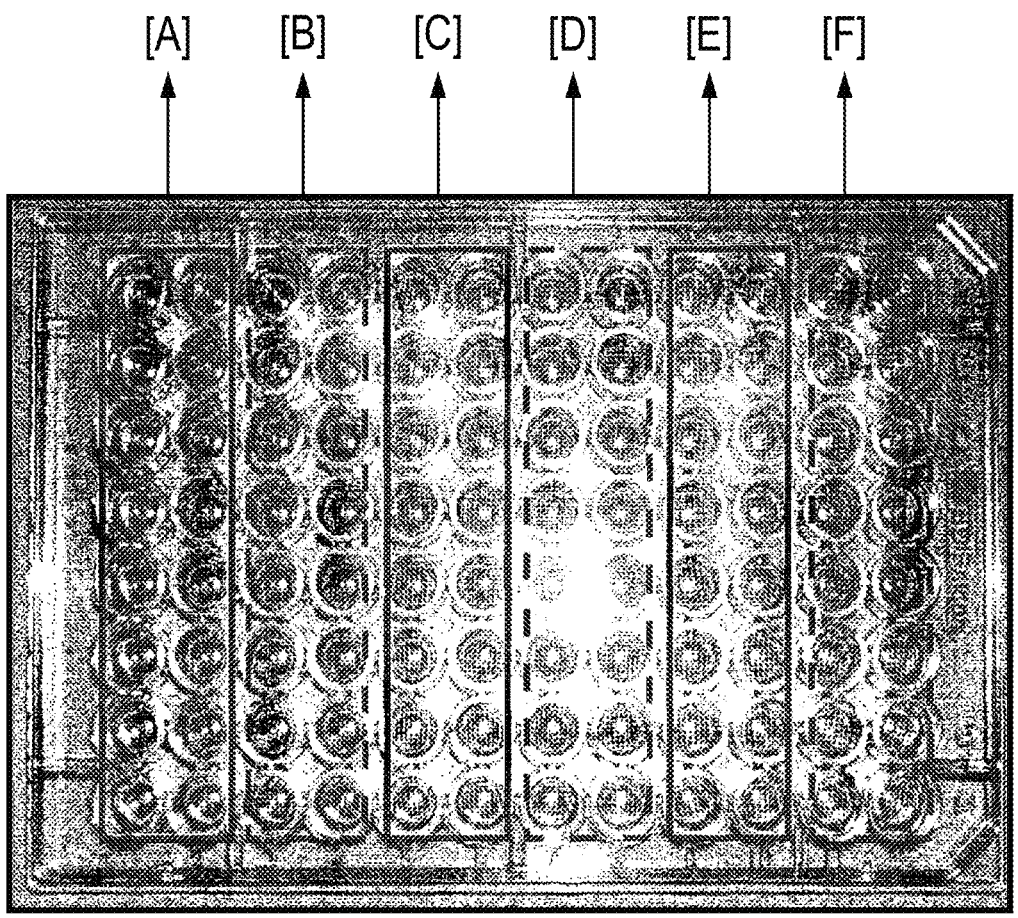
Figure 9A:
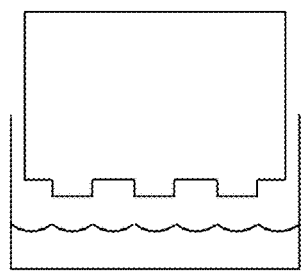
FIGS. 9A-9H depict a method of using the etch masks of the invention to form "wells" (in this case using agarose) and then to form a micropattern. Wells are filled with warm, ungelled agarose (FIG. 9A), the etch mask is pressed into the well against the agarose (FIG. 9B), and the agarose is cooled to room temperature to cause gelling (FIG. 9C). The etch mask is separated from the agarose wells and cells (or other particles such as sensor beads) are flowed into each well (FIG. 9D). Cells are allowed to settle into the wells (FIG. 9E) and remaining cells are washed away (FIG. 9F). The agarose is dissolved and washed away by gentle heating to 37 degrees Celsius, leaving a micropattern of cells (FIG. 9G). An example of fibroblast micropatterns is shown in FIG. 9H.
Figure 9B:
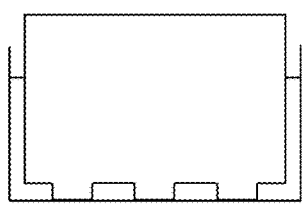
Figure 9C:
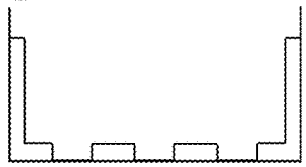
Figure 9D:
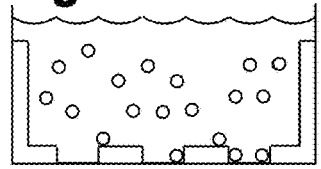
Figure 9E:
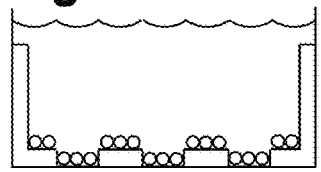
Figure 9F:
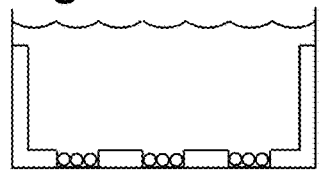
Figure 9G:
Figure 9H:
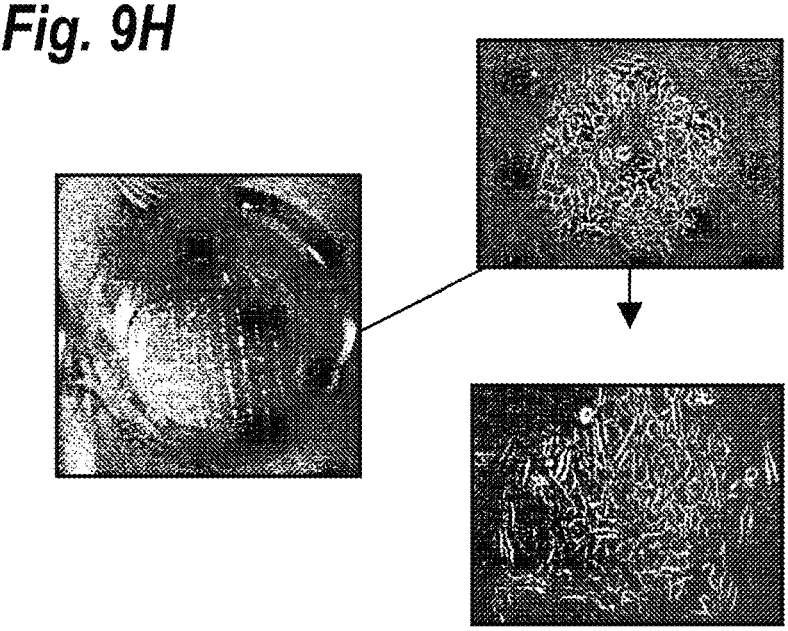

The surfaces of polystyrene multi-well plates contain more irregularities compared with the atomically uniform standard micropatterning substrate of silicon. Hence, the inventive etch masks of the invention are preferably fabricated out of elastomeric material (e.g., PDMS) in order to facilitate compression assisted sealing over the large area (8×12 cm) of the multi-well plate. In certain embodiments of the invention, the entire multi-well plate can be micropatterned with a single etch mask, which greatly reduces the time required to pattern as all 96 wells are masked in one step. In certain embodiments, each pillar of the etch mask can have a different micropattern (as shown in FIG. 8, panels (A) to (F)). FIG. 8 depicts patterning in a 96-well plate with different spacing (hepatocytes on collagen and fibronectin). Each panel (A-F) shows a picture of one entire well on top and a 100× magnified view of micropatterned hepatocytes on bottom. Panel A shows micropatterned hepatocyte islands (500 micron in diameter) spaced 100 microns apart (center-to-center), while panel B shows islands spaced 100 microns apart with 50 micron hepatocyte 'bridges' connecting each island. Panels C and D are similar to panels A and B except that the center-to-center spacing between hepatocyte islands has been increased to 300 microns. Panels E and F are similar to panels A and B except the center-to-center spacing has been increased to 700 microns.

Figure 5:
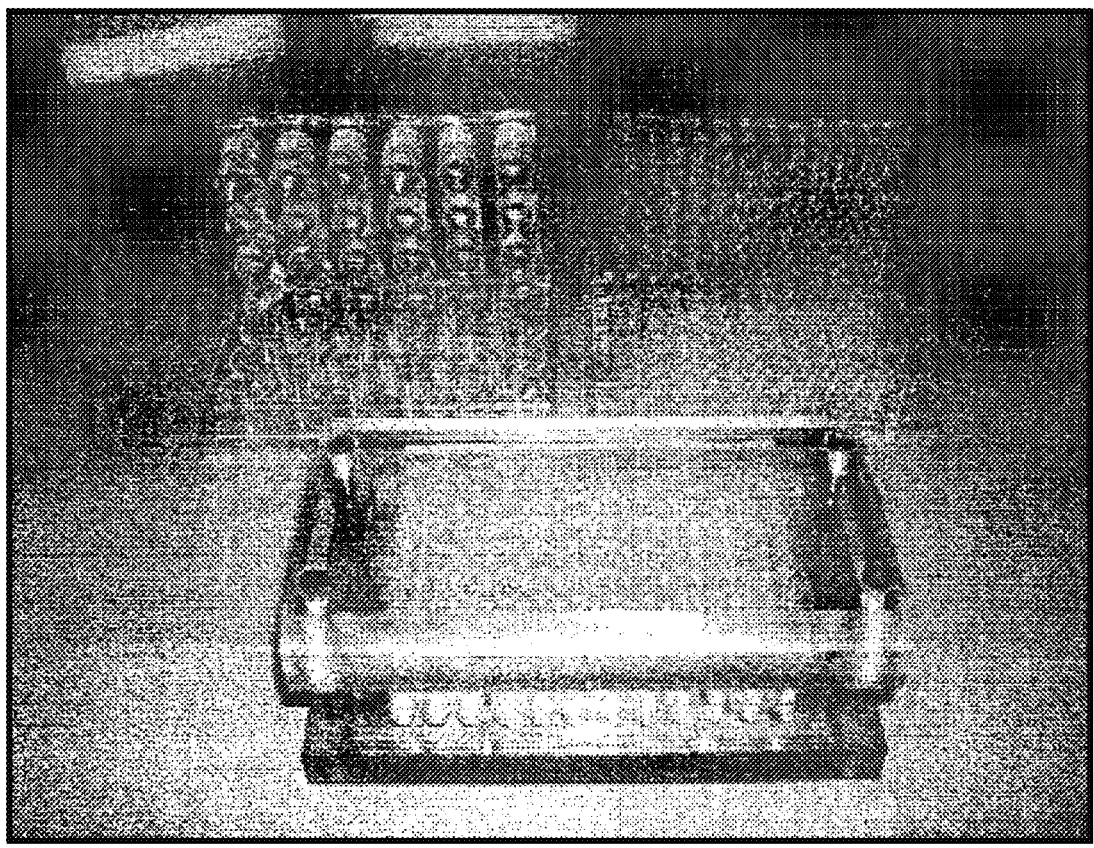
FIG. 5 depicts an etch mask for 24-well and 96-well plates, shown over the respective multiwell plates (above) and a mask holder (below) which compresses the mask onto the multiwell plate.
Figure 6A:
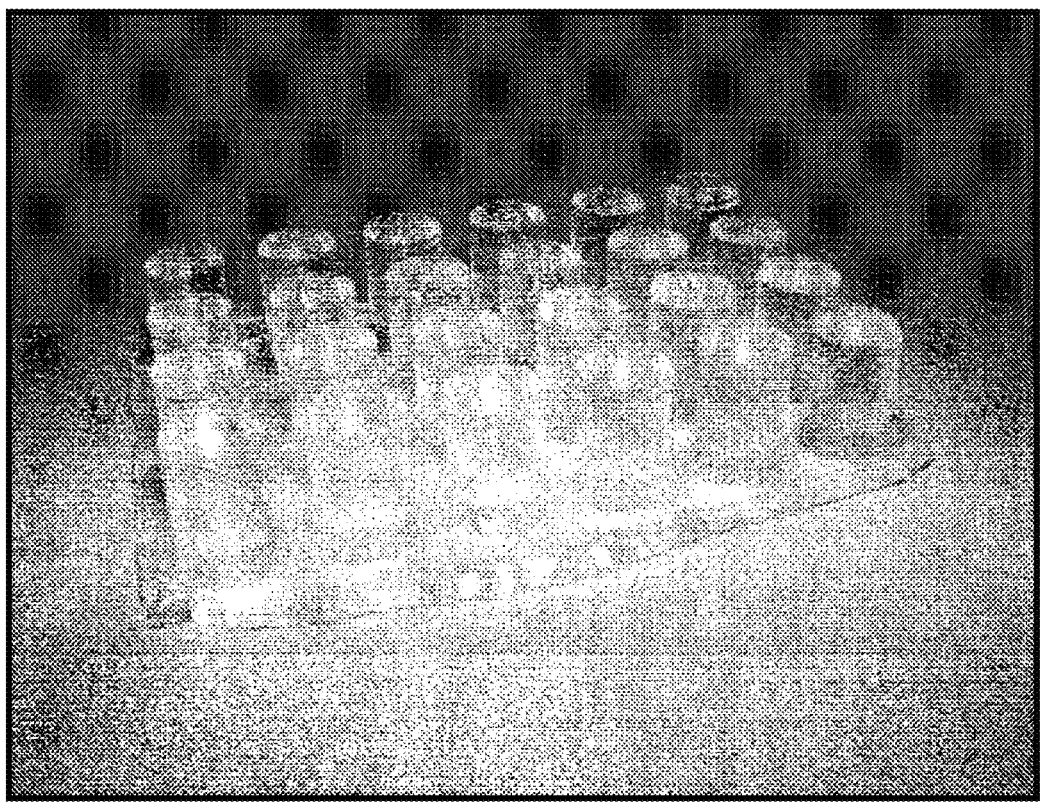
FIG. 6A depicts an etch mask for a 24-well plate and FIG. 6B depicts detail of the surface of one pillar of the etch mask.
Figure 6B:
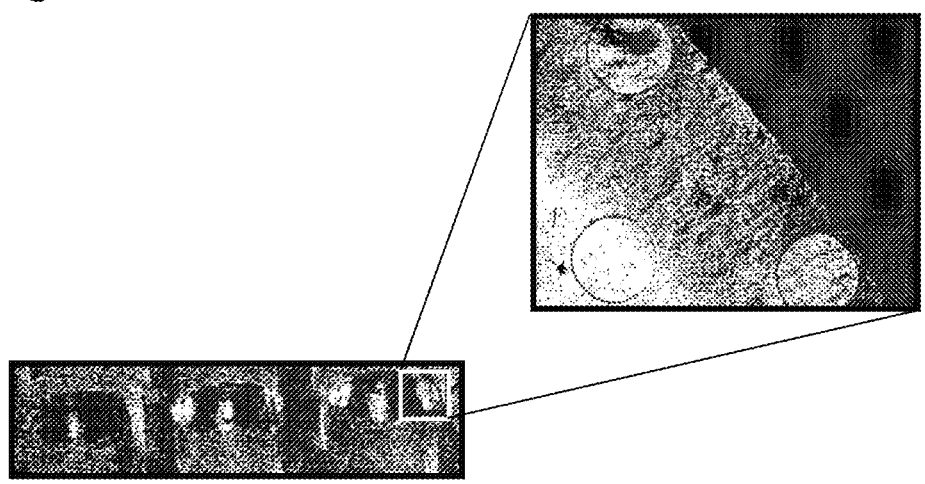

A custom clamp can be used to compress uniformly the etch mask to the surface of the multi-well plate as shown in FIG. 1D. The clamp is required for the multi-well plates as the supporting pillars of each well create a large lever arm which easily delaminates the mask from the bottom of the well. Therefore, the clamp is utilized to gently compress the etch mask and generate complete sealing of the etch mask to the well surface. FIG. 5 depicts an etch mask for 24-well and 96-well plates, shown over the respective multiwell plates (above) and a mask holder (below) which compresses the mask onto the multiwell plate. In addition, FIG. 6 panel (A) depicts an etch mask for a 24-well plate and panel (B) provides a detail view of the surface of one pillar of the etch mask.

Micropatterns of fluorescently labeled type-I collagen, fibronectin, laminin, and Matrigel are shown in FIG. 1G. In addition, as mentioned above, the technique is not limited to the above mentioned biomolecules, and can be extended to any molecule able to physisorb to the surface of a multi-well plate and, in the case of biomolecules (for certain applications) remain active upon air-drying.

Figure 4A:
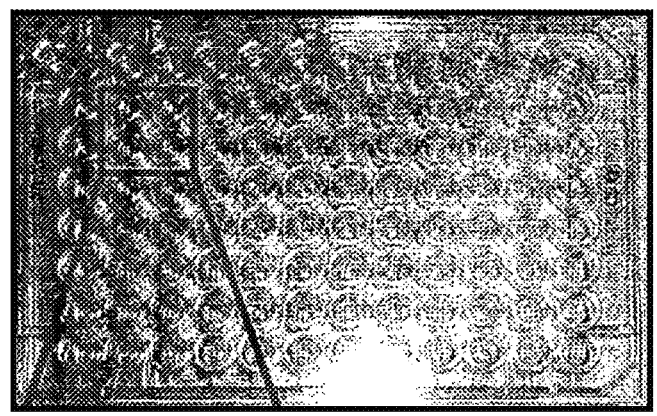
FIGS. 4A-4E depict micropatterned hepatocyte-fibroblast co-cultures in a 96-well plate.
Figure 4B:
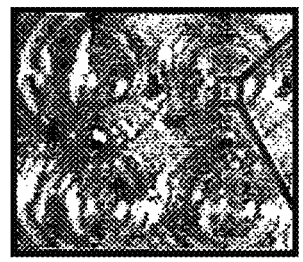
Figure 4C:
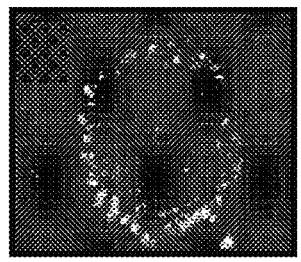
Figure 4D:
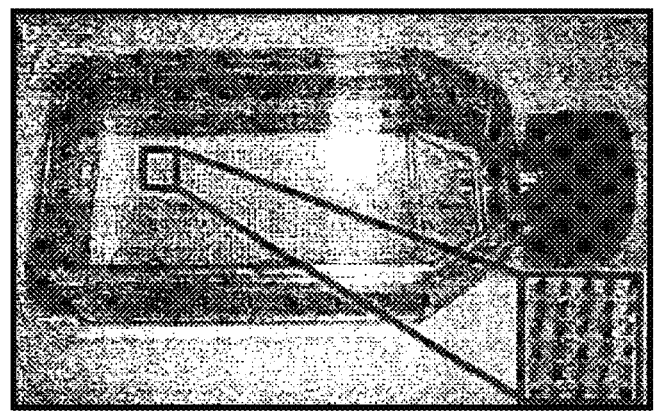
Figure 4E:
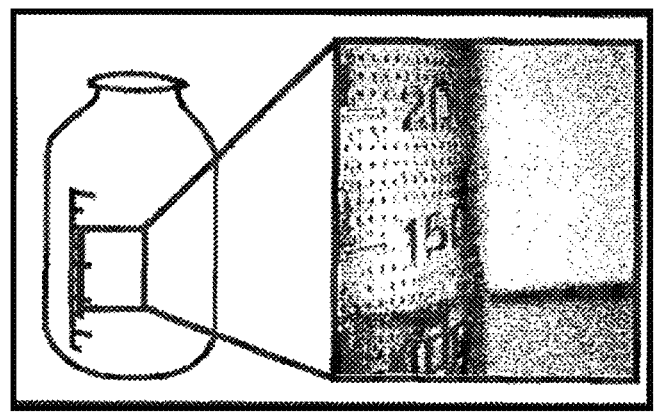
Figure 10:
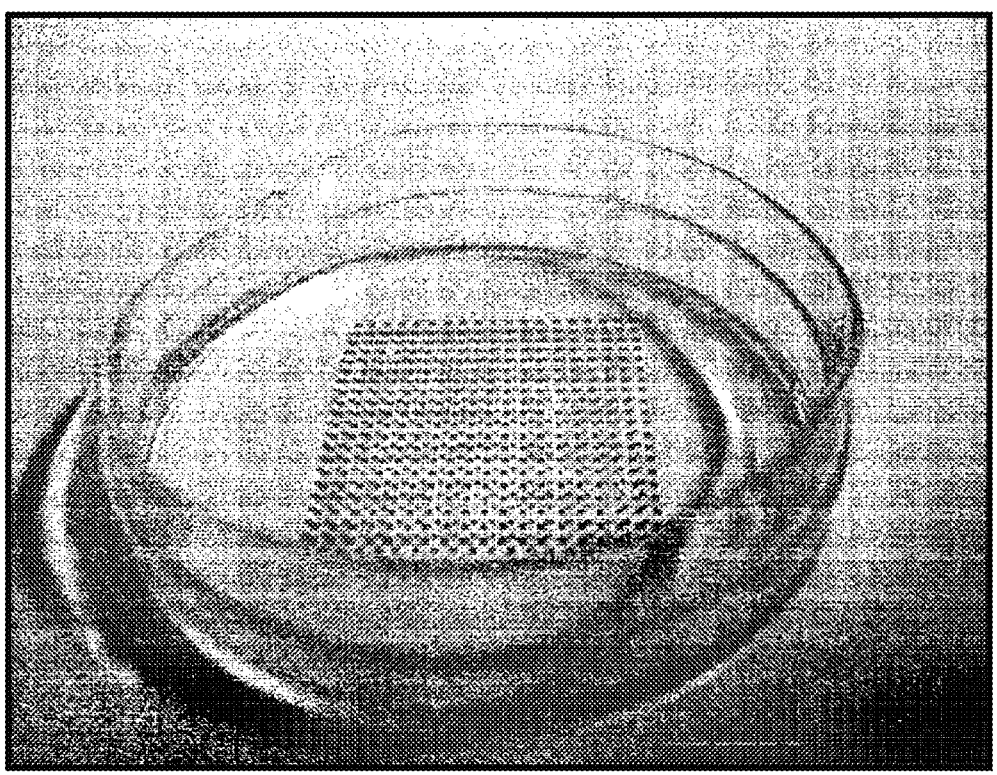
FIG. 10 depicts an example of micropatterned islands of liver cells created using a solid plastic structure. The plastic was Delrin (Dupong) and coated with a rubber plastic on the bottom prior to using with collagen and ultimately cells.

The power of this technique lies in the adaptability and simplicity of the method. To further demonstrate, the interior surface of flat-bottom tissue culture flasks and bottles were micropatterned with type-I collagen and seeded with primary hepatocytes as shown in FIGS. 4A to 4C. Tissue culture flasks and bottles are the workhorses of standard biological labs and enabling micropatterning within these systems greatly reduces the hurdle for implementing micropatterning in standard biological experimentation. Micropatterning flasks and bottles does not require the compression clamp as the etch mask is thin (1 mm) and not attached to the pillars which easily delaminate the etch mask. Micropatterned flasks expand the utility of micropatterning into new areas, such as micropatterned feeder cell layers. In addition, curved surfaces can be micropatterned as shown in FIG. 4C. This capability opens the possibility of micropatterning roller bottle cultures and further demonstrates the ability to micropattern any material or surface as long as they can physisorb biomolecules and an elastomeric etch mask can conform to the surface. For example, FIG. 10 depicts an example of micropatterned islands of liver cells created using a solid plastic structure. The plastic was Delrin (Dupong) and coated with a rubber plastic on the bottom prior to using with collagen and ultimately cells.

Figure 2B:
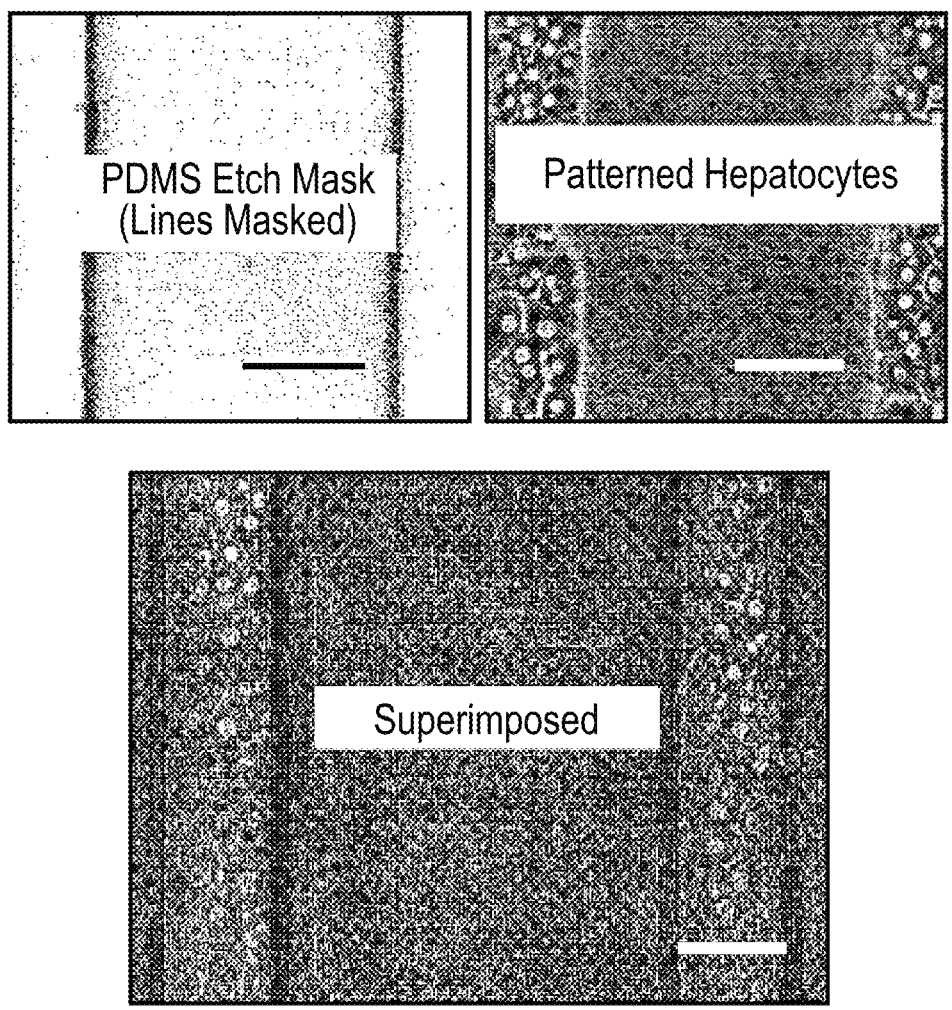
FIG. 2B depicts images of the PDMS etch mask (left) and the corresponding micropatterned hepatocytes (right), along with a superimposed bottom image aligning the two demonstrating the masking fidelity.
Figure 2C:
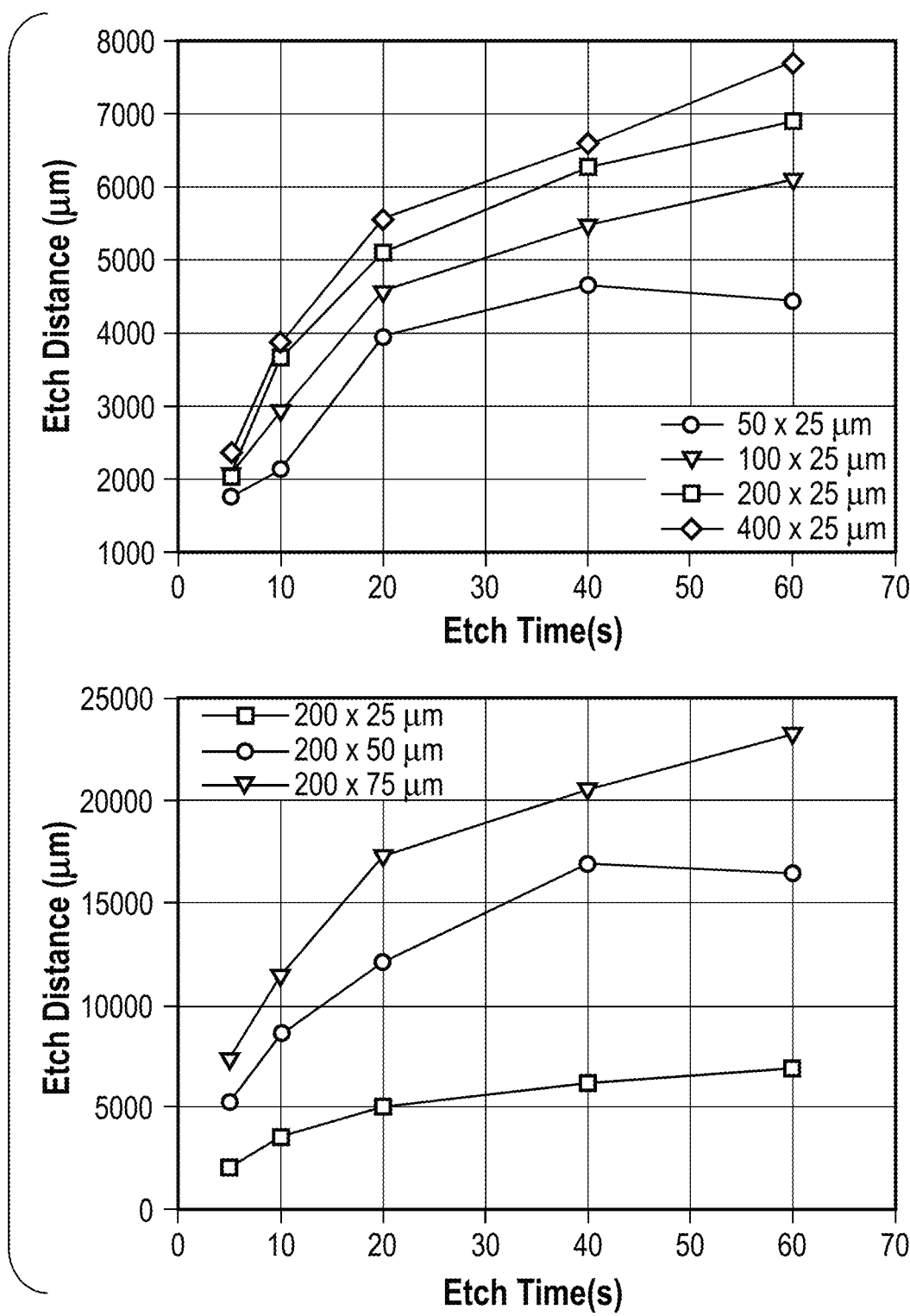
FIG. 2C depicts a graph of etch distance with respect to changing widths for a given height (left) and etch distance with respect to height for a given width.

The resolution and performance of this technique were explored through the quantification of etching distances along straight microchannel etch masks as shown in FIG. 2A. Primary rat hepatocyte adhesion was used as a simple bioassay to quantify the presence of collagen as hepatocytes can attach to very low levels of collagen. Primary rat hepatocytes seeded onto the micropatterned type-I collagen substrate preferentially adhere to type-I collagen domains. This bioassay was utilized as hepatocyte attachment simultaneously indicates collagen micropatterning and preserved collagen bioactivity. The result is a transition of no hepatocyte attachment to hepatocyte attachment corresponding to etching distance along the microchannel. Increasing etch times correspond to increased etching into the microchannel. As seen in FIG. 2B, hepatocyte attachment corresponds directly to masked regions with high fidelity. The smallest feature size of the etch mask throttles the etch rate, however the width and height regulate the etch rate differently as shown in FIG. 2C. As the width continually doubles, the etching distance increases, but not at the same rate. However, when the height doubles the resulting distances etched approximately double suggesting a direct relationship between height and distance etched. This observation may be due to the directionality of the oxygen plasma driven towards the bottom electrode of the plasma chamber. Therefore, increased height corresponds to more available plasma driven into the substrate. More generally, increased time in oxygen plasma and larger etch mask features increase the etching rate.

Figure 7A:
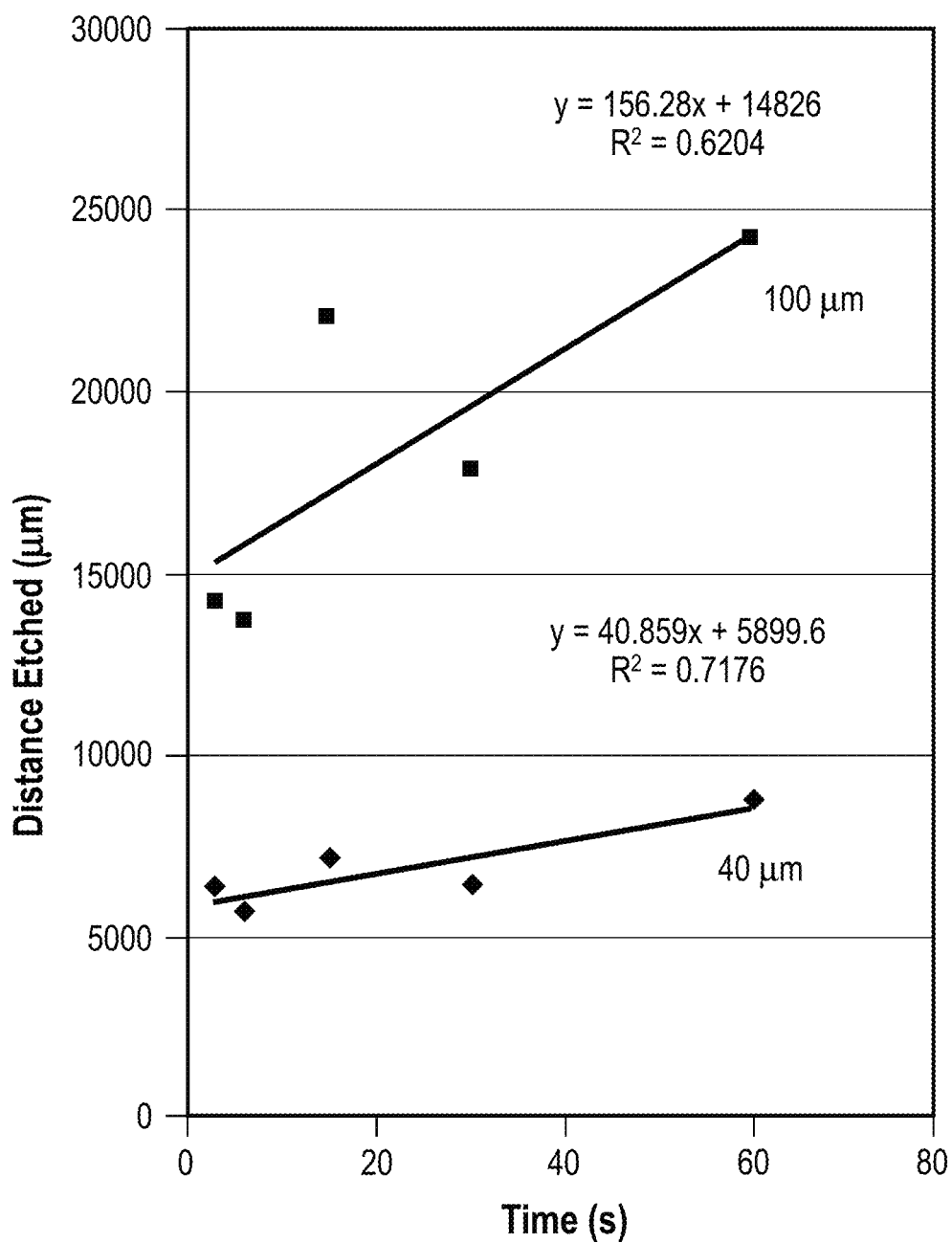
FIG. 7A depicts plots of plasma etch distance with respect to plasma etch time and distance and smallest feature sizes possible. The distance of collagen etched by plasma with respect to plasma exposure time and channel dimensions (100 micron feature size for top line and 40 micron for bottom one) are quantified.
Figure 7B:
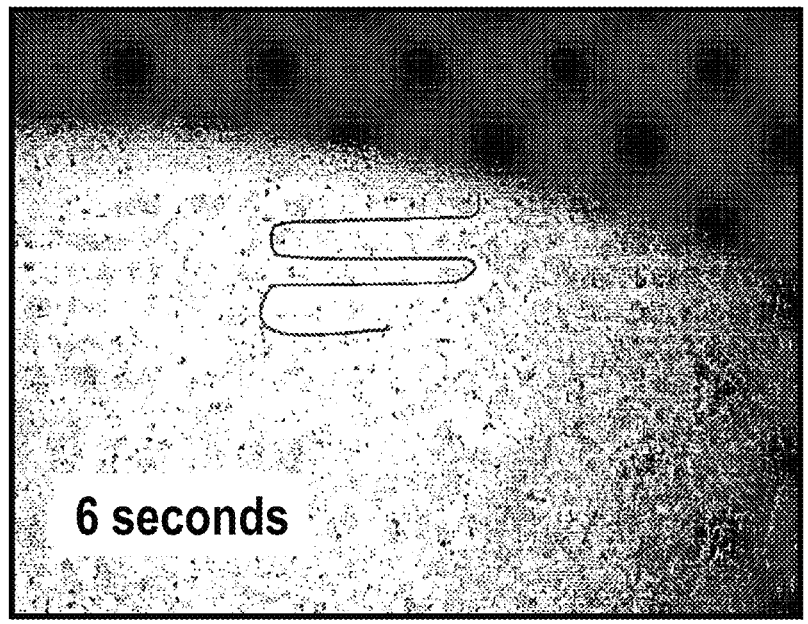
FIG. 7B depicts the micropatterning of primary rat hepatocytes was utilized to show etching of collagen along a microchannel after 6 seconds.
Figure 7C:
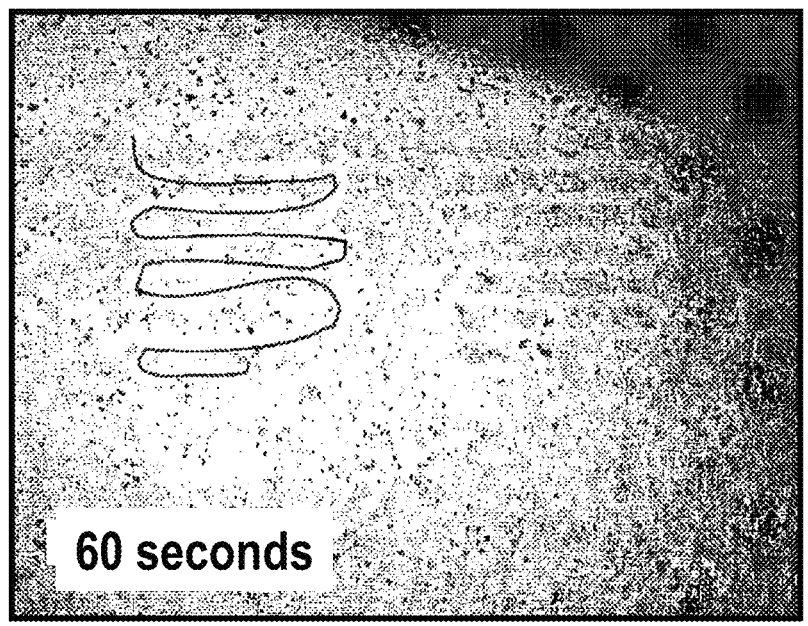
FIG. 7C depicts the micropatterning of primary rat hepatocytes was utilized to show etching of collagen along a microchannel after 6 seconds and 60 seconds of plasma exposure.

The resolution of the technique can be limited by the resolution of the etch mask. In certain embodiments, patterns were generated down to 20 µm, the limit of the high resolution transparency photomasks used for SU8 mold fabrication; however, smaller features could be fabricated through the use of a high resolution chrome photomask. However, smaller features often require longer etching times, and increasing the etching time can cause the temperature of the substrate to increase. For example, FIG. 7 depicts plots of plasma etch distance with respect to plasma etch time and distance and smallest feature sizes possible. Panel A quantifies distance of collagen etched by plasma with respect to plasma exposure time and channel dimensions (100 micron feature size for top line and 40 micron for bottom one). Micropatterning of primary rat hepatocytes was utilized to show etching of collagen along a microchannel after 6 seconds (Panel B) and 60 seconds (Panel C) of plasma exposure. In certain embodiments, etching times ranging from 60-120 seconds are suitable to obtain the micropatterning desired. For example, physisorbed type-I collagen substrates were treated with plasma at 100 W for 100 seconds and hepatocytes attached successfully to the masked collagen domains demonstrating the activity of the binding motifs remain active under prolonged etching conditions.

The oxygen plasma ablates any exposed surface within the barrel of the plasma asher and can generate complex patterns, such as spirals and non-linear paths as shown in FIG. 3, which would be difficult to pattern over large scales in traditional materials using other micropatterning techniques. In addition to pattern complexity, this method simultaneously generates micropatterns within all 24 wells of a standard 24-multi-well plate, or 96 wells of a standard 96 multi-well plate or within all 384 wells of a standard 384 multi-well plate. The modular construction of the elastomeric etch mask allows experimental flexibility as each well in a multi-well plate can be simultaneously masked with a different pattern. The high-throughput nature of the method combined with the remarkable complexity of the pattern geometries and versatility of the materials able to be patterned enables new applications not possible with traditional micropatterning techniques.

This invention has broad potential applications as an in vitro model of cellular systems. Micropatterning of biomolecules can be designed to engineer precisely cellular position, shape, and interactions with extra cellular matrix. For example, the invention contemplates a hepatocyte-fibroblast micropatterned co-culture system as an in vitro model of the liver, as shown in FIG. 4A. Previous results demonstrated micropatterned co-cultures of hepatocyte islands surrounded by supportive murine 3T3-J2 fibroblasts enhance hepatocyte specific function as compared with co-cultures or hepatocyte monolayers. Bhatia, S, N.; Balis, U. J.; Yarmush, M. L.; Toner, M. Faseb J 1999, 13, 1883-1900. The diameter of the hepatocyte island directly modulates the degree of homotypic (hepatocyte/hepatocyte) and heterotypic (hepatocyte/fibroblast) interactions and this parameter space was probed and an optimum hepatocyte diameter of 500 µm was previously identified. Here we present a straightforward approach to generate these optimized micropatterned substrates in a high throughput format. As the dimensions of the micropattern are fixed, the same etch mask can be reused repeatedly. For example, an etch mask has been used more than 100 times with no deterioration of the generated micropattern.

Furthermore, micropatterning in multiwell plates will facilitate high throughput biological experiments not possible with traditional techniques. Current micropatterning techniques are primarily in the proof-of-concept stage and are not easily adaptable to large scale investigations. This invention overcomes these limitations and enables large scale experimentation. To date, there have been no demonstrations of micropatterning inside standard multiwell plates. This fact is primarily due to most micropatterning procedures either require solvents that would degrade standard tissue culture plates, extremely flat surfaces (Si wafers or plasma cleaned glass slides), or specialized substrates (gold substrate for self-assembled monolayers). The methods described herein are robust and require no specialized surfaces. Importantly, due to the deep penetration properties of plasma, virtually any surface morphology can be patterned in one step.

Selected Methods of the Invention

One aspect of the invention relates to a method of forming a micropatterned substrate, comprising the steps of: adsorbing molecules onto a surface of a substrate, thereby forming a coated surface of the substrate; compressing a micropatterned etch mask onto the coated surface of said substrate; and exposing the compressed micropatterned etch mask and coated surface of the substrate to a gas plasma for a period of time, thereby ablating the exposed surfaces of the substrate.

In certain embodiments, the present invention relates to the aforementioned method, further comprising rinsing and drying said coated surface after the adsorbing step.

In certain embodiments, the present invention relates to the aforementioned method, wherein said exposing step is carried out in a plasma asher.

In certain embodiments, the present invention relates to the aforementioned method, wherein the micropatterned etch mask is one solid elastomeric piece.

In certain embodiments, the present invention relates to the aforementioned method, wherein the micropatterned etch mask comprises a plurality of pillars.

In certain embodiments, the present invention relates to the aforementioned method, wherein the micropatterned etch mask comprises chrome or elastomeric poly(dimethylsiloxane) or rubber or plastic.

In certain embodiments, the present invention relates to the aforementioned method, wherein the micropatterned etch mask comprises elastomeric poly(dimethylsiloxane).

In certain embodiments, the present invention relates to the aforementioned method, wherein the micropatterned etch mask comprises an about 50 µm to about 1 mm thick piece of elastomeric poly(dimethylsiloxane).

In certain embodiments, the present invention relates to the aforementioned method, wherein said substrate surface is ceramic, metal, glass, or plastic.

In certain embodiments, the present invention relates to the aforementioned method, wherein said substrate surface is plastic.

In certain embodiments, the present invention relates to the aforementioned method, wherein said substrate comprises fluoropolymers, fluorinated ethylene propylene, polyvinylidine, polydimethylsiloxane, polystyrene, polycarbonate, and polyvinyl chloride, fused silica, polysilicon, or single silicon crystals.

In certain embodiments, the present invention relates to the aforementioned method, wherein said substrate is a tissue culture flask, a tissue culture bottle, or a cell culture multiwell plate.

In certain embodiments, the present invention relates to the aforementioned method, wherein said substrate is a 24-well, 96-well, or 384-well cell culture plate.

In certain embodiments, the present invention relates to the aforementioned methods wherein said molecules are biomolecules.

In certain embodiments, the present invention relates to the aforementioned method, wherein said molecules are biomolecules; and said biomolecules are selected from the group consisting of peptides, polypeptides, nucleic acids, nucleic acid binding partners, proteins, receptors, antibodies, enzymes, carbohydrates, oligosaccharides, polysaccharides, cells, cell aggregates, cell components, lipids, arrays of ligands, non-protein ligands, liposomes, and microorganisms.

In certain embodiments, the present invention relates to the aforementioned method, wherein said molecules are hyaluronic acid, collagen, fibronectin, lamanin, or matrigel.

In certain embodiments, the present invention relates to the aforementioned method, wherein the thickness of the coating on the surface is in the range from about 100 nm to about 200 nm.

In certain embodiments, the present invention relates to the aforementioned method, wherein the thickness of the coating on the surface is about 150 nm.

In certain embodiments, the present invention relates to the aforementioned method, wherein the gas plasma is an oxygen plasma, nitrogen plasma, hydrogen plasma, argon plasma or halogen plasma.

In certain embodiments, the present invention relates to the aforementioned method, wherein the gas plasma is an oxygen gas plasma.

In certain embodiments, the present invention relates to the aforementioned method, wherein said time is in the range from about 5 seconds to about 1000 seconds.

In certain embodiments, the present invention relates to the aforementioned method, wherein said time is about 5 seconds, 10 seconds, 20 seconds, 40 seconds, 60 seconds or 120 seconds.

In certain embodiments, the present invention relates to the aforementioned method, wherein the substrate is a 96-well plate; and the molecules comprise collagen, fibronectin, lamanin, or matrigel.

In certain embodiments, the present invention relates to the aforementioned method, wherein the substrate is a tissue culture flask; and the molecules comprise collagen, fibronectin, lamanin, or matrigel.

In certain embodiments, the present invention relates to the aforementioned method, wherein the substrate is a tissue culture bottle; and the molecules comprise collagen, fibronectin, lamanin, or matrigel.

In certain embodiments, the present invention relates to the aforementioned method, wherein the substrate is a 96-well cell culture plate; the molecules comprise collagen; and the time is about 1000 seconds, In certain embodiments, the present invention relates to the aforementioned method, wherein the substrate is a 96-well cell culture plate, and the micropattern is generated within all 96 wells simultaneously.

In certain embodiments, the present invention relates to the aforementioned method, wherein the substrate is a 384-well cell culture plate; the molecules comprise collagen; and the time is about 1000 seconds, In certain embodiments, the present invention relates to the aforementioned method, wherein the substrate is a 384-well cell culture plate, and the micropattern is generated within all 384 wells simultaneously.

In certain embodiments, the present invention relates to the aforementioned method, further comprising the steps of: removing the micropatterned etch mask; and contacting said micropatterned substrate with cells.

In certain embodiments, the present invention relates to the aforementioned method, wherein said cells are hepatocytes.

In certain embodiments, the present invention relates to the aforementioned method, wherein said cells are human or rat hepatocytes.

Selected Multi-Well Cell Culture Plates of the Invention

Another aspect of the invention relates to a multi-well cell culture plate, wherein each cell is micropatterned with a material.

In certain embodiments, the present invention relates to the aforementioned multi-well plate, wherein said multi-well cell culture plate is plastic.

In certain embodiments, the present invention relates to the aforementioned multi-well plate, wherein said multi-well cell culture plate is a 24-well, 96-well, or a 384-well cell culture plate.

In certain embodiments, the present invention relates to the aforementioned multi-well plate, wherein said material is a biomolecule.

In certain embodiments, the present invention relates to the aforementioned multi-well plate, wherein said material is a biomolecule; and said biomolecule is selected from the group consisting of peptides, polypeptides, nucleic acids, nucleic acid binding partners, proteins, receptors, antibodies, enzymes, carbohydrates, oligosaccharides, polysaccharides, cells, cell aggregates, cell components, lipids, arrays of ligands, non-protein ligands, liposomes, and microorganisms.

In certain embodiments, the present invention relates to the aforementioned multi-well plate, wherein said material is hyaluronic acid, collagen, fibronectin, lamanin, or matrigel.

In certain embodiments, the present invention relates to the aforementioned multi-well plate, wherein the thickness of the material on the multi-well cell culture plate is in the range from about 100 nm to about 200 nm.

In certain embodiments, the present invention relates to the aforementioned multi-well plate, wherein the thickness of the material on the multi-well cell culture plate is about 150 nm.

In certain embodiments, the present invention relates to the aforementioned multi-well plate, wherein the multi-well cell culture plate is a 96-well plate; and the molecules comprises collagen, fibronectin, lamanin, or matrigel.

In certain embodiments, the present invention relates to the aforementioned multi-well plate, wherein each cell of the multi-well cell culture plate has the same micropattern.

In certain embodiments, the present invention relates to the aforementioned multi-well plate, wherein not all of the cells of the multi-well cell culture plate has the same micropattern.

In certain embodiments, the present invention relates to the aforementioned multi-well plate, further comprising cells.

In certain embodiments, the present invention relates to the aforementioned multi-well plate, wherein said cells are hepatocytes.

Selected Etch Masks of the Invention

Another aspect of the invention relates to a micropatterned etch mask comprising a plurality of pillars.

In certain embodiments, the present invention relates to the aforementioned micropatterned etch mask, wherein the micropatterned etch mask is one solid elastomeric piece.

In certain embodiments, the present invention relates to the aforementioned micropatterned etch mask, wherein the micropatterned etch mask comprises chrome or elastomeric poly(dimethylsiloxane) or rubber or plastic.

In certain embodiments, the present invention relates to the aforementioned micropatterned etch mask, wherein the micropatterned etch mask comprises elastomeric poly(dimethylsiloxane).

In certain embodiments, the present invention relates to the aforementioned micropatterned etch mask, wherein the micropatterned etch mask comprises an about 50 µm to about 1 mm thick piece of elastomeric poly(dimethylsiloxane).

Kits

Finally, kits for use with high throughput biological experiments and/or for in vitro models of cellular systems are provided. The subject kits at least include the cell culture plates and etch masks of the subject invention. The kits may further include one or more additional components necessary for carrying out the biological experiments or creating the in vitro models, such as sample preparation reagents, buffers, labels, and the like.

In addition to above mentioned components, the subject kits typically further include instructions for using the components of the kit to practice the subject methods with the subject devices. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXEMPLIFICATION

The invention now being generally described, it will be more readily understood by reference to the following examples, which are included merely for purposes of illustration of certain aspects and embodiments of the present invention, and are not intended to limit the invention. Note that these studies employed a 4"×6" 100W barrel asher (March Plasmod, Concord, Calif.) as the oxygen plasma system.

Example 1—Fabrication of the 96-Well Etch Mask

A mold was machined with the same center to center spacing as a standard 96-well plate and was used to generate the support structure for the 96-well etch mask. This support structure consisted of an array of 96 pillars spaced evenly to allow nesting in a standard 96-well plate. The support structure is molded out of poly(dimethylsiloxane) (PDMS) (sylgard 184, Dow Corning, Midland, Mich.) and prepared using standard techniques. Duffy, D. C.; McDonald, J. C.; Schueller, O. J. A.; Whitesides, G. M. *Analytical Chemistry* 1998, 70, 4974. In a separate step, mold masters for the micropatterns were fabricated with SU8 photoresist (Microchem, Newton, Mass.) using a high resolution transparency photomask. The molds were fabricated to have 50 µm thick features. These mold masters were coated with a layer of PDMS 2 mm thick The PDMS was peeled from the mold and circles were punched out with a cork borer and glued to the pillars of the PDMS support structure using PDMS as an adhesive. This resulted in a single etch mask with 96 micropatterned pillars able to nest inside a standard 96-well plate and conform to the bottom of the plate under slight compression.

Example 2—Patterning Protein and Cells in 96-Well Plates

Biomolecules were physisorbed to each well of a standard multi-well plate (solutions of type-I collagen, fibronectin, Matrigel and laminin at 50 µg/mL in water. Note that 1×PBS may be used instead of water. The multi-well plates were incubated for 1 hour at 37° C. followed by rinsing with water and allowed to air dry. This results in an adsorbed thickness of approximately 150 nm. Gurdak, E.; Dupont-Gillain, C. C.; Booth, J.; Roberts, C. J.; Rouxhet, P. G. *Langmuir* 2005, 21, 10684-10692. In some cases, micropatterned proteins were fluorescently labeled via incubation (1 hour at room temperature) with Alexa Fluor® 488 carboxylic acid, succinimidyl ester (Invitrogen, Carlsbad, Calif.) dissolved in phosphate buffered saline (PBS) at 20 µg/mL. A single etch mask was inserted into the multi-well plate and compressed in a custom clamp consisting of two blocks of polycarbonate flanking the masked multi-well plate and compression was applied by tightening screws joining the two blocks as Shown in FIG. 1C. The clamped, masked multi-well plate was placed inside the barrel of a 4"×6" plasma asher and exposed to an oxygen plasma at 100 W power for 2 minutes. The clamp and etch mask were removed and the micropatterned multi-well plate was sterilized using a 15 W, 254 nm germicidal UV light prior to hepatocyte seeding.

Primary rat hepatocytes were seeded into the multi-well plate isolated and purified by a modified procedure of Seglen. Seglen, P. O. *Methods Cell Bio* 11976, 13, 29-83. Briefly, 2-3 month old adult female Lewis rats (Charles River Laboratories, Wilmington, Mass.) weighing 180-200 g were anesthetized prior to in situ perfusion of the portal vein. Following a two-step perfusion of Krebs Ringer Buffer and collagenase, dissociated cells were passed through nylon mesh and purified on a Percoll gradient.

Example 3—Ablation Quantification

A PDMS etch mask containing dead-end microchannels with channel widths of 50, 100, 150, and 200 µm repeated for three channel heights of 25, 50, and 75 µm (12 channels total) was used to quantify the etching rate. The mask was placed onto p60 petri dishes physisorbed with type-I collagen and exposed to oxygen plasma for several time points (5, 10, 20, 40, and 60 seconds) with each time point on a separate dish. Primary rat hepatocytes were then seeded onto the patterned dishes and cultured for 24 hours. The hepatocytes specifically attached to regions with type-I collagen, hence plasma ablated distances could be directly correlated to hepatocyte attachment as hepatocytes will not attach to adsorbed collagen substrates from solutions less than 0.5 µ/mL. The distances were measured using Metamorph (Universal Imaging, Sunnyvale, Calif.) and plotted as a function of time.

Example 4—Micropatterning Two Cell Types

Primary hepatocytes and a supportive murine fibroblast were co-cultivated by first micropatterning adhesive type-I collagen microdomains on the substrate of a 96-well plate. Hepatocytes were seeded at a density of $0.5 \times 10^6$ cells/mL in serum free media and allowed to spread on the collagen domains. Unattached hepatocytes were rinsed off and fibroblasts were seeded in media containing serum at $0.5 \times 10^6$ cells/mL. Components of the serum adsorbed to the regions of the substrate not containing type-I collagen domains (or hepatocytes) and fibroblasts attached and spread.

Example 5—Flask and Bottle Micropatterning

Type-I collagen solution (50 µg/mL) was physisorbed to the surface of the flask or bottle for 1 hour at room temperature, followed by rinsing and drying. A 1 mm thick PDMS etch mask was inserted into the flask or bottle and pressed against the walls. This was placed inside the plasma asher and exposed to oxygen plasma at 100 W for 2 minutes. Following plasma ablation, primary rat hepatocytes were seeded and cultured overnight. The cells were stained with 3-(4,5-dimethylthiazol-2-yl)-2,5-diphenyltetrazolium bromide (MTT) at 0.5 mg/mL which is cleaved into a visible product in viable cells for imaging.

Example 6—a Miniaturized, Multiwell Human Liver Tissue Model

The system is comprised of primary human hepatocytes organized in micropatterned colonies surrounded by supportive stromal cells. Model utility is demonstrated via gene expression profilings, phase I/II metabolism, canalicular transport, secretion of liver-specific products, and susceptibility to hepatotoxins.

Elastomeric stencils were used to miniaturize and characterize human liver tissue in an industry-standard multiwell format. In order to micropattern all wells simultaneously, the assembly was sealed against a polystyrene plate. Collagen-I was adsorbed to exposed polystyrene, the stencil was removed, and a 24-well PDMS 'blank' was applied. Co-cultures were 'micropatterned' by selective adhesion of primary hepatocytes to collagen-coated domains, which were then surrounded by supportive murine 3T3-J2 fibroblasts.

The diameter of through-holes in the stencils determined the size of collagen-coated domains and thereby the balance of homotypic (hepatocyte/hepatocyte) and heterotypic (hepatocyte/fibroblast) interactions in the microscale tissue. We varied collagen island diameter over several orders-of-magnitude and observed that hepatocyte clustering consistently improved liver-specific functions when compared to unorganized cultures. Furthermore, hepatocyte functions were maximal for the configuration containing ~500 µm islands with ~1200 µm center-to-center spacing. These findings are consistent with our rodent data in that 3T3 fibroblasts were able to stabilize hepatocyte functions across both species; however, human hepatocytes were more dependent on homotypic interactions than rat hepatocytes. Thus, the microscale human liver tissue developed and characterized herein represents 24-well plates with each well containing ~10,000 hepatocytes organized in 37 colonies of 500 µm diameter and surrounded by 3T3-J2 fibroblasts (micropatterned co-cultures), for a total of 888 repeating hepatic microstructures per plate. The microscale architecture remained stable for several weeks in culture which enabled microscopic tracking of individual hepatocyte islands for weeks.

Figure 12A:
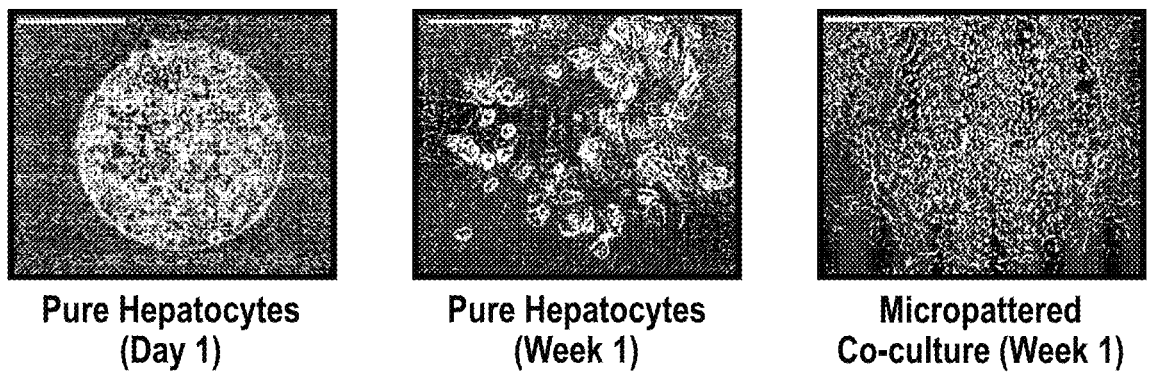
FIGS. 12A-12D depict the functional characterization of microscale liver tissues.
Figure 12B:
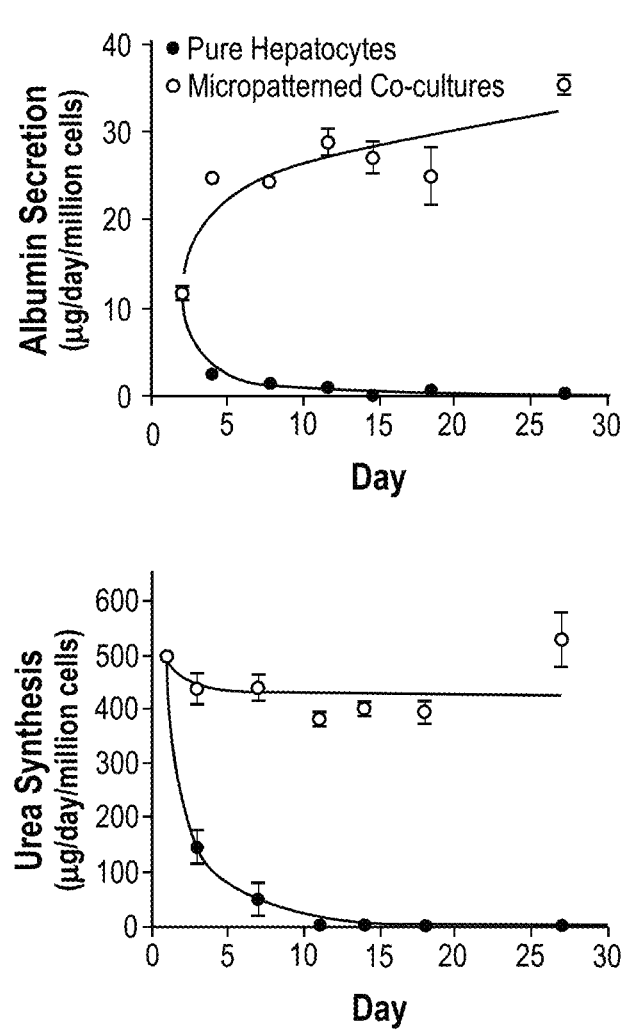

In order to qualitatively assess the stability of micropatterned co-cultures, hepatocyte morphology was monitored over time and found to be maintained for the duration of the cultures, typically 4-6 weeks (FIG. 12a). Pure hepatocytes, on the other hand, rapidly spread out on the culture surface to adopt a fibroblastic morphology that is characteristic of a loss of phenotypic functions[17, 32]. To quantitatively assess the stability of liver-specific functions in micropatterned co-cultures, we measured albumin secretion and urea synthesis as surrogate markers of protein synthesis and nitrogen metabolism, respectively (FIG. 12b). Albumin secretion took 3-6 days to reach steady-state levels following hepatocyte isolation, whereas a monotonic decline was confirmed in unorganized pure hepatocyte cultures. Recovery of albumin secretion over time is well-established in virtually all culture models that purport to stabilize hepatic functions. Such recovery periods are consistent with the hypothesized 'trauma' of isolation, reported to be more pronounced for some functions (i.e. albumin secretion, CYP3A4 expression) than others. In contrast, the levels of urea synthesis in micropatterned co-cultures were found to stabilize immediately, whereas levels declined rapidly in pure hepatocyte cultures.

Figure 12C:
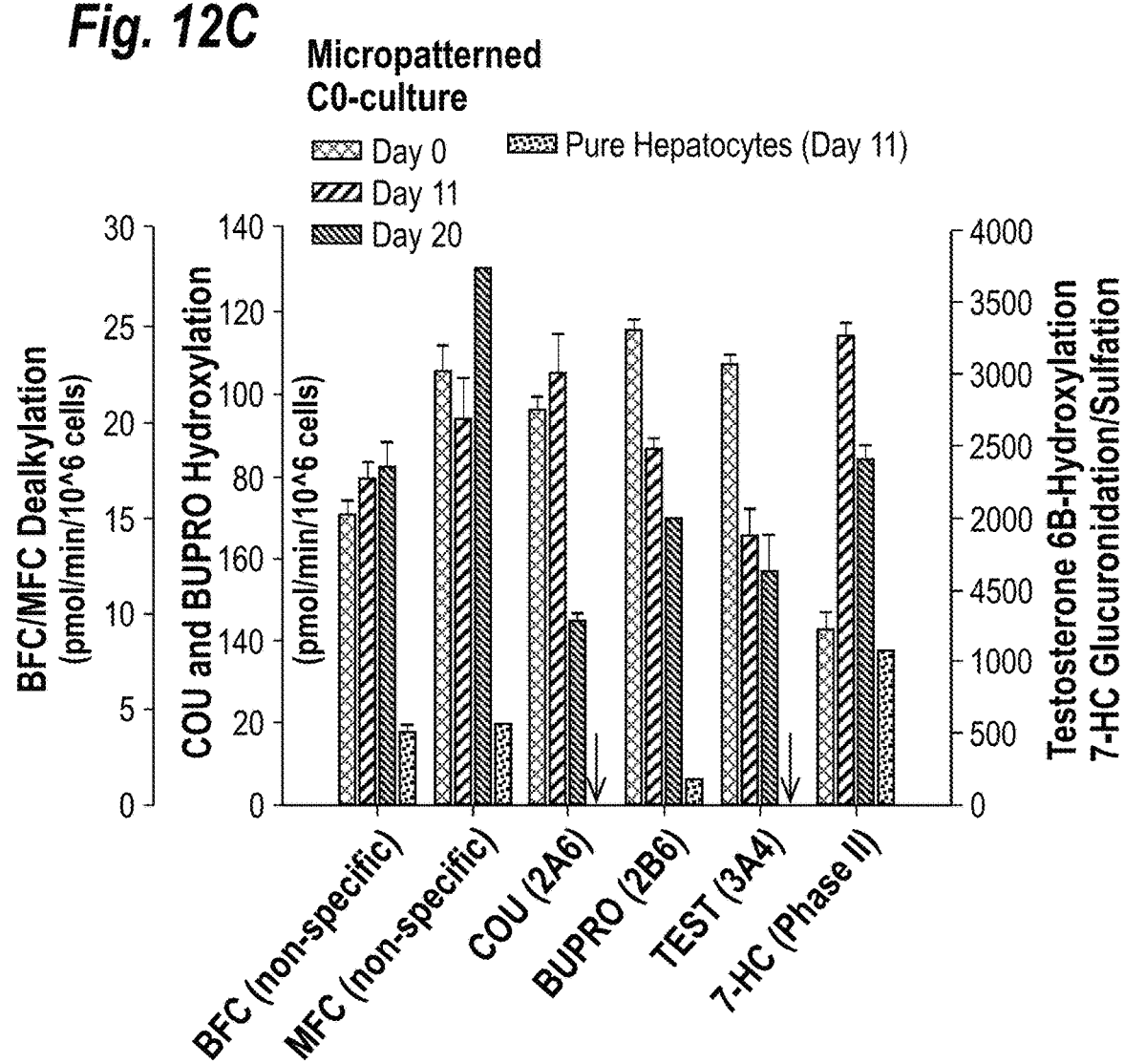
Figure 12D:
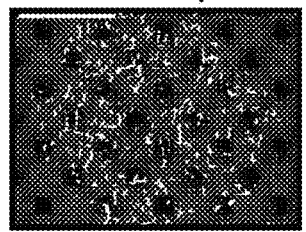

In order to assess the utility of micropatterned co-cultures for drug metabolism studies, cytochrome P450 (CYP450) activity, phase II conjugation, and canalicular transport was characterized. CYP450 activity in micropatterned co-cultures was assessed over several weeks using both fluorometric substrates well-suited for high-throughput screening and isoenzyme-specific probe substrates requiring chromatographic separation of metabolites. Activities of several major CYP450 isoenzymes (CYP2A6, 2B6, 3A4) were retained well (>50% of fresh hepatocyte levels) for several weeks in un-induced micropatterned co-cultures (FIG. 12c). Such 'baseline' P450 activity in micropatterned co-cultures is critical for evaluation of metabolism-mediated mechanisms of toxicity, and is in contrast to immortalized hepatic cell lines (i.e. HepG2, Fa2N-4) which lack baseline levels of several P450s including CYP3A4. Marked loss of CYP450 activities (<25% of fresh hepatocyte levels) was confirmed in pure hepatocyte cultures. Phase II activities were also retained for several weeks in un-induced micropatterned co-cultures as determined by the conjugation of 7-hydroxycoumarin with glucuronide and sulfate moieties. Lastly, active phase III transport was observed in micropatterned co-cultures as evaluated by the intracellular cleavage and transport of a fluorometric substrate, 5-(and-6)-carboxy-2', 7'-dichlorofluorescein diacetate (CDF) into the bile canaliculi between hepatocytes (FIG. 12d). With retention of their polarized phenotype, hepatocytes in micropatterned co-cultures may be useful for evaluating the hepatobiliary disposition of pharmaceutical compounds.

In order to obtain a more global perspective, the microscale tissues were gene expression profiled over the span of several weeks. Prior to extraction of hepatocyte RNA, fibroblasts were removed via selective trypsinization (~95% purity, see supplemental methods online). The ability to obtain purified hepatocyte RNA from micropatterned co-cultures is enhanced by clustering via micropatterning and is advantageous for genome-wide analyses (e.g. toxicogenomics). Gene expression profiles of hepatocytes in this platform were compared to gene expression in several models, which included: a) all cell types of the human liver immediately after tissue disruption but prior to hepatocyte purification (universal mixture of all cells or UMIX); b) freshly isolated pure hepatocytes in suspension (day 0) widely used as starting point controls for in vitro studies; and c) unorganized pure hepatocyte monolayers 1 week after plating as a model of deteriorating functions. In this study, global scatter plots were utilized coupled with linear regression analysis to compare gene expression in the aforementioned liver models.

Figure 13A:
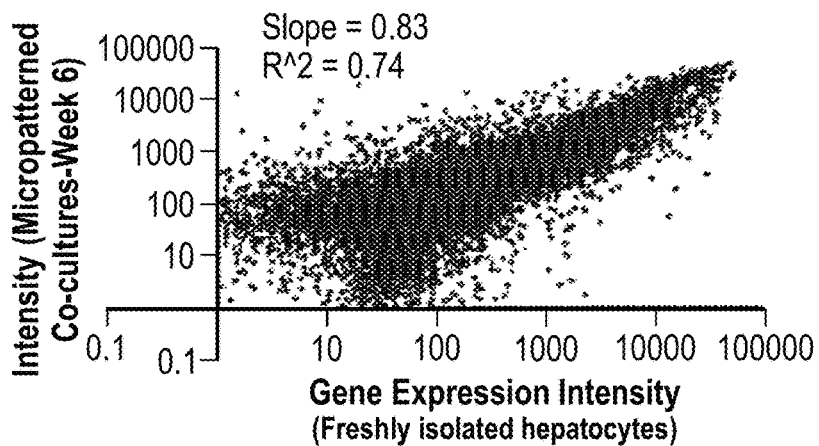
FIGS. 13A-13F depict gene expression profiling of hepatocytes in microscale liver tissues. Global
Figure 13B:
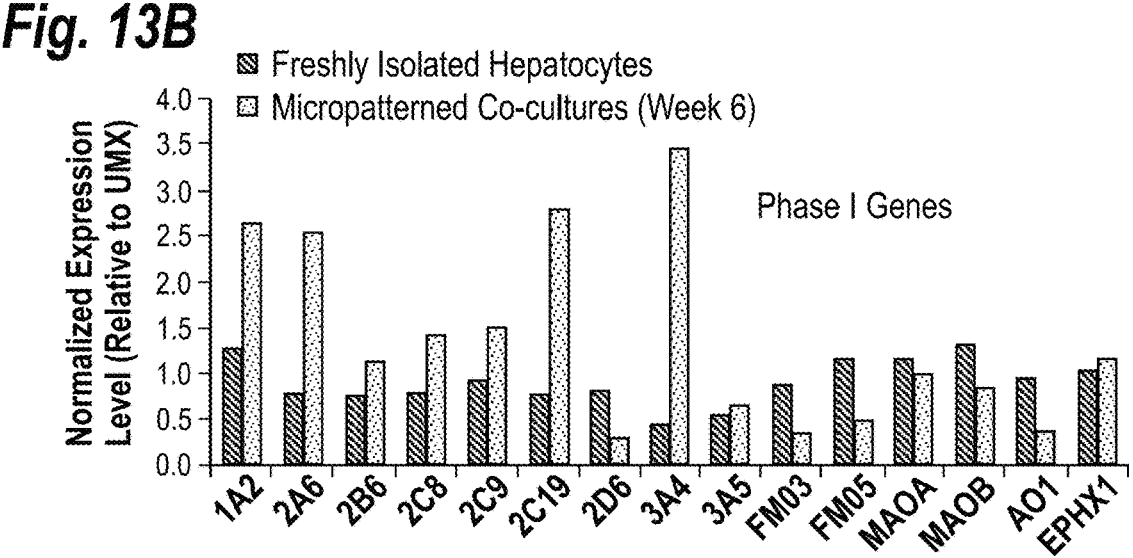
Figure 13C:
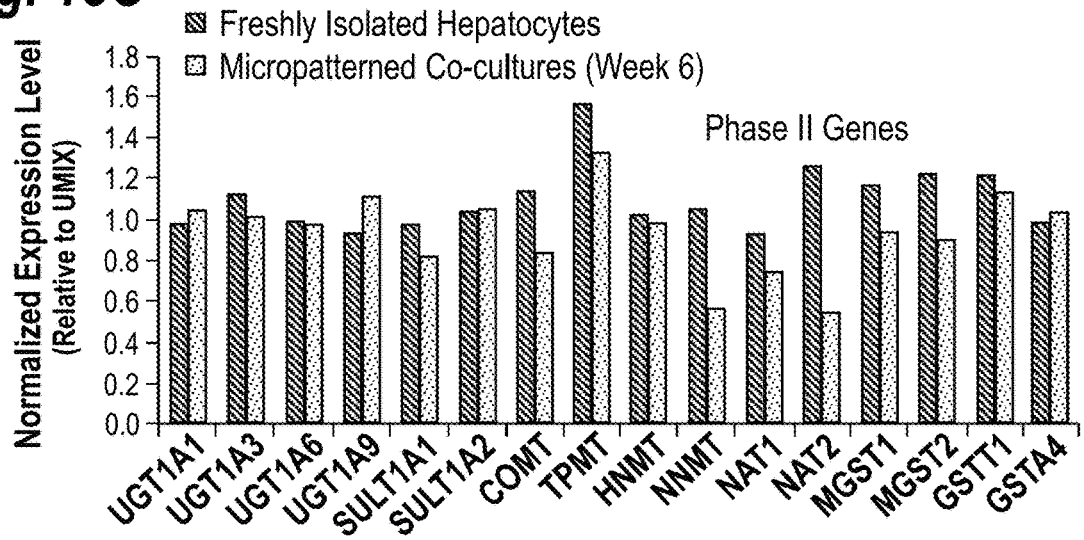

Overall, these expression profiling experiments showed that hepatocytes in micropatterned co-cultures were stable for 4-6 weeks as indicated by high levels of expression of liver-specific genes (relative to fresh controls and pure hepatocytes) relevant for evaluating drug metabolism and toxicity in vitro (i.e. Phase I, II, III, nuclear receptors, liver-enriched transcription factors). Specifically, global gene expression analysis revealed a positive correlation ($R^2$ between 0.7-0.8) between expression intensities in hepatocytes purified from micropatterned co-cultures (up to 6 weeks) and intensities in fresh controls, which included all cell types of the liver as well as purified fresh hepatocytes in suspension (FIG. 13a). Examination of drug metabolism pathways in these global data sets showed that all liver-specific CYP450 (32 total) and Phase II (59 total) genes that were found on the microarray were expressed at statistically significant levels in hepatocytes from micropatterned co-cultures as old as 6 weeks, long after pure hepatocytes had lost phenotypic functions (~1 week) (FIG. 13b-c). The levels of CYP450 transcripts in micropatterned co-cultures relative to fresh hepatocytes were found to be highly variable across different donors (i.e. ~44% to 350% for CYP3A4). These findings are consistent with literature indicating high variability of gene expression profiles in freshly-isolated human hepatocytes due to factors that may alter physiologic levels of gene expression (i.e. drug-mediated enzyme induction in donor, isolation procedures, storage/shipment conditions). Additionally, reports that mRNA levels do not always correlate quantitatively with enzymatic activity were confirmed. Measurements of enzymatic activities in micropatterned co-cultures (FIG. 12c) showed much greater similarity to fresh levels than corresponding comparisons of mRNA levels.

Figure 13D:
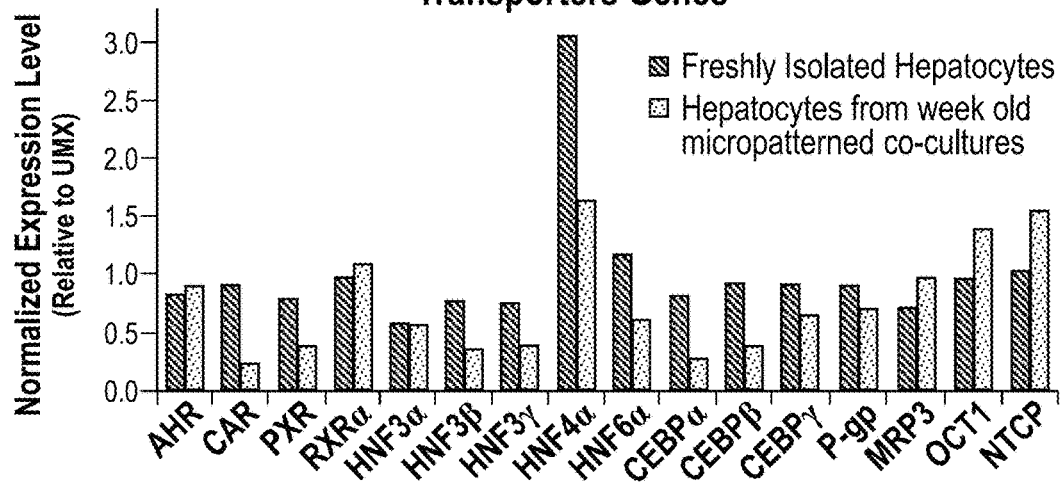
Figure 13E:
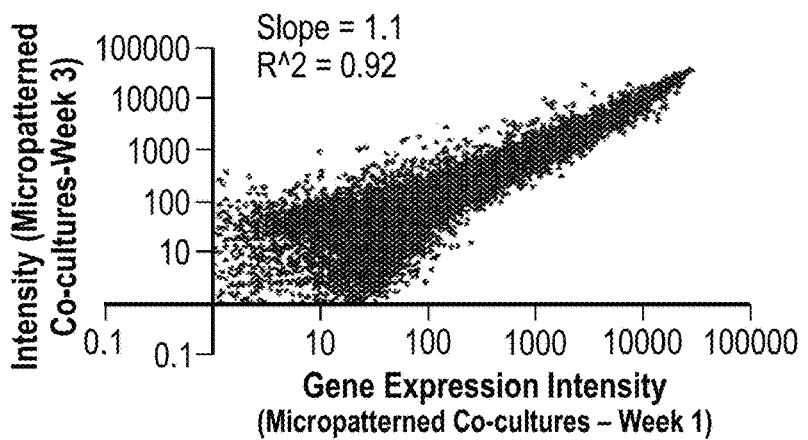
Figure 13F:
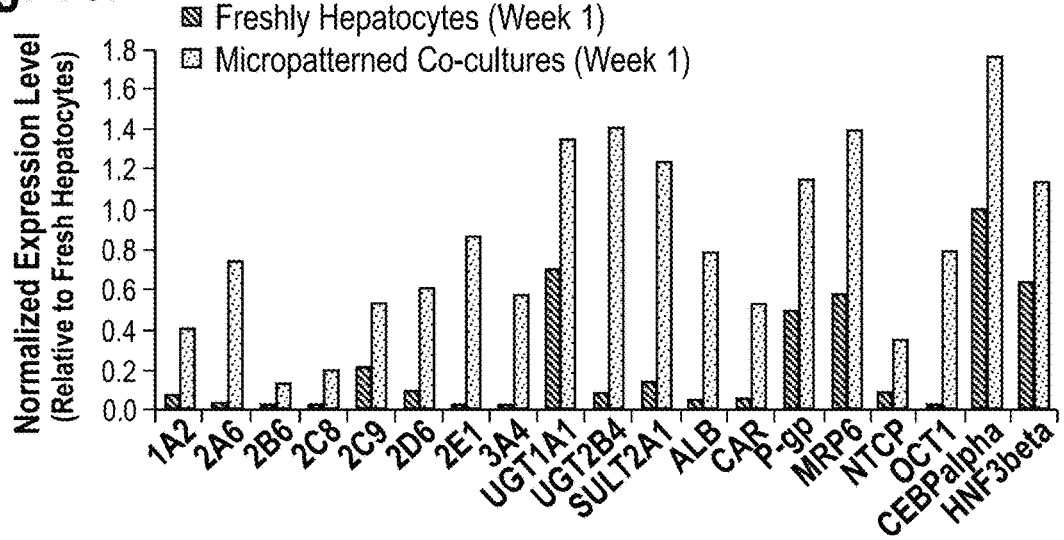

In addition to Phase I and II drug metabolism genes, the gene expression levels of several other classes of genes relevant in evaluating drug disposition were also analyzed, which included: nuclear receptors (NR) that can modulate the expression of drug metabolism enzymes following exposure of hepatocytes to endogenous and exogenous stimuli; liver-enriched transcription factors (LETF) which regulate broad classes of hepatic functions; and influx and efflux transporters. Several important genes were found from these classes which were expressed at statistically significant levels in micropatterned co-cultures (up to 6 weeks) (FIG. 13d). Next, the transcriptome of hepatocytes in micropatterned co-cultures were examined over several weeks and found to be relatively stable ($R^2$=0.92, Slope=1.1) when comparing week 1 to week 3 (FIG. 13e). Lastly, marked loss of liver-specific transcripts were confirmed in pure hepatocytes after only 1 week of culture as compared to our platform and fresh controls (FIG. 13f). For instance, 47% of CYP450 genes (32 total) in 1 week old pure hepatocytes were expressed at levels 5% or lower of those in fresh hepatocytes, whereas expression levels of CYP450 genes were much better retained in micropatterned co-cultures after 1, 3 and 6 weeks in vitro.

Figure 14A:
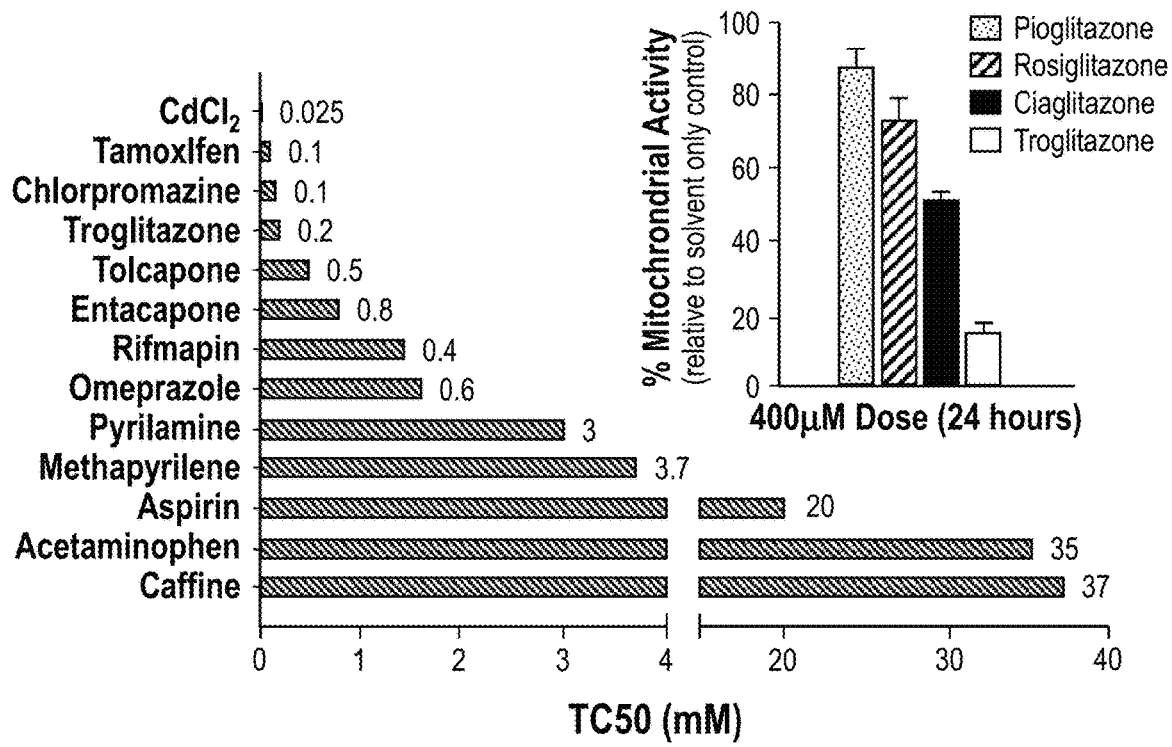
FIGS. 14A and 14B demonstrate the utility of microscale liver tissues for toxicity screening.
Figure 14B:
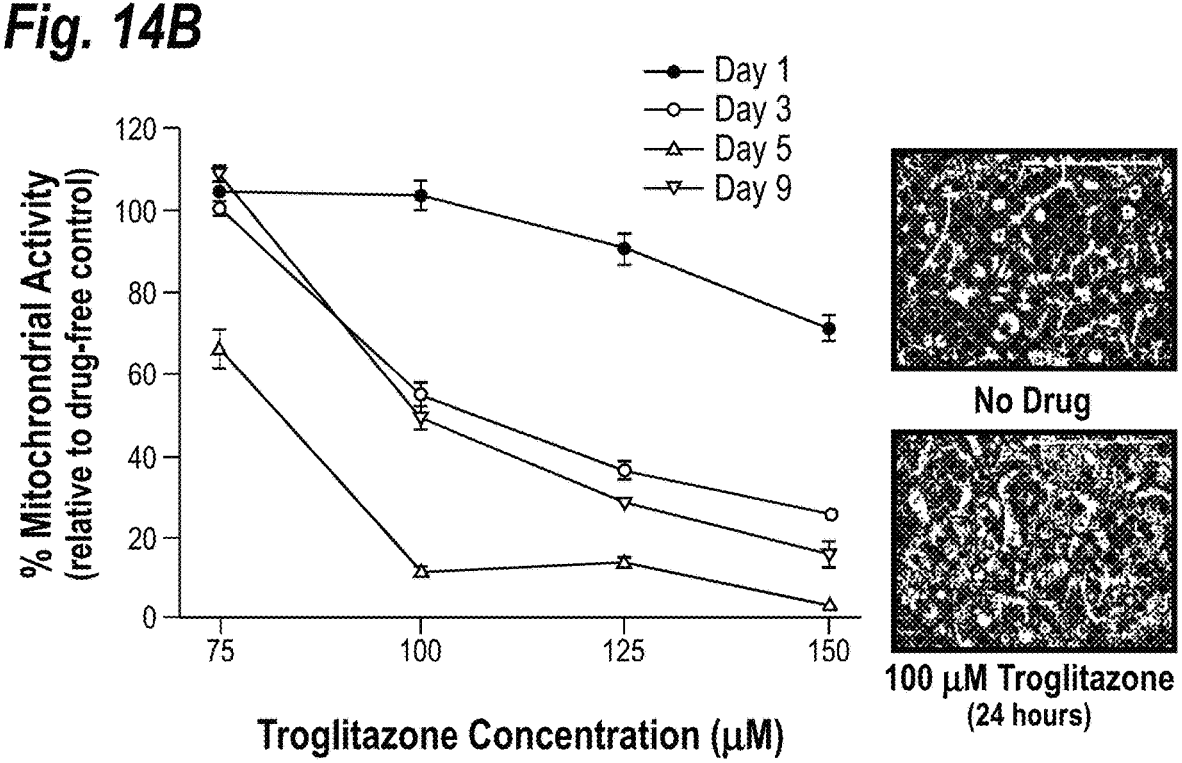
Figure 15A:
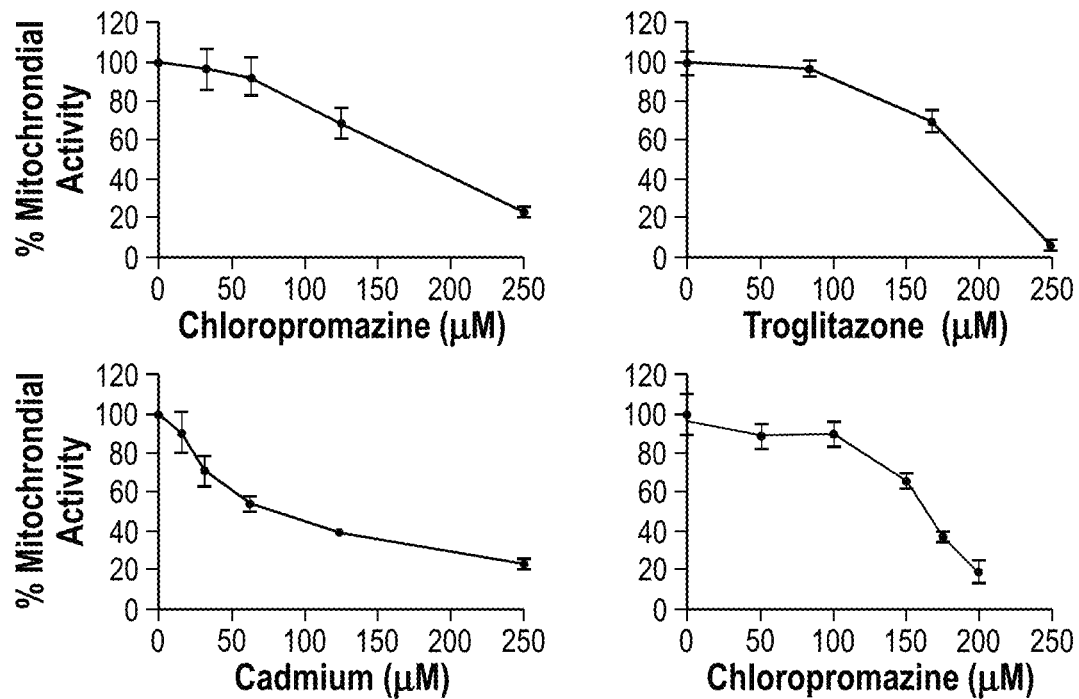
FIGS. 15A-15C depict case studies demonstrating utility of microscale human liver tissues in drug development.
Figure 15B:
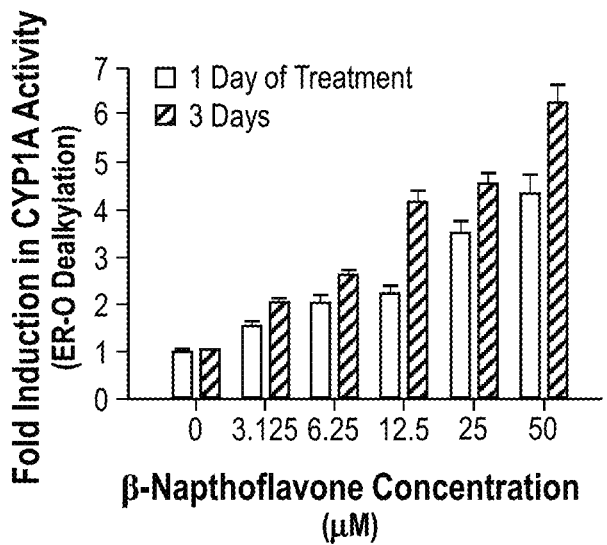
Figure 15C:
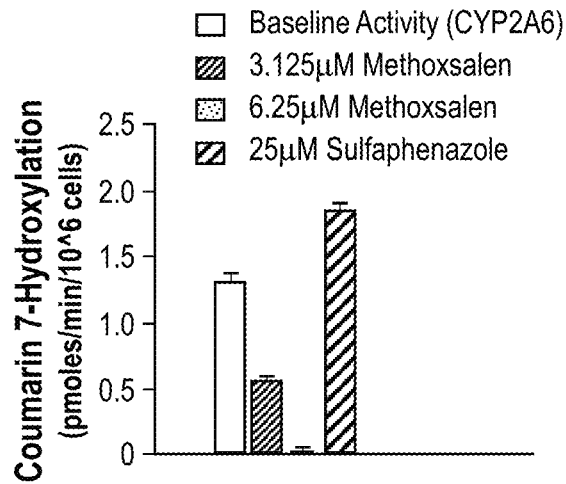

In order to assess the utility of micropatterned co-cultures for toxicity screening, the acute and chronic toxicity of model hepatotoxins was quantified. Compounds were characterized by their TC50, defined as the concentration which produced 50% reduction in mitochondrial activity after an acute (24 hours) exposure (FIG. 14a). Relative toxicity corresponded to relative hepatotoxicity of these compounds in humans. For example, the TC50 for cadmium was three orders-of-magnitude lower than the TC50 values for aspirin and caffeine. By comparing compounds within a given class, the thiazolidinediones, it is demonstrated that troglitazone (an oral hypoglycemic withdrawn from the market due to hepatotoxicity) is much more acutely toxic than its structural analogues, rosiglitazone and pioglitazone, which have been shown clinically to have a larger margin of safety and are now approved by the FDA. The relative toxicity of entacapone and tolcapone (drugs for Parkinson's disease) was observed in micropatterned co-cultures to be also consistent with clinical findings. Established mechanisms of toxicity could also be inferred from toxicity profiles in our platform. For instance, cadmium showed a relatively linear toxic profile while acetaminophen exhibited a toxicity 'shoulder' consistent with glutathione depletion as proposed elsewhere (FIG. 15). Establishment of liver tissue that is stable over several weeks is crucial for evaluating chronic toxicity due to repeated exposures. In FIG. 14b is demonstrated the dose and time-dependent toxicity of Troglitazone. Concentrations that were not lethal at 24 hours caused extensive cell death after prolonged exposure. Rosiglitazone, on the other hand, showed minimal chronic toxicity even after 9 days of exposure (up to 200 µM). Furthermore, severe morphologic changes in hepatocytes were readily observed prior to cell death, allowing the potential to detect sub-lethal toxicity using microscopic imaging at concentrations lower than those required for frank cell death.

Figure 16A:
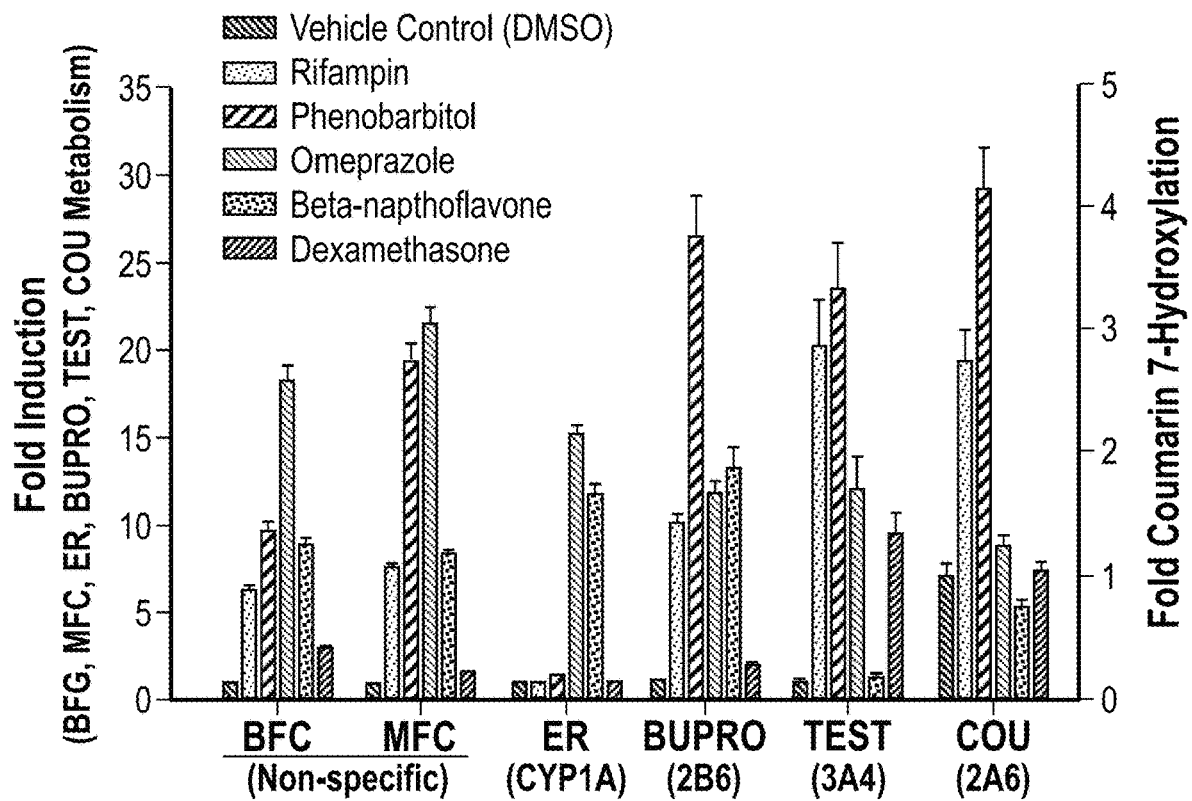
FIGS. 16A-16D demonstrate the utility of microscale liver tissues for evaluating drug-drug interactions.
Figure 16B:
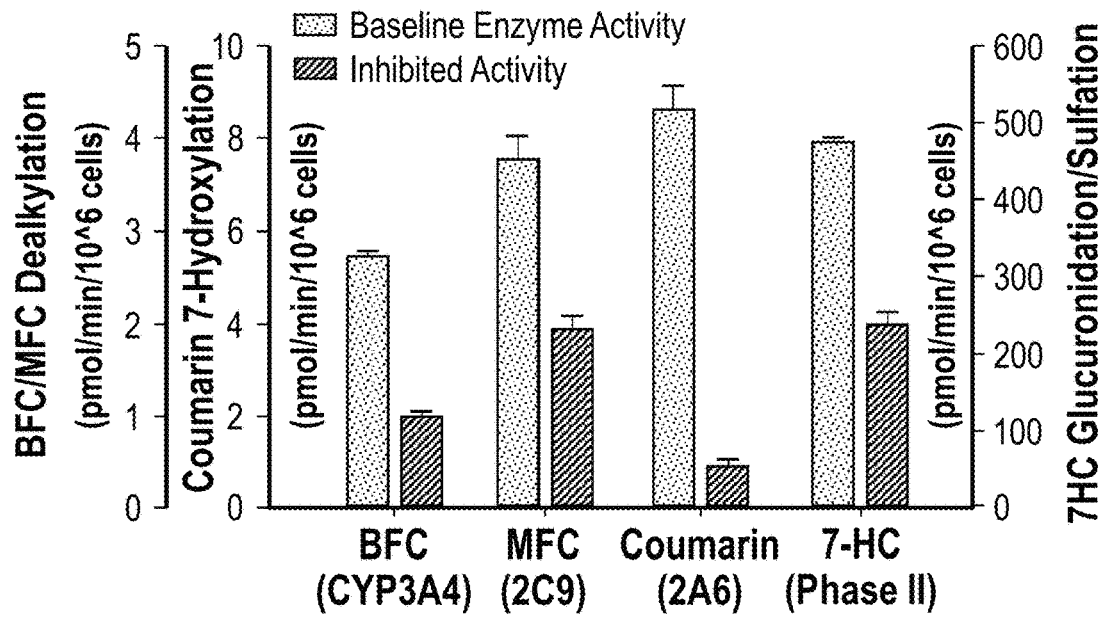

The induction and inhibition of drug metabolism enzymes (i.e. CYP450) typically underlie drug-drug interactions which can lead to serious pharmacological and/or toxicological consequences in the clinic. The induction of CYP450 activity in micropatterned co-cultures was demonstrated using prototypic clinical inducers and both fluorometric and conventional CYP450 substrates (FIG. 16a). The induction profiles obtained correlated well with published in vitro and in vivo studies. For instance, CYP1A, known to be regulated by AhR (aryl hydrocarbon receptor), was strongly induced (>10-fold) only when micropatterned co-cultures were incubated with AhR activators, Omeprazole and β-Naphthoflavone. On the other hand, CYP2A6 was induced strongly (>3-fold) in micropatterned co-cultures only by PXR (pregnane X receptor) activator, Rifampin, and PXR/CAR (constitutive androstane receptor) activator, Phenobarbital. β-Naphthoflavone had a suppressive effect (20-40%) on CYP2A6 activity, which is consistent with studies conducted in short-term primary human hepatocyte cultures. While both CYP2B6 and CYP3A4 were strongly induced (>10-fold) by Rifampin, Phenobarbital and Omeprazole, only CYP3A4 was induced by the synthetic glucocorticoid, Dexamethasone. In addition to CYP450 induction, we found that activities of CYP450 and Phase II enzymes in micropatterned co-cultures could be inhibited with specific inhibitors (FIG. 16b).

Figure 16C:
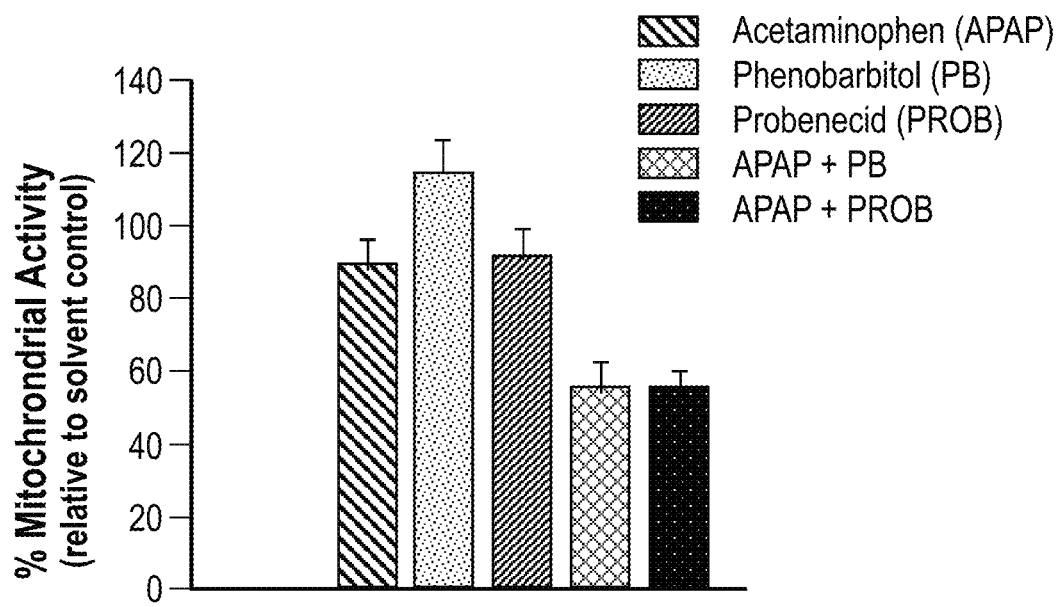
Figure 16D:
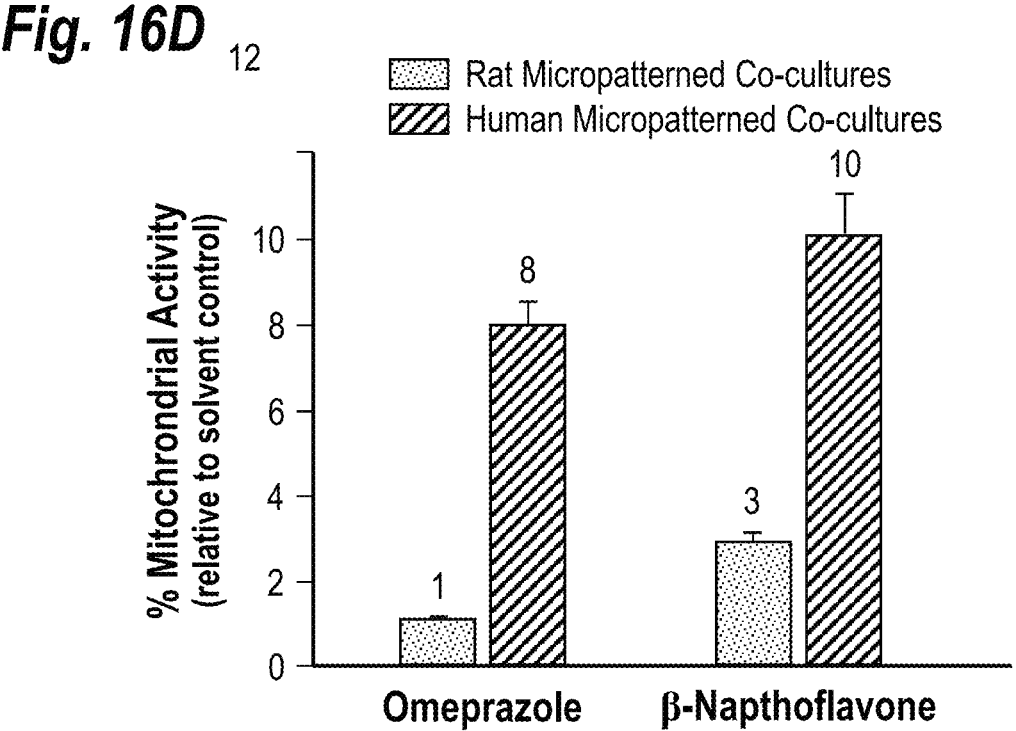

Modulation of CYP450 activities depends on both the dose and time of exposure to compounds. In FIG. 15, we show that β-Naphthoflavone induced CYP1A2 activity in a dose and time-dependent manner in micropatterned co-cultures, while Methoxsalen, a potent inhibitor of CYP2A6[21], showed dose-dependent inhibition of CYP2A6 activity. To demonstrate utility of our platform for the study of drug-drug interactions using toxicity as an endpoint, we utilized acetaminophen (APAP), a widely utilized analgesic that can be converted into a toxic metabolite by CYP450 enzymes (Phase I) and detoxified via glucuronidation (Phase II). Micropatterned co-cultures were first treated with either Phenobarbital to induce CYP450 levels or Probenecid to inhibit glucuronidation. Incubation of these treated tissues with APAP led to increased toxicity over controls (FIG. 16c), presumably due to modulation of Phase I and II pathways. However, other effects (i.e. changes in transporter levels) of Phenobarbital and Probenecid on hepatocytes cannot be ruled out. Nonetheless, the APAP-Phenobarbital and APAP-Probenecid interactions we observed in vitro with micropatterned co-cultures are consistent with interactions reported in clinical settings. Lastly, we demonstrated species-specific differences in CYP450 induction by comparing the responses of micropatterned co-cultures created using primary human or rat hepatocytes. Omeprazole, reported to be a more effective inducer of human CYP1A2 than rat CYP1A[58], was 8-fold more effective in human over rat models (FIG. 16d). Retention of species-specific differences in human and animal liver tissue models is critical for extrapolation of in vitro metabolism and toxicity data to in vivo trends.

An advantageous feature of our platform is its modular design in that various liver or non-liver derived stromal cells can be used to surround hepatocyte colonies to form microscale tissues. We chose 3T3 (sub-clone J2) fibroblasts because of their ready availability, ease of propagation, lack of liver-specific gene expression (albumin, P450 activity), and evidence showing that this cell line can induce high levels of liver-specific functions. Nonetheless, to demonstrate versatility of our platform, we co-cultivated micropatterned human hepatocytes with the non-parenchymal fraction of the human liver and also observed stabilization of hepatic functions, though not to similar levels or duration as in co-cultures with 3T3 fibroblasts (data not shown).

Figure 17:
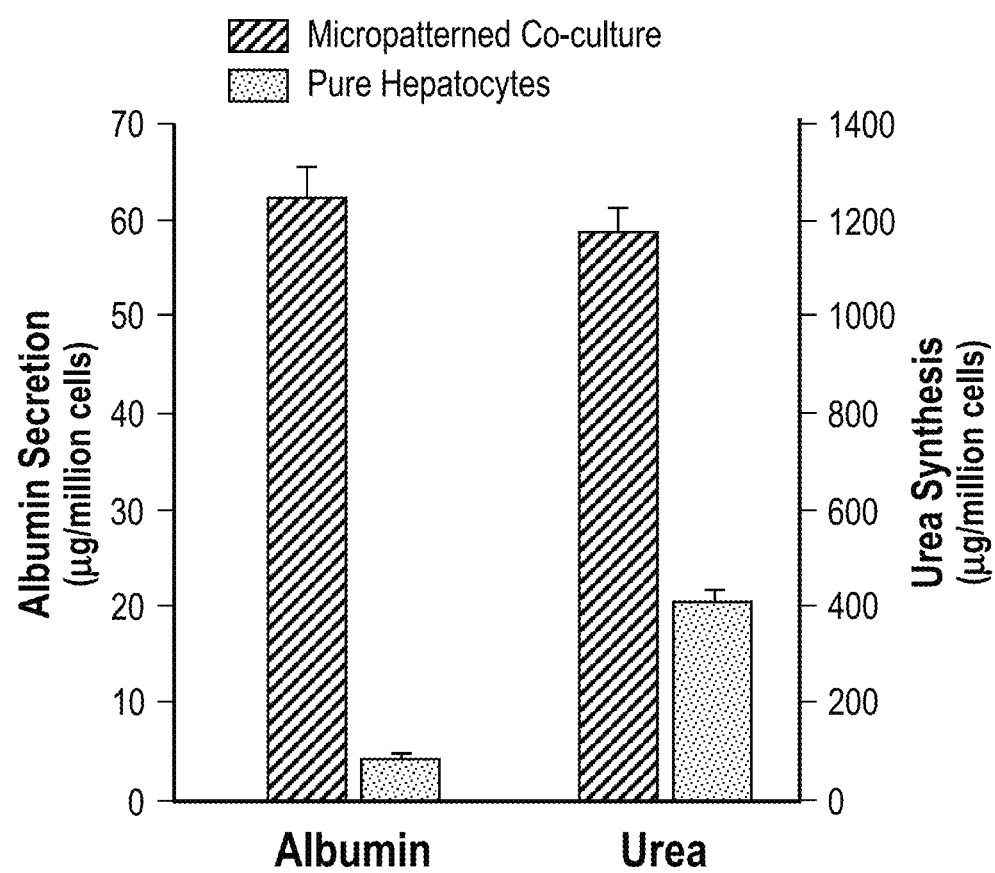
FIG. 17 provides a functional comparison of culture models created using cryopreserved human hepatocytes. Plateable (or inducible) cryopreserved hepatocytes were thawed and plated according to manufacturer's instructions (Celsis In Vitro Technologies, Baltimore, Md.). Cumulative albumin and urea secretion over the course of two weeks is shown for micropatterned co-cultures (500 µm circular hepatocyte islands with 1200 µm center-to-center spacing) and micropatterned pure hepatocytes.

We demonstrated that micropatterned clusters of pure human hepatocytes outperformed their randomly distributed counterparts by several-fold, consistent with reports that confluent hepatocyte cultures retain liver-specific functions better than sparse cultures, partly through cadherin interactions. Subsequent introduction of non-parenchymal cells further enhanced hepatocyte functions and longevity of the liver tissues. Thus, our optimized micropatterned co-cultures use an order-of-magnitude fewer hepatocytes (10K vs. 200K) and maintain phenotypic functions for a longer time than conventional pure cultures (weeks vs. days) in similar multiwell formats. Furthermore, we explored many hepatocyte sources. In our platform, we observed induction of liver-specific functions in fresh hepatocytes across donors of different age groups, genders and medical histories. Nonetheless, due to limited availability of fresh cells, we demonstrated successful incorporation of cryopreserved human hepatocytes into micropatterned co-cultures (FIG. 17) which allows the flexibility to generate tissues on demand.

Figure 18A:
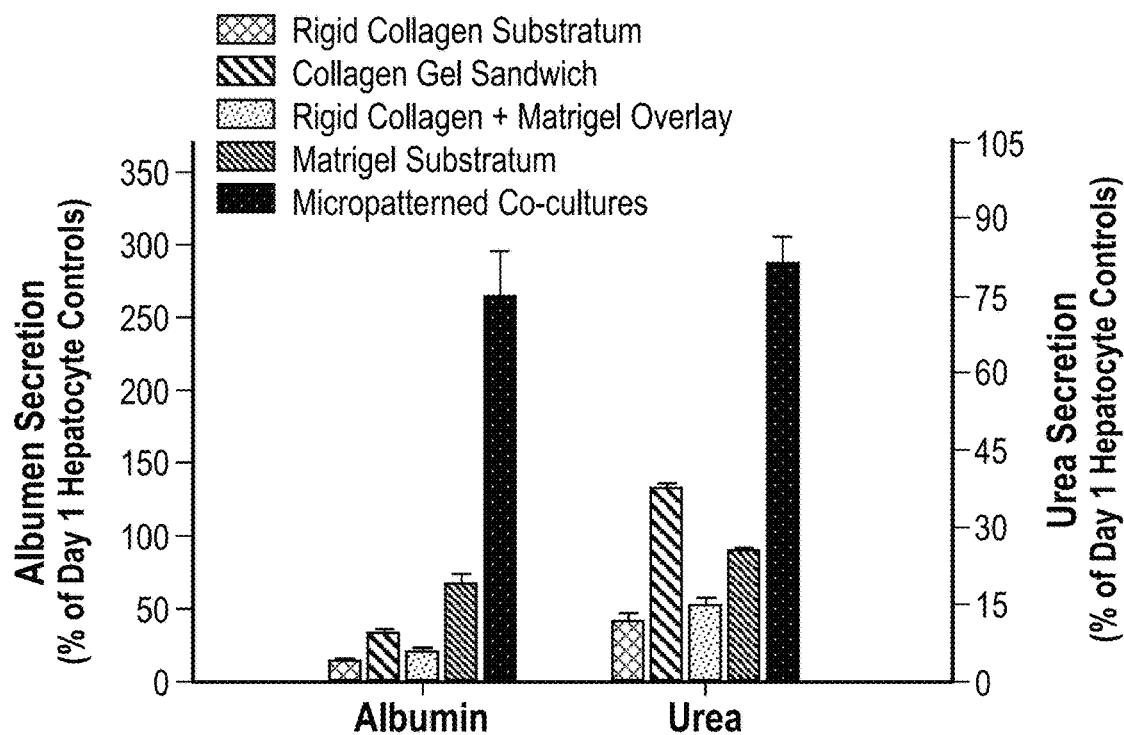
FIGS. 18A-18B provide a functional comparison of microscale human liver tissues to well-established in vitro liver models utilized in the pharmaceutical industry. Cultures were created in multi-well plates (12- and 24-well formats) and compared in different formats: rigid type-I collagen coating, type-I collagen gel sandwich, rigid collagen coating with Matrigel overlay, Matrigel gel substratum, and micropatterned co-cultures (500 µm circular hepatocyte islands with 1200 µm center-to-center spacing).
Figure 18B:
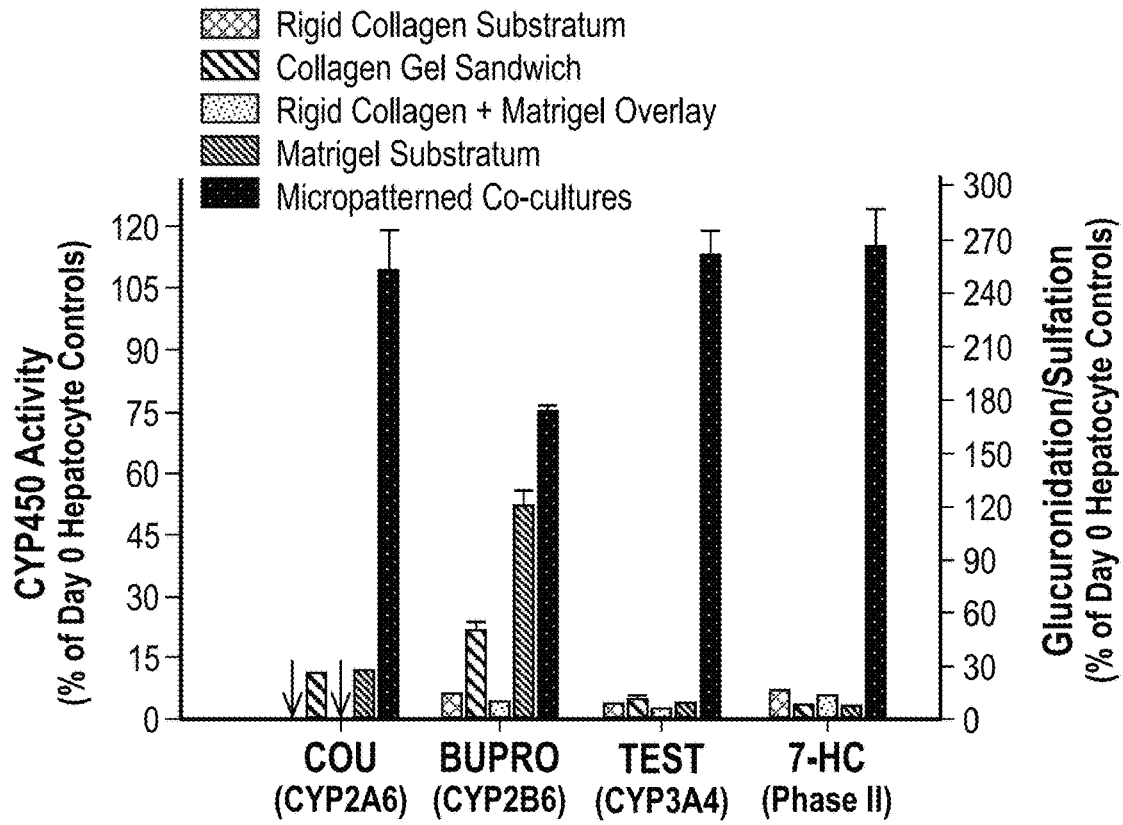

Hepatocyte culture models typically employed in the pharmaceutical industry rely on manipulating the extracellular microenvironment of hepatocytes with Matrigel and/or collagen (i.e. Matrigel overlay, collagen gel sandwich culture). When utilized with near confluent (80-100%) monolayers of hepatocytes, these models allow better retention of hepatocyte cytoarchitecture (i.e. bile canaliculi, tight junctions) and activity of specific CYP450 enzymes for a few more days (~1 week) than that seen in monolayers on rigid collagen. However, studies have shown that cell-cell contacts (homotypic and heterotypic), more than the extracellular matrix configuration or composition, play a critical role in maintaining phenotypic functions of primary human hepatocytes in vitro. Primary rat hepatocytes, on the other hand, functionally respond better to extracellular matrices of different compositions and topologies. Our own studies with primary human hepatocytes confirmed the data reported in the literature (FIG. 18). Specifically, we compared micropatterned co-cultures to culture models routinely utilized for evaluating drug disposition in vitro. In our hands, we observed that extracellular matrix modifications improved specific hepatic functions, including CYP450 isoenzyme activities (up to 22% of fresh levels after 1 week of culture). However, liver-specific functions were better retained in micropatterned co-cultures as compared to the conventional models (>75% of fresh levels after several weeks of culture). Furthermore, micropatterned co-cultures do not rely on matrix gels, which can be difficult to scale down to 96-well (or smaller) formats.

Several other in vitro models of the liver that utilize '3D' tissues (aggregate-based) and/or continuous perfusion have been proposed in the literature. Many of these strategies were initially developed for applications in cell-based therapies (i.e. tissue engineering) where the challenges are often around scale-up; however, a few have been scaled-down for utility in drug screening applications. 3D architecture is indeed likely to be critical to therapeutic applications of liver tissue; however, it can introduce challenges when applied to high-throughput applications that stem from limited in situ observation of cells with conventional microscopic techniques and nutrient transport limitations. Nutrient transport limitations can be overcome by the inclusion of convective transport in the form of flowing medium. Nonetheless, the inclusion of a flow circuit for each well in a high-throughput screening format introduces complexities in liquid handling (pumps rather than liquid dispensers) and larger fluid volumes that require larger quantities of novel compounds. As a result, static 2D monolayer systems (confluent monolayers, collagen sandwich or Matrigel overlay) are currently widely favored in industrial settings. In this study, we show that the phenotypic functions of primary human hepatocytes can be maintained remarkably well in a static, 2D platform. These micropatterned co-cultures can be mapped seamlessly to existing laboratory protocols including robotic fluid handling, in situ microscopy, and colorimetric/fluorescent plate-reader assays.

In conclusion, microtechnology was utilized to fabricate and miniaturize human liver tissue that can be used for high-content cell-based assays in preclinical phases of drug development. We anticipate that the adoption of microscale liver tissues for ADME/Tox screening will be facilitated by the long-term retention of human hepatocyte functions as well as the ability to seamlessly integrate the multi-well, 2D tissues into the existing technological infrastructure. Such a platform has potential to reduce development costs, increase likelihood of clinical success, and reduce the risk for patient exposure to unsafe drugs. In the future, in vitro tissue models with precisely defined microenvironments may find utility in many other arenas that could benefit from realistic models of human tissue biology.

Micropatterning of Collagen

Elastomeric Polydimethylsiloxane (PDMS) stencil devices, consisting of thick-membranes (300 µm) with through-holes (500 µm with 1200 µm center-to-center spacing) at the bottom of each well of a 24-well mold were manufactured by Surface Logix, Inc (Brighton, Mass.). Stencil devices were first sealed (via gentle pressing) to tissue culture treated polystyrene omnitrays (Nunc, Rochester, N.Y.), then each well was incubated with a solution of type-I collagen in water (100 µg/mL) for 1 hour at 37° C. Purification of collagen from rat-tail tendons was previously described. The excess collagen solution in each well was aspirated, the stencil was removed and a PDMS "blank" (24-well mold without stencil membranes) was applied. Collagen-patterned polystyrene was stored dry at 4° C. for up to 4 weeks. In some cases, micropatterned collagen was fluorescently labeled via incubation (1 hour at room temperature) with Alexa Fluor® 488 carboxylic acid, succinimidyl ester (Invitrogen, Carlsbad, Calif.) dissolved in phosphate buffered saline (PBS) at 20 µg/mL. For experiments in Supplemental FIG. 1 online, collagen was micropatterned in various dimensions on glass substrates using conventional photolithographic techniques as described previously.

Hepatocyte Isolation and Culture

Primary rat hepatocytes were isolated from 2-3-month old adult female Lewis rats (Charles River Laboratories, Wilmington, Mass.) weighing 180-200 g. Detailed procedures for rat hepatocyte isolation and purification were previously described[79]. Routinely, 200-300 million cells were isolated with 85%-95% viability and >99% purity. Hepatocyte culture medium consisted of Dulbecco's Modified Eagle's medium (DMEM) with high glucose, 10% (v/v) fetal bovine serum, 0.5 U/mL insulin, 7 ng/mL glucagon, 7.5 µg/mL hydrocortisone, and 1% (v/v) penicillin-streptomycin. Primary human hepatocytes were purchased in suspension from vendors permitted to sell products derived from human organs procured in the United States of America by federally designated Organ Procurement Organizations. Hepatocyte vendors included: In Vitro Technologies (now part of Celsis, Baltimore, Md.), Cambrex Biosciences (now part of Lonza, Walkersville, Md.), BD-Gentest (Woburn, Mass.), ADMET Technologies (Durham, N.C.), CellzDirect (Pittsboro, N.C.) and Tissue Transformation Technologies (now part of BD-Gentest, Edison, N.J.). All work was done with the approval of COUHES (Committee on use of human experimental subjects). Upon receipt, human hepatocytes were pelleted via centrifugation at 50×g for 5 min (4° C.). The supernatant was discarded, cells were re-suspended in hepatocyte culture medium, and viability was assessed using trypan blue exclusion (typically 70-90%). Liver-derived nonparenchymal cells, as judged by their size (<10 µm diameter) and morphology (non-polygonal), were consistently found to be less than 1% in these preparations.

Hepatocyte-Fibroblast Co-Cultures

In order to create micropatterned co-cultures, hepatocytes were seeded on collagen-patterned substrates, resulting in a hepatocyte pattern due to selective cell adhesion. The cells were washed with medium 2 hours later to remove unattached cells (~10,000 adherent hepatocytes in 37 collagen-coated islands) and incubated in hepatocyte medium overnight. 3T3-J2 fibroblasts were seeded (30,000 total) in fibroblast medium 12-24 hours later to create co-cultures.

Fibroblast to hepatocyte ratio was estimated via a hemocytometer to be 4 to 1 once the fibroblasts reached confluency in cocultures and their growth was contact-inhibited. Culture medium was replaced to hepatocyte medium 24 hours after fibroblast seeding and subsequently replaced daily (300 μL per well in 24-well format). For cultures, hepatocytes were seeded on substrates (glass or polystyrene) with a uniform coating of collagen. In some cases, hepatocytes were fluorescently labeled via incubation (1 hour at 37° C.) with Calcein-AM (Invitrogen) dissolved in culture medium at 5 μg/mL. Fibroblasts were fluorescently labeled with Cell-Tracker (Orange CMTMR, Invitrogen) as per manufacturer's instructions.

Biochemical Assays

Spent medium was stored at −20° C. Urea concentration was assayed using a calorimetric endpoint assay utilizing diacetylmonoxime with acid and heat (Stanbio Labs, Boeme, Tex.). Albumin content was measured using enzyme linked immunosorbent assays (MP Biomedicals, Irvine, Calif.) with horseradish peroxidase detection and 3,3',5,5"-tetramethylbenzidine (TMB, Fitzgerald Industries, Concord, Mass.) as a substrate.

Cytochrome-P450 Induction

Stock solutions of prototypic CYP450 inducers (Sigma) were made in Dimethylsulfoxide (DMSO), except for Phenobarbital, which was dissolved in water. Cultures were treated with inducers (Rifampin, β-Naphthoflavone, Dexamethasone and Omeprazole at 50 μM each, and Phenobarbital at 1 mM) dissolved in hepatocyte culture medium for 3-4 days. Control cultures were treated with vehicle (DMSO) alone for calculations of fold induction. To enable comparisons across inducers, DMSO levels were kept constant at 0.1% (v/v) for all conditions.

Toxicity Assays

Cultures were incubated with various concentrations of compounds dissolved in culture medium for 24 hours (acute toxicity) or extended time periods (chronic toxicity, 1-9 days). Cell viability was subsequently measured via the MTT (3-(4,5-dimethylthiazol-2-yl)-2,5-diphenyl tetrazolium bromide; Sigma) assay, which involves cleavage of the tetrazolium ring by mitochondrial dehydrogenase enzymes to form a purple precipitate. MTT was added to cells in DMEM without phenol red at a concentration of 0.5 mg/mL. After an incubation time of 1 hour, the purple precipitate was dissolved in a 1:1 solution of DMSO and Isopropanol. The absorbance of the solution was measured at 570 nm (SpectraMax spectrophotometer, Molecular Devices, Sunnyvale, Calif.).

Statistical Analysis

Experiments were repeated at least 2-3 times with duplicate or triplicate samples for each condition. Data from representative experiments is presented, whereas similar trends were seen in multiple trials. All error bars represent standard error of the mean.

Example 7—A Long-Term Model of the Rat Liver for Evaluating Drug Disposition

Long-Term Morphological and Functional Stability of Co-Cultures

Previously, rat hepatocytes were arranged in collagen-coated circular islands of prescribed dimensions and surrounded by 3T3-J2 fibroblasts to create micropatterned co-cultures. We found that co-cultures with a larger initial heterotypic interface (i.e. single hepatocyte islands surrounded by fibroblasts) had highest levels of liver-specific functions as compared to other configurations. Furthermore, hepatocytes in smaller patterns (<250 μm) intermingled significantly to dissipate the pattern, whereas larger islands (>450 μm) assumed a relatively stable conformation for several weeks. In this study, liver-specific functions in micropatterned and rat co-cultures were characterized over a period of several weeks. The pattern geometry with ~500 μm hepatocyte islands (~1200 μm center-to-center spacing) was selected since it provided high functional capacity along with retention of pattern fidelity for the duration of the co-cultures. The stability of the miniaturized rat liver tissues was assessed using both qualitative and quantitative criteria. Hepatocyte morphology in icropatterned co-cultures was found to be stable for over 2 months (FIG. 19A). That is, epatocytes displayed a polygonal shape with distinct nuclei and nucleoli, and visible bile canaliculi as typically seen in freshly isolated cells and in vivo. On the other hand, hepatocytes in pure monolayers spread out to adopt a 'fibroblastic' appearance (FIG. 19B). Furthermore, pattern fidelity was retained for the duration of the micropatterned co-cultures as assessed by phase contrast microscopy (FIG. 19C).

Figure 20A:
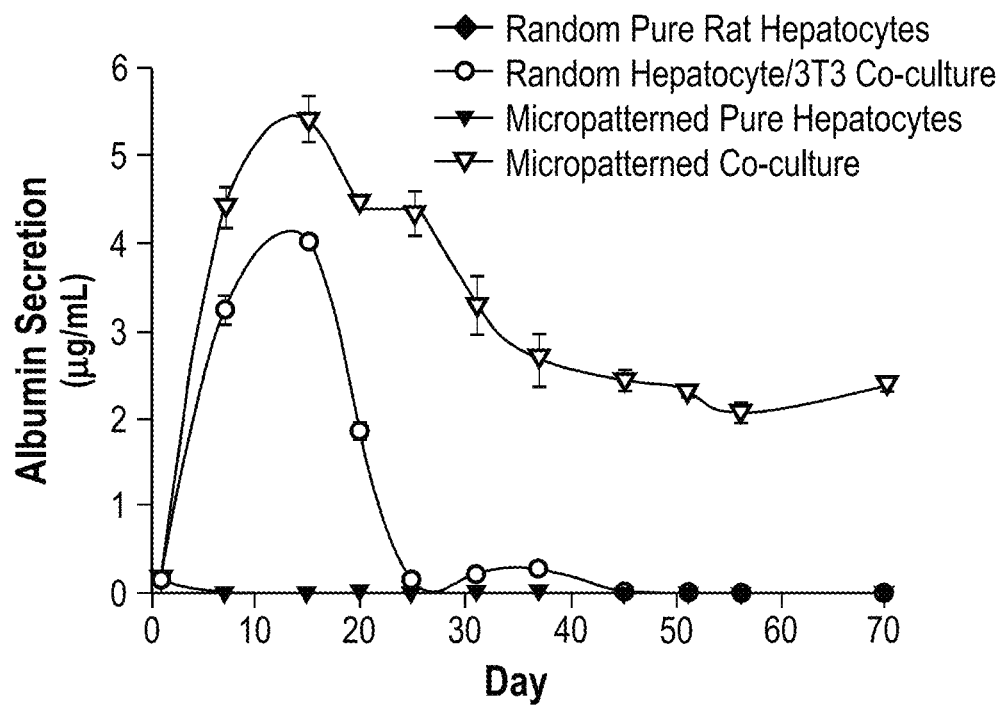
FIGS. 20A-20B demonstrate the long-term induction of hepatocellular functions in micropatterned cocultures. Elastomeric stencils were used to generate micropatterned co-cultures of primary rat hepatocytes and 3T3-J2 murine embryonic fibroblasts (500 μm islands, 1200 μm center-to-center spacing) in a multi-well format. Cultures were created in wells with a uniform coating of type-I collagen.
Figure 20B:
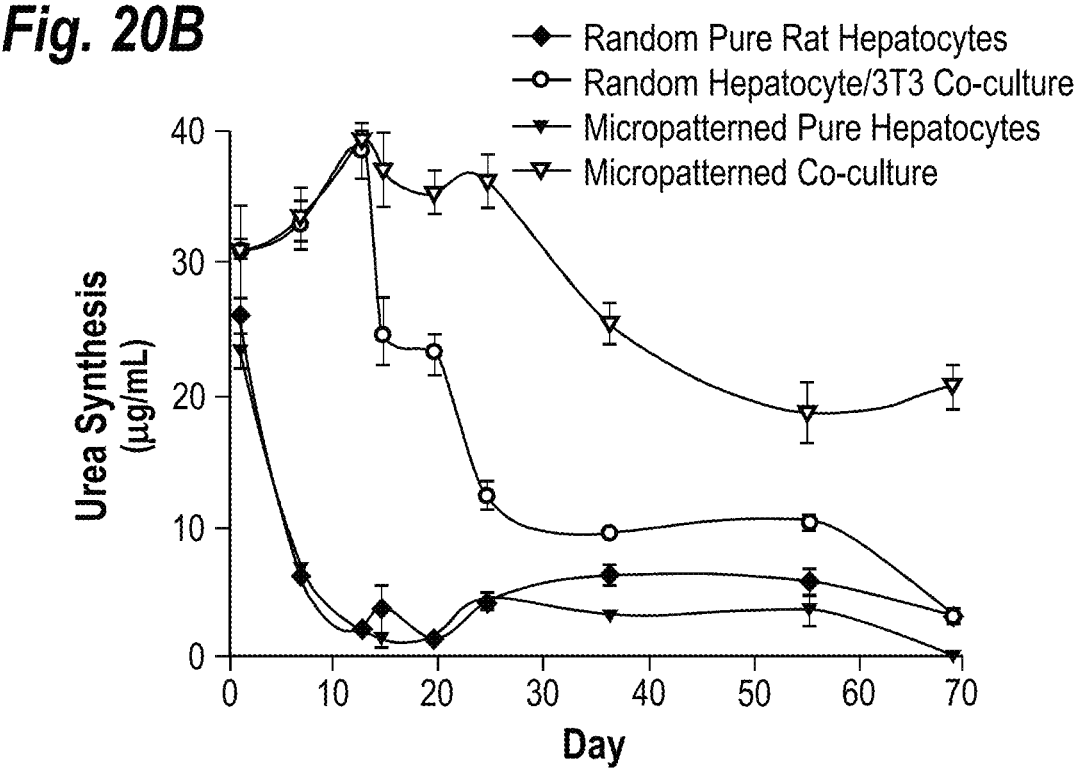

Next, liver-specific functions were characterized in micropatterned pure hepatocyte cultures and co-cultures and compared them to their randomly distributed counterparts (random cultures and co-cultures). Consistent with our previous studies, we found that both albumin secretion (FIG. 20A) and urea synthesis (FIG. 20B) were upregulated in all co-cultures as compared to pure hepatocyte monolayers, which displayed a rapid decline in such functions. After ~2 weeks, albumin secretion in co-cultures showed a sharp decline to near undetectable levels, while urea synthesis remained at a low baseline. Micropatterned co-cultures, on the other hand, displayed relatively high levels of liver-specific functions for over 2 months. Albumin secretion in micropatterned co-cultures was induced by ~20 fold on average (relative to day 1 pure hepatocyte function) for the first 4 weeks of culture and then stabilized down to ~10 fold for the next 6 weeks. Urea synthesis, however, was slightly upregulated to ~1.2 fold for the first 4 weeks in micropatterned co-cultures and then down-regulated slightly to ~0.7 fold for the next 6 weeks.

Activity of Phase I and Phase II Enzymes

Figure 21A:
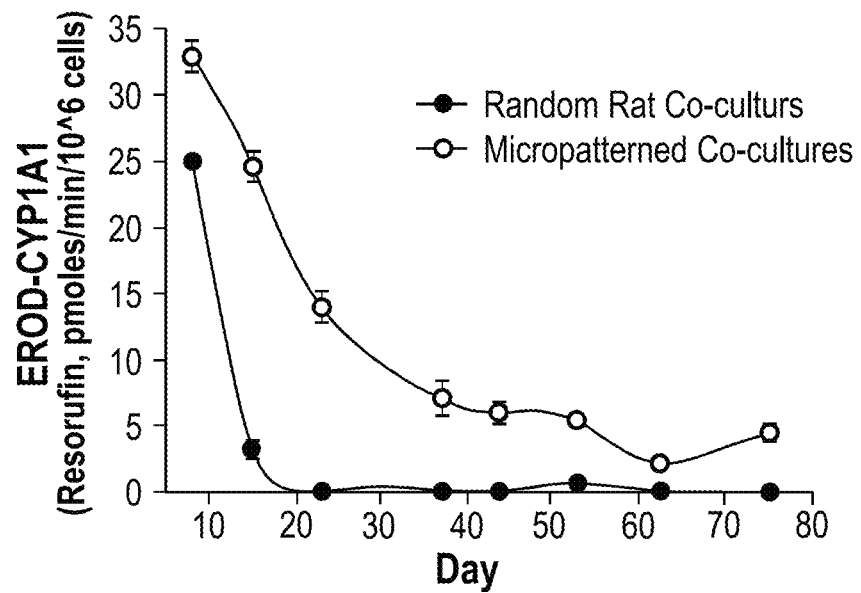
FIGS. 21A-21B demonstrate the long-term activity of CYP450 enzymes in micropatterned co-cultures.
Figure 21B:
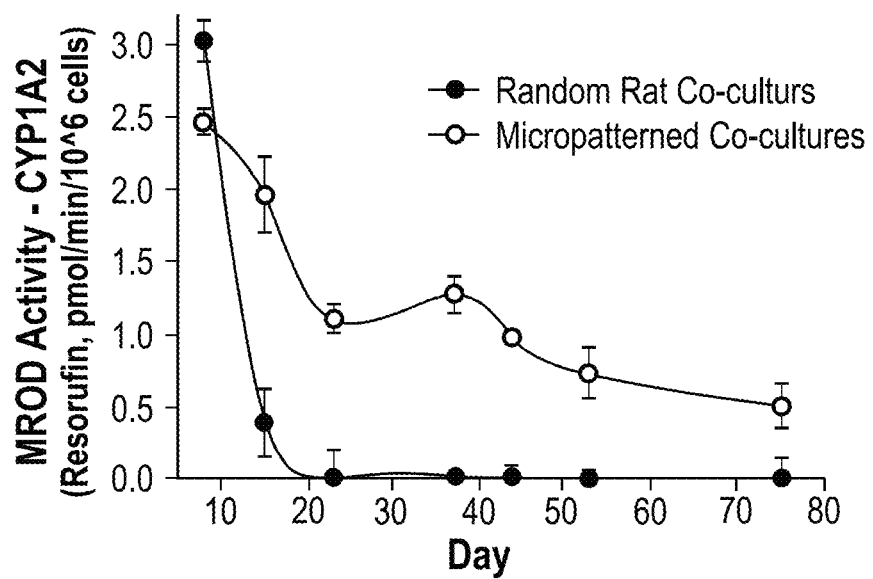
Figure 22A:
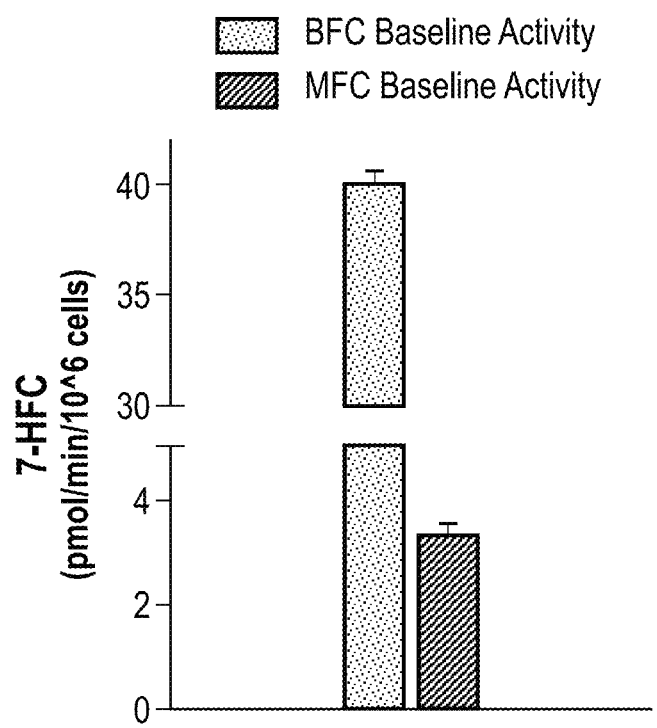
FIGS. 22A-22B depict the metabolism of prototypic substrates via Phase I and Phase II pathways.
Figure 22B:
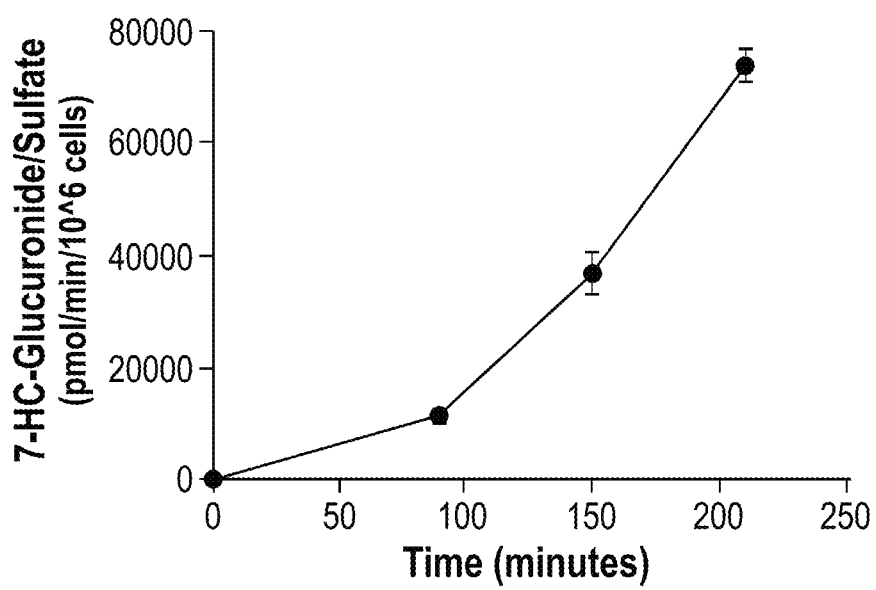

Resorufin-derivatives, ethoxy-resorufin (ER) and methoxy-resorufin (MR) was utilized in order to demonstrate activity of cytochrome-P450 (CYP450) phase-I enzymes in co-cultures of primary rat hepatocytes and 3T3-J2 murine embryonic fibroblasts. ER and MR dealkylation into fluorescent resorufin is mediated by CYP1A1 and CYP1A2 enzymes, respectively. Low levels of baseline (untreated) ER and MR were observed in metabolism in co-cultures. Therefore, in order to improve the signal-to-noise ratio, levels of CYP1A was 'induced' by pre-incubating co-cultures with 3 μM 3-Methylcholanthrene (3-MC) for 3 days prior to assessment of substrate metabolism. 3-MC is a known inducer of CYP1A1 and CYP1A2 expression in hepatocytes via the ligand-activated nuclear receptor AHR (aryl hydrocarbon receptor) [303]. In FIG. 21A, we show ER-dealkylation (post 3-MC induction for each data point) in co-cultures over a period of 10 weeks, while FIG. 21B shows MR-dealkylation. As with albumin secretion and urea synthesis, randomly distributed co-cultures displayed a dramatic decline in CYP1A1 and CYP1A2 enzyme activities to undetectable levels after ~2 weeks in culture. On the other hand, micropatterned co-cultures displayed CYP1A1 and CYP1A2 activities for 75 days. However, both CYP1A1 and CYP1A2 activities in micropatterned co-cultures declined over time, reaching to ~13% and ~20% on day 75 (relative to day 8 values), respectively. ER and MR are fluorimetric substrates specific for CYP1A enzymes. 7-methoxy-4-trifluoromethylcoumarin (MFC) and 7-benzyloxy-4-trifluoromethylcoumarin (BFC), on the other hand, are dealkylated by a variety of different CYP450s (i.e. non-specific substrates) into the fluorescent product, 7-hydroxy-4-trifluoromethylcoumarin (7-HFC). Use of non-specific substrates provides for an 'average' value of CYP450 activity, and is useful to determine whether CYP450 enzymes are functional in a particular system. In FIG. 22A, co-cultures were able to successfully dealkylate BFC and MFC into 7-HFC. The rate of BFC metabolism (picomoles per minute per $10^{\wedge}6$ cells) was observed to be ~12 fold higher than the rate of MFC metabolism. CYP450 enzymes are oxido-reductases that are part of the Phase I metabolic pathway in hepatocytes. The phase II family of enzymes, on the other hand, is typically involved in the conjugation of highly polar moieties (i.e. sulfate group, glucuronic acid) to xenobiotics to make them water-soluble for excretion out of the body via bile or through the kidneys. A useful substrate for evaluating conjugation reactions is the fluorescent substrate, 7-Hydroxycoumarin (7-HC), which gets modified to non-fluorescent compounds, 7-HC-Glucuronide and 7-HC-Sulfate. The level of conjugation can then be quantified by using bacterial-derived β-glucuronidase and aryl-sulfatase enzymes to 'deconjugate' the Phase II products and recover 7-HC fluorescence. In our micropatterned rat co-cultures, we observed time-dependent conjugation of 7-HC by Phase-II enzymes (FIG. 22B).

Functional Bile Canaliculi

Figure 23:
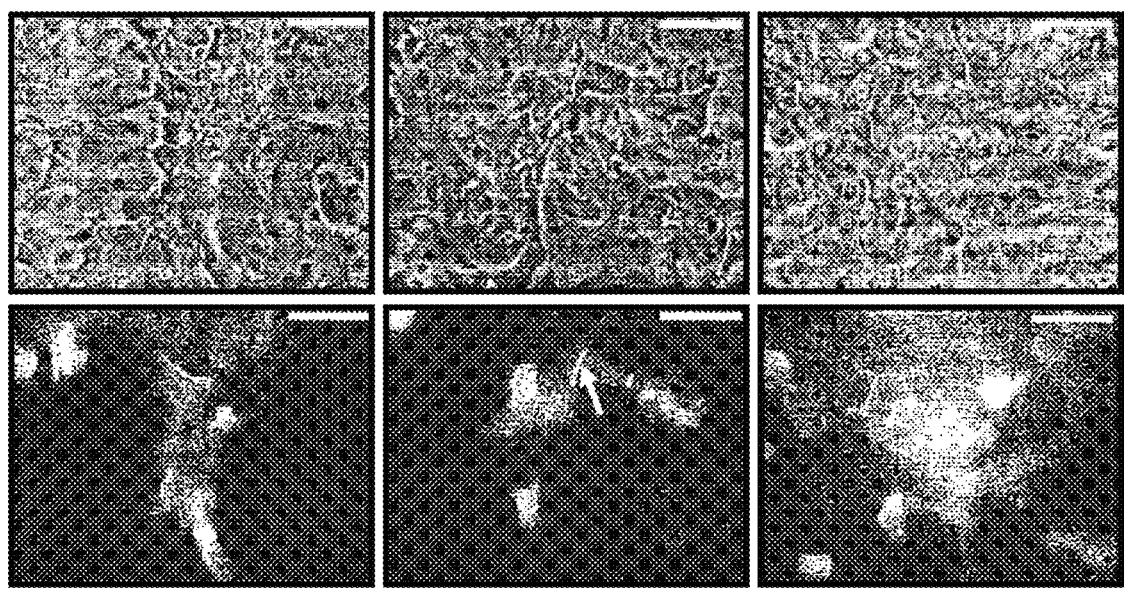
FIG. 23 depicts the staining of functional bile canaliculi in co-cultures. Co-cultures were incubated with carboxyfluorescein diacetate (CFDA), which gets internalized by hepatocytes, cleaved by esterases into a fluorescent dye and excreted into the bile canaliculi (see arrow in middle panel). Phase contrast micrographs of cocultures are shown on the top while the corresponding fluorescent pictures are shown on the bottom.

Besides albumin secretion, urea synthesis and Phase I and II activities, another marker of liver-specific function is the formation of functional bile canaliculi between hepatocytes. In FIG. 19, bile canaliculi are visible as distinct bright boundaries between hepatocytes. In order to demonstrate that these bile canaliculi are indeed functional, carboxyfluorescein diacetate (CFDA) was utilized, which is known to be taken up by hepatocytes, cleaved by intracellular esterases into a fluorescent dye (fluorescein), and subsequently excreted across the apical membrane of the hepatocyte into bile canaliculi. Hepatocytes were found to develop functional bile canaliculi (FIG. 23) upon cocultivation with 3T3-J2 fibroblasts, which did not take up CFDA to any considerable degree.

Drug-Drug Interactions

Figure 24A:
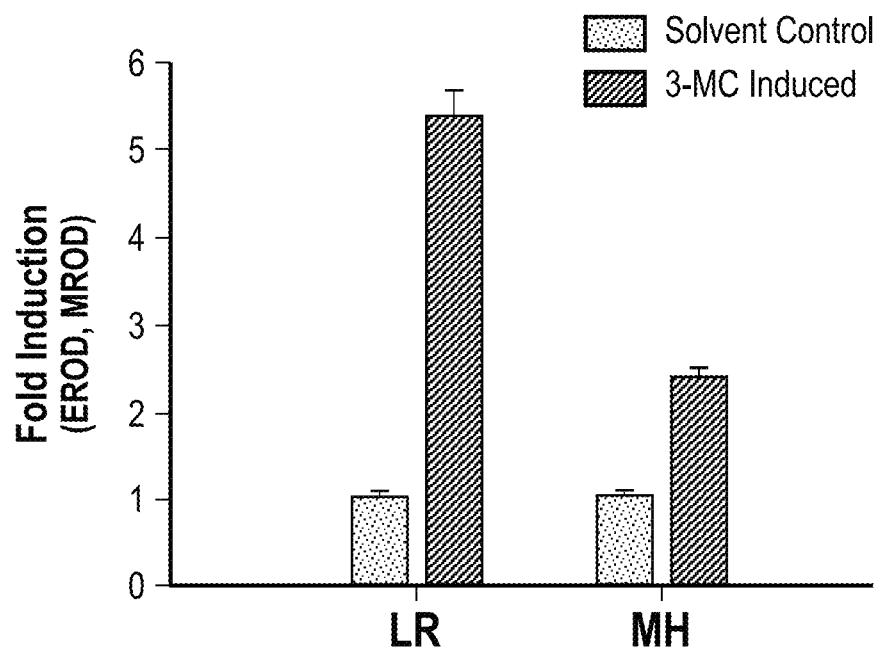
FIGS. 24A-24B depict the modulation of CYP450 activity.
Figure 24B:
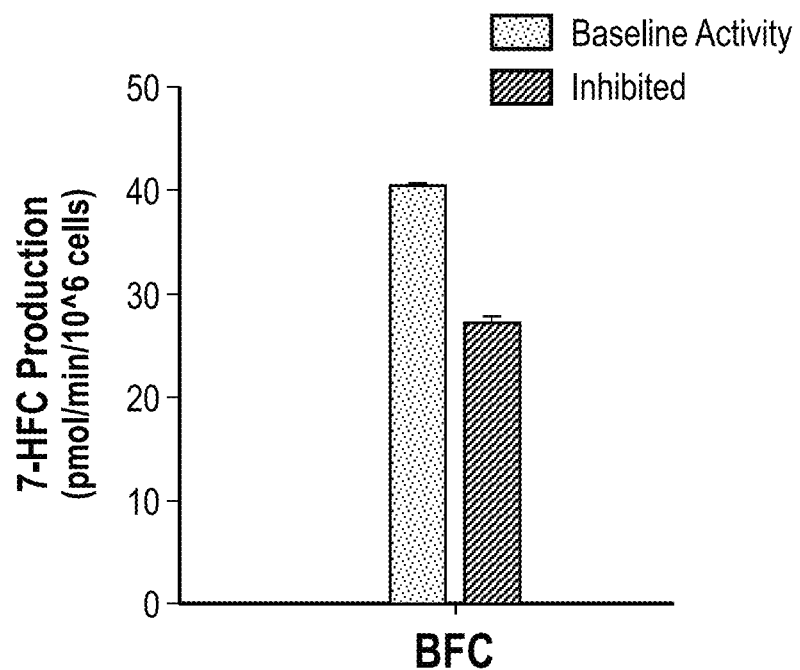

Modulation of CYP450 enzyme levels by pharmaceutical compounds is an important parameter in the occurrence of clinical drug-drug interactions. Cultures of primary hepatocytes from different species (i.e. human, rodent) are widely utilized to evaluate CYP450 induction and inhibition by drugs. In order to demonstrate that CYP450 enzymes can be induced in co-cultures of rat hepatocytes and 3T3-J2 fibroblasts, the prototypic CYP1A inducer, 3-Methylcholanthrene (3-MC) was utilized. Co-cultures were incubated with 3-MC for 72 hours before assessment of CYP1A1 and CYP1A2 activities via dealkylation of ethoxy-resorufin and methoxy-resorufin, respectively (FIG. 24A). CYP1A1 was induced by 5 fold over solvent-only controls, while CYP1A2 was induced by ~2 fold. Next, to show competitive inhibition of CYP450 activity, we utilized BFC as the substrate and ketoconazole as the inhibitor of CYP3A. Robust inhibition of BFC (~33%) dealkylation was seen when co-cultures were incubated with BFC in the presence ketoconazole (FIG. 24B).

Figure 25A:
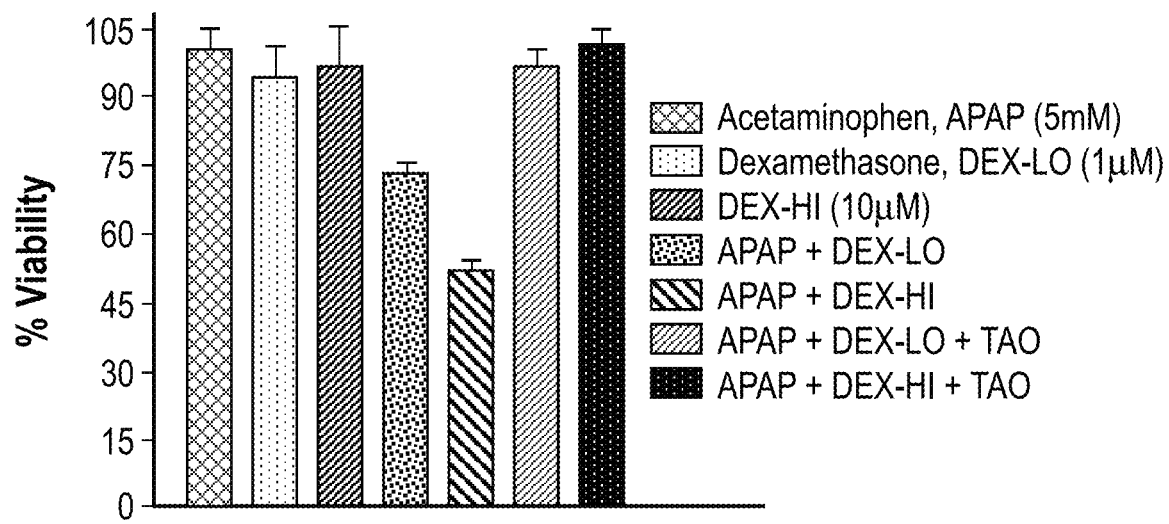
FIGS. 25A-25B demonstrate the dexamethasone-mediated enhancement of acetaminophen toxicity.
Figure 25B:
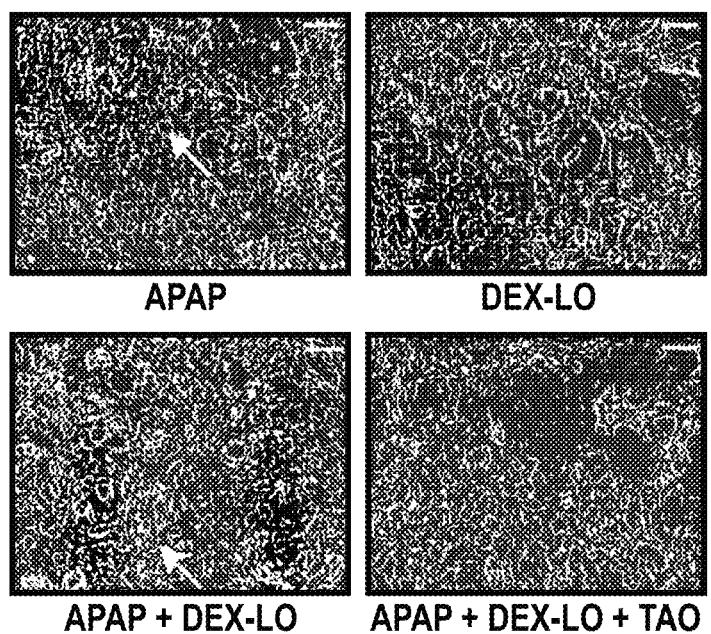
Figure 26A:
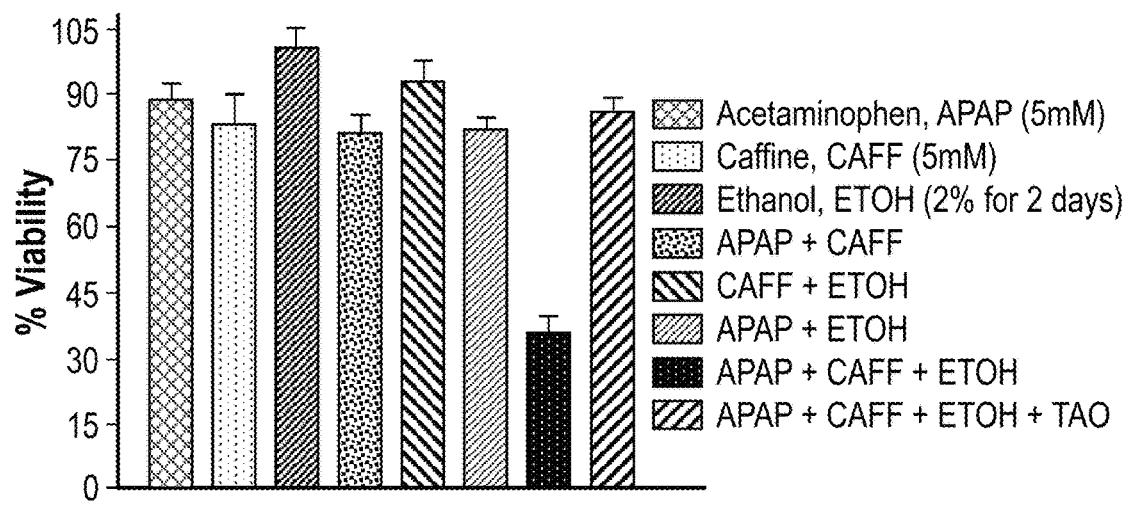
FIGS. 26A-26B demonstrate the caffeine-mediated enhancement of APAP toxicity in co-cultures treated with CYP3A inducers. Co-cultures were treated for 2 days with CYP3A inducers (EtOH, DEX) prior to administration of APAP. Following 24 hours of incubation with APAP, viability was assessed in co-cultures via the MTT assay (see Methods).
Figure 26B:
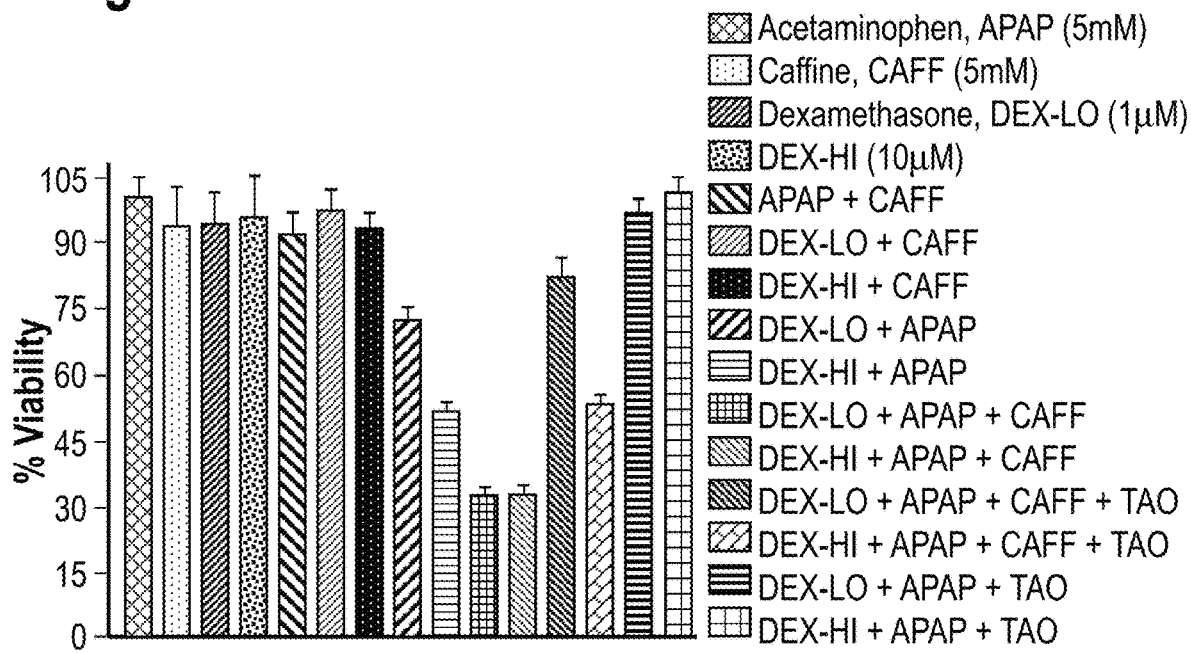

Drug-drug interactions due to the induction or inhibition of CYP450 enzymes can lead to serious toxicological consequences. In order to demonstrate such effects, a well-established in vivo model was utilized in which the toxicity of Acetaminophen (APAP, analgesic found in many over-the-counter medications including Tylenol) is enhanced upon induction of CYP3A. We first pre-treated co-cultures with increasing doses of dexamethasone (DEX) for 2 days to induce CYP3A levels. Then, co-cultures were incubated with a 5 mM dose of APAP for 24 hours, followed by assessment of viability via the MTT assay (see Methods). Data showed a substantial increase in APAPmediated toxicity in DEX-treated co-cultures over untreated controls (FIG. 25A). Specifically, inducing CYP3A levels with 1 µM DEX caused ~25% decrease in viability, while 10 µM DEX caused ~50%. To confirm that APAP-mediated cell death in DEX195 treated co-cultures was due to induced levels of CYP3A, we incubated DEX-treated cocultures with APAP in the presence of a competitive CYP3A inhibitor, Troleandomycin (TAO). Co-cultures in which CYP3A was 'blocked' via TAO showed minimal toxicity as compared to controls. One of the advantages of a 2-dimensional monolayer co-culture system over 3-D spheroids is improved in situ observation of cell behavior via conventional microscopy techniques. In FIG. 25B we show the interaction between APAP and DEX using morphological analysis. Severe changes in hepatocyte morphology were observed only in co-cultures that were treated with DEX prior to administration of APAP. Ethanol (EtOH) has also been shown to induce CYP3A levels in rodents and humans. Furthermore, caffeine has previously been shown to activate CYP3A activity in vitro and to increase APAP hepatotoxicity in rodents pretreated with prototypic inducers of CYP3A (i.e. DEX and EtOH). In our rat model, we observed that pre-treating co-cultures with 2% EtOH for 2 days did not make them more susceptible to the toxic effects of APAP (FIG. 26A). Furthermore, caffeine enhanced APAPmediated hepato-toxicity in co-cultures only when CYP3A levels were pre-induced using EtOH or DEX (FIG. 26 A, B). Incubating ethanol-treated co-cultures with TAO protected them from caffeine-mediated enhancement of APAP toxicity; however, TAO protected DEX-treated co-cultures from such enhancement only to a limited degree (i.e. toxicity was still seen in co-cultures).

Chronic Toxicity of Model Hepatotoxins

Figure 27A:
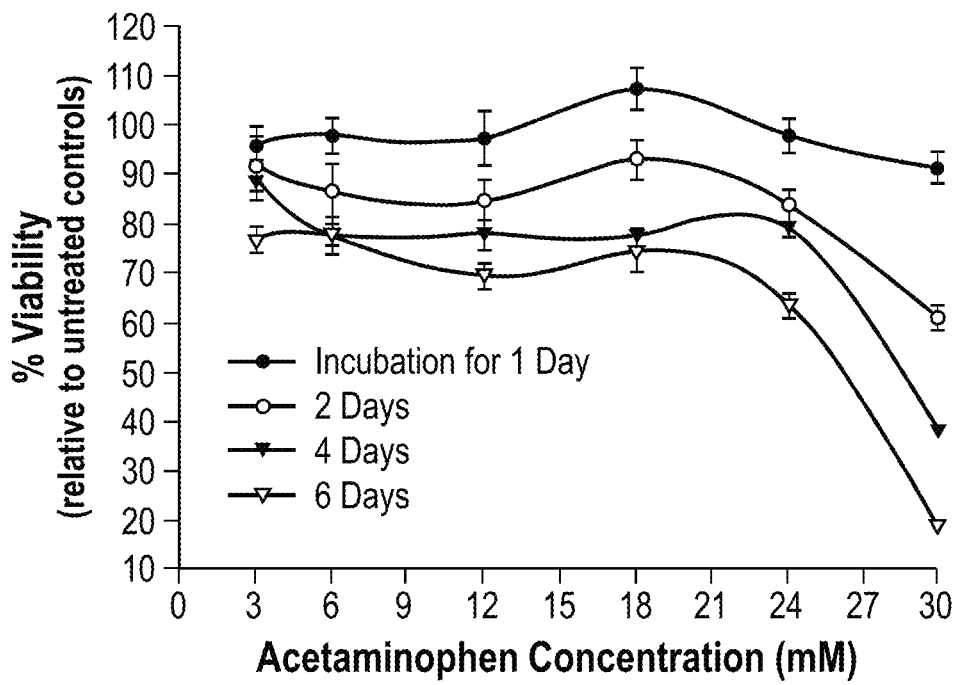
FIGS. 27A-27B depict the dose- and time-dependent toxicity of acetaminophen.
Figure 27B:
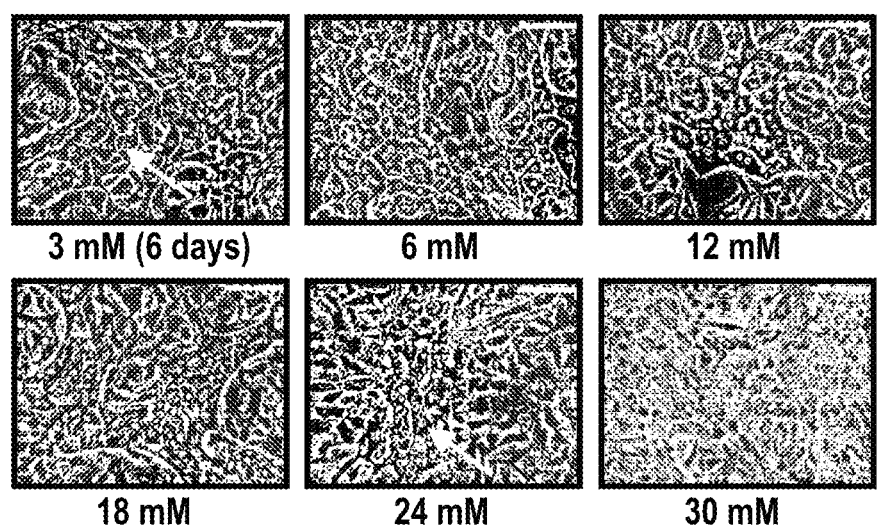
Figure 28A:
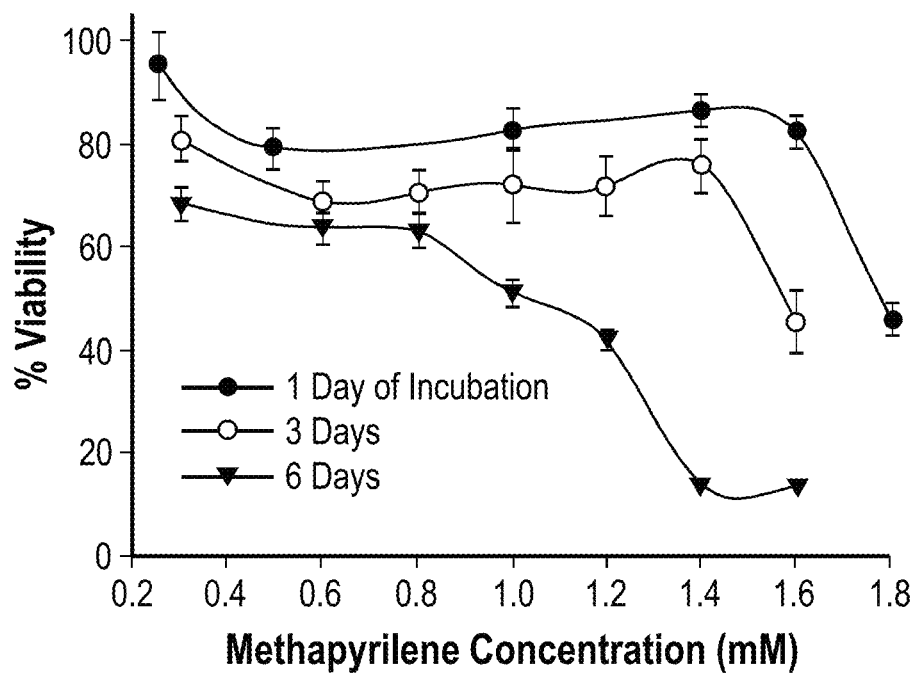
FIGS. 28A-28B depict the dose- and time-dependent toxicity of methapyrilene.
Figure 28B:
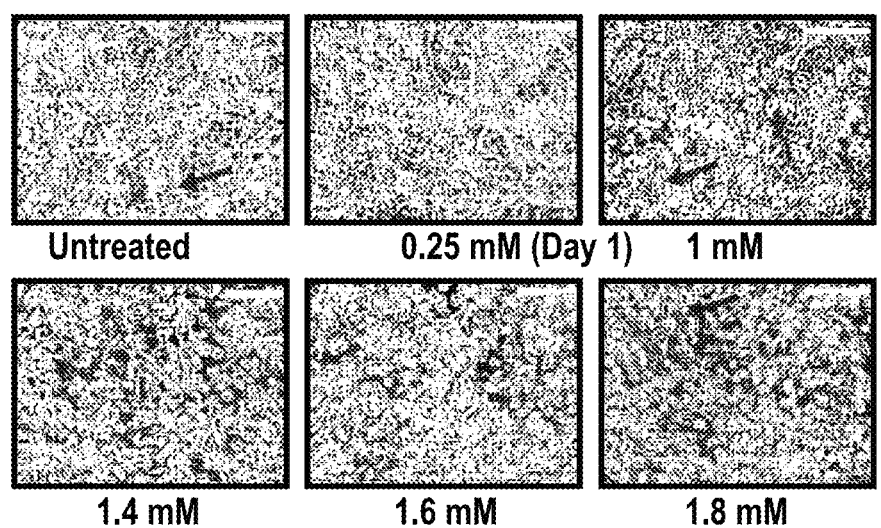

Toxicity of pharmaceuticals due to chronic exposure is clinically relevant. Since hepatocyte culture models utilized in the pharmaceutical industry lose viability and phenotypic functions within a few days, toxicity due to repeated drug exposures over days or weeks cannot be evaluated. Since co-cultures remain functional for several weeks, dose- and time-dependent toxicity of four known Hepatotoxins was investigated, including: Acetaminophen, ethapyrilene, Pyrilamine and Troglitazone. Co-cultures were incubated with varying doses of toxins dissolved in culture medium over several days. Mitochondrial activity (MTT assay, see methods) was evaluated at different time points to assess viability in co-cultures. Minimal toxicity (i.e. 90-100% viability relative to untreated controls) was seen in co-cultures that had been treated for 24 hours with Acetaminophen (APAP) doses ranging between 3 and 30 mM. However, following 6 days of repeated exposure, the viability in co-cultures ranged from 77% for 3 mM APAP to 19% for 30 mM (FIG. 27A). The dose-dependent toxicity profile of APAP exhibited a 'shoulder', whereby significant loss of viability was seen once a dose threshold was reached (30 mM). Furthermore, consistent with MTT data, hepatocyte morphology was severely affected in co-cultures that had been treated for 6 days with APAP doses ranging between 12 and 30 mM (FIG. 27B). However, no significant morphological changes were observed in co-cultures treated for 6 days with 3 or 6 mM APAP, even though mitochondrial activity was affected by ~20% as seen in FIG. 23A. In the case of Methapyrilene, the shifting of TC50 values (dose of drug causing 50% loss in viability) was observed to lower doses upon repeated exposures over 6 days (FIG. 28A). Specifically, the TC50 value dropped from ~1.8 mM after 1 day of incubation with methapyrilene to ~1 mM after 6 days. As with APAP, a 200 toxicity shoulder' was observed when co-cultures were incubated with methapyrilene. However, methapyrilene was toxic to hepatocytes at doses that were an order-of-magnitude lower than APAP (i.e. 1.8 versus 30 mM). Lastly, morphological analysis of Methapyrilenetreated co-cultures correlated well with the MTT data (FIG. 28B).

Figure 29A:
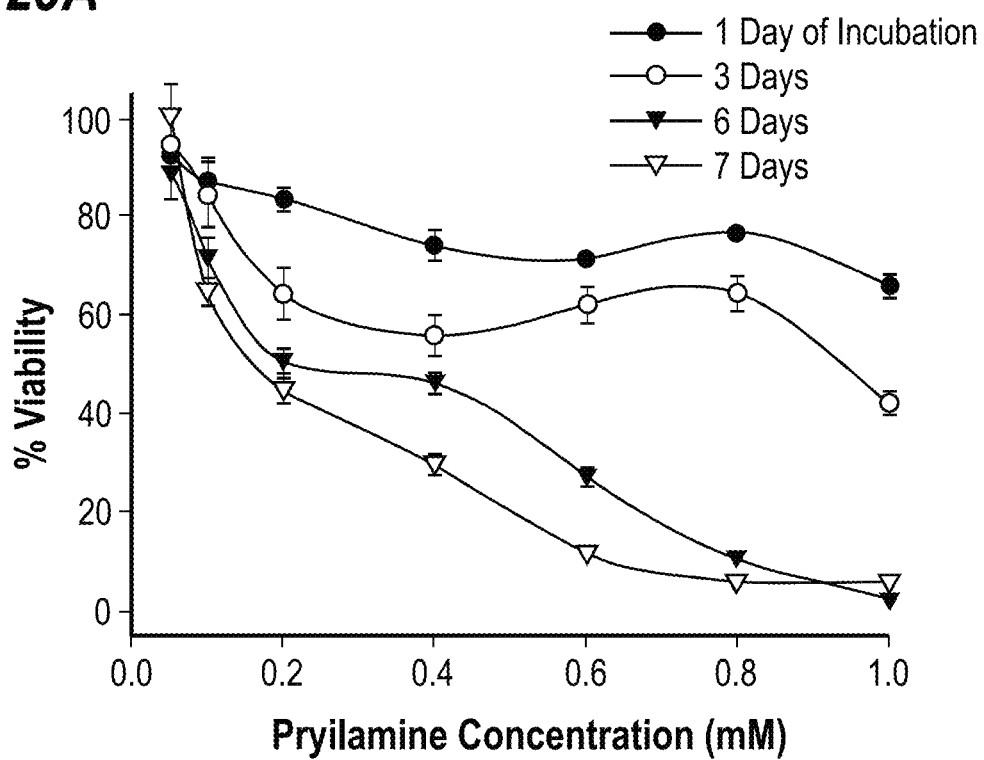
FIGS. 29A-29B depict the dose- and time-dependent toxicity of pyrilamine.
Figure 29B:
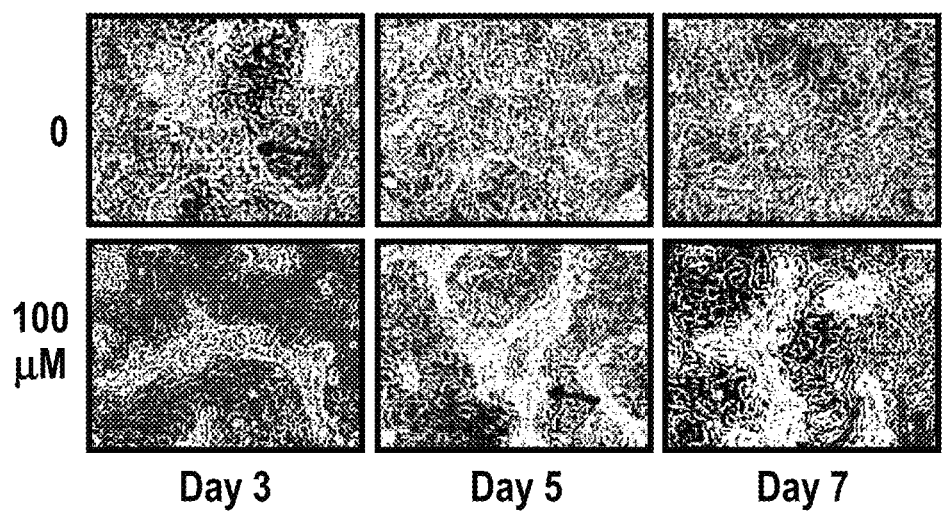
Figure 30A:
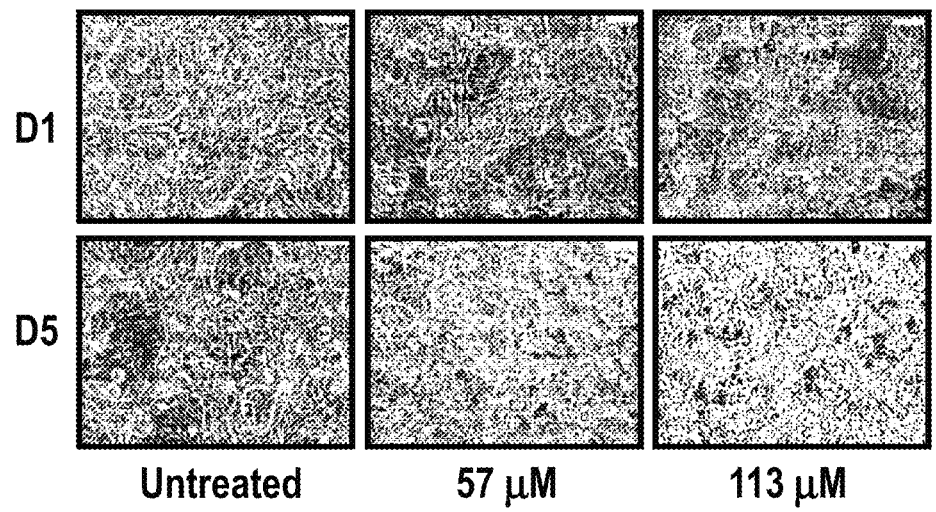
FIGS. 30A-30B depict the changes in cellular morphology in co-cultures following repeated exposures with troglitazone.
Figure 30B:
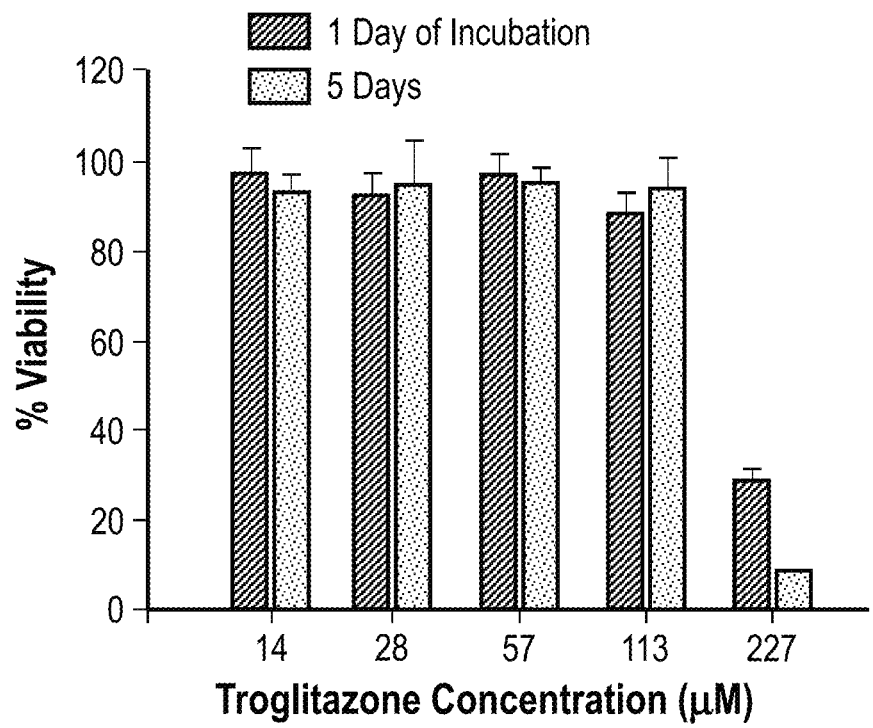

Next, the chronic toxicity of pyrilamine was evaluated in rat co-cultures. As with APAP and methapyrilene, we observed dose- and time-dependent toxicity in pyrilaminetreated co-cultures. Specifically, the TC50 value dropped from greater than 1 mM after 1 day of treatment to ~0.2 mM following 7 days of exposure (FIG. 29A). Furthermore, observation of co-cultures over several days revealed minimal changes in fibroblast morphology at a 100 μM dose of pyrilamine; however, hepatocyte morphology at that same dose was severely affected even after only 3 days of exposure (FIG. 29B). Lastly, the effect of troglitazone (oral hypoglycemic withdrawn from the market due to liver toxicity) was evaluated on co-cultures following repeated exposures. Drastic morphological changes was observed in co-cultures that had been treated for 5 days with troglitazone doses ranging between 57 and 113 μM (FIG. 30A). However, no concomitant decline in viability was detected for such co-cultures (FIG. 30B).

Figure 31:
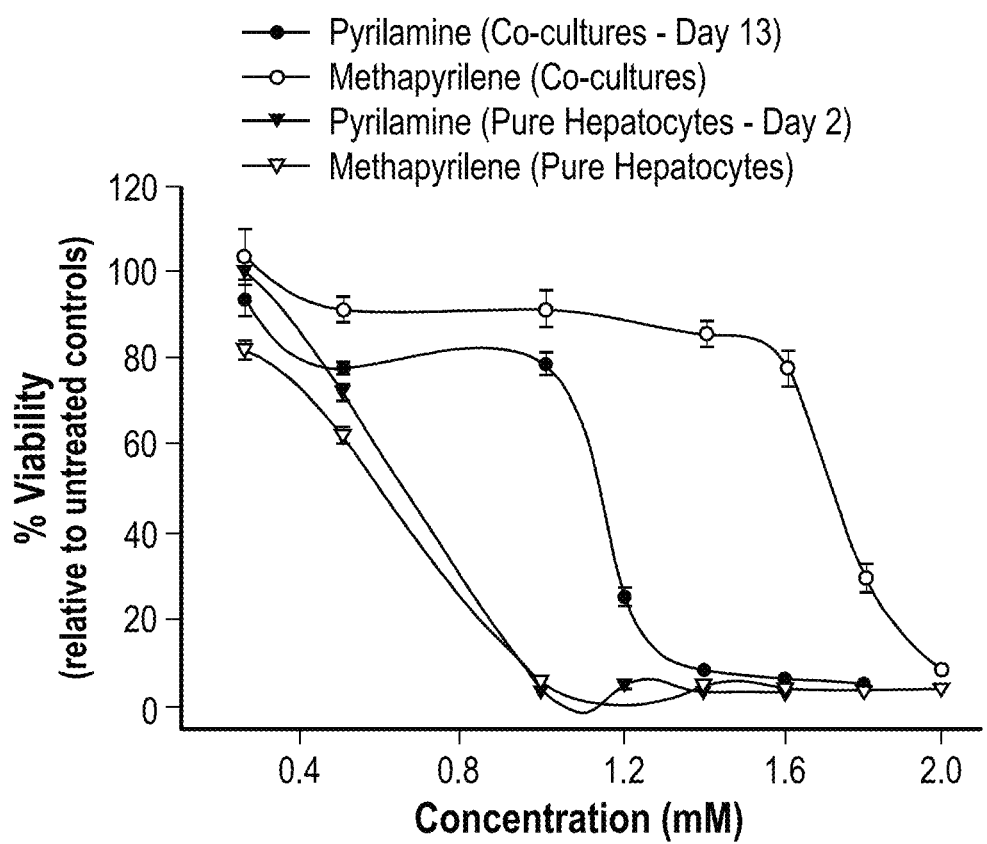
FIG. 31 depicts the methapyrilene and pyrilamine toxicity in pure hepatocyte monolayers and co-cultures. Pure hepatocyte monolayers (day 2 of culture) and hepatocytefibroblast co-cultures (day 13), prepared from the same rat liver, were incubated with varying doses of methapyrilene or pyrilamine dissolved in culture medium for 24 hours. Viability was subsequently assessed via the MTT assay (see Methods for details).
Figure 32A:
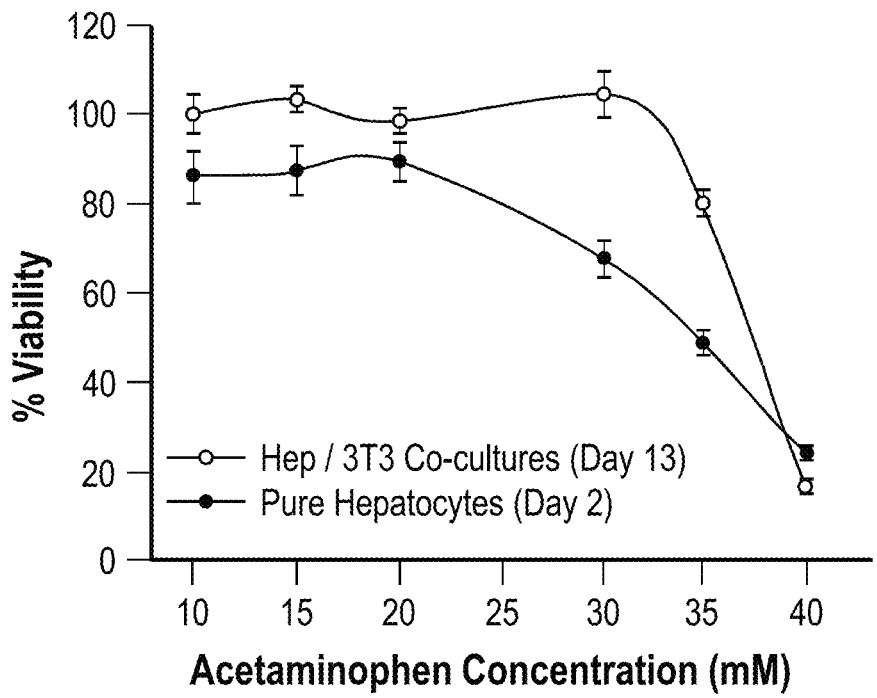
FIGS. 32A-32B depict acetaminophen and troglitazone toxicity in pure hepatocyte monolayers and co-cultures. Pure hepatocyte monolayers (day 2 of culture) and hepatocyte-fibroblast co-cultures (day 13), prepared from the same rat liver, were incubated with varying concentrations of acetaminophen or troglitazone dissolved in culture medium for 24 hours. Viability was subsequently assessed via the MTT.
Figure 32B:
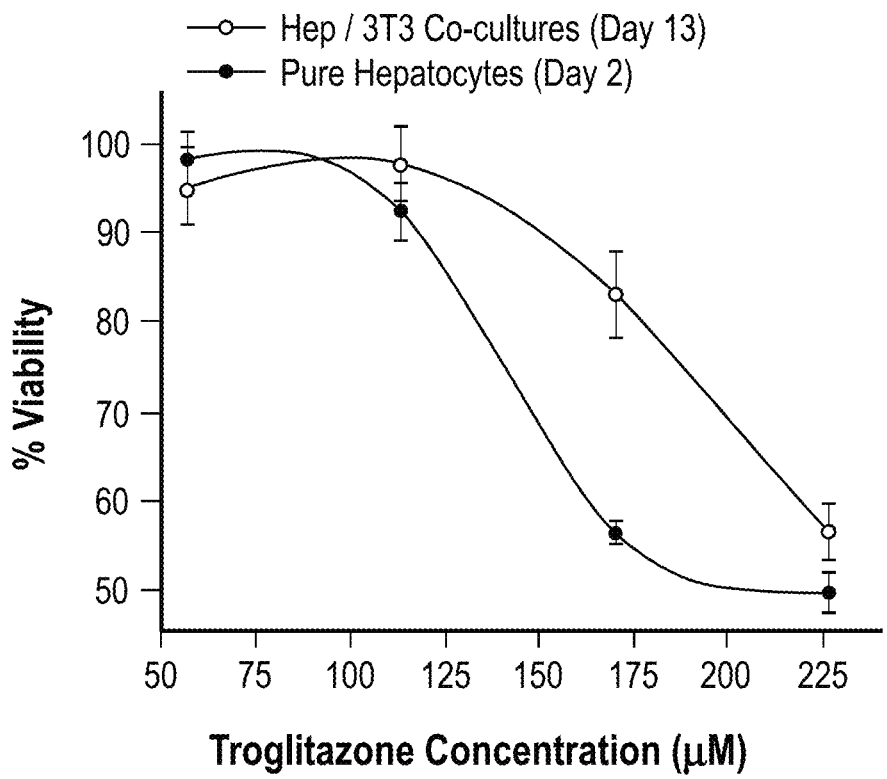

Comparison of Drug Toxicity in Pure Hepatocyte Monolayers and Hepatocyte-Fibroblast Co-Cultures Pure hepatocyte monolayers rapidly lose phenotypic functions and thus represent an 'unstable' model of the liver. On the other hand, FIGS. 19-23 show 3T3-J2 fibroblasts can stabilize hepatic functions (i.e. albumin secretion, urea synthesis, Phase I and II enzyme activity) in co-culture for several weeks. The objective here was to compare toxicity of model Hepatotoxins in pure hepatocyte monolayers and co-cultures. Pure hepatocyte monolayers (Day 2 of culture) or hepatocyte-fibroblast co-cultures (Day 13) prepared from the same rat liver were treated with Hepatotoxins for 24 hours, after which viability was assessed via the MTT assay. In FIG. 31, significant differences in toxic profiles of methapyrilene and pyrilamine were shown across the two culture models. Specifically, we found that both compounds were more toxic to pure monolayers as compared to co-cultures. For instance, at a 1 mM compound dose, viability in pure monolayers had dropped to less than 6% (relative to untreated controls), while co-cultures showed greater than 80% viability. Furthermore, we observed quantitative differences in the TC50 values of methapyrilene (between 1.4 and 1.6 mM) and pyrilamine (between 1 and 1.2 mM) only in the stable co-culture model of the rat liver. In contrast to methapyrilene and pyrilamine, acetaminophen (APAP) and troglitazone were found to be more toxic to co-cultures as compared to pure monolayers (FIG. 32). For example, incubating pure monolayers with a 30 mM dose of APAP for 24 hours had no effect on their viability; however, co-cultures displayed a ~33% loss. Similarly, exposing co-cultures to a 170 μM dose of troglitazone reduce their viability by ~44%; however, such a reduction was seen in pure monolayers only when the troglitazone concentration was raised to 227 μM.

Species-Specific Phase I and Phase II Substrate Metabolism

Figure 33A:
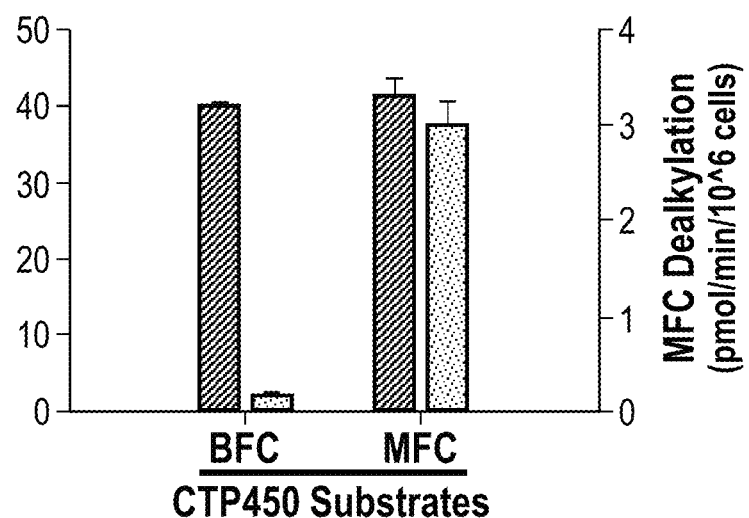
FIGS. 33A-33C depict a comparison of Phase I- and Phase II-mediated substrate metabolism in human and rat co-cultures. Micropatterned cultures with either primary human or primary rat hepatocytes were created using the stencil-based process. Subsequent addition of 3T3-J2 fibroblasts created co-cultures.
Figure 33B:
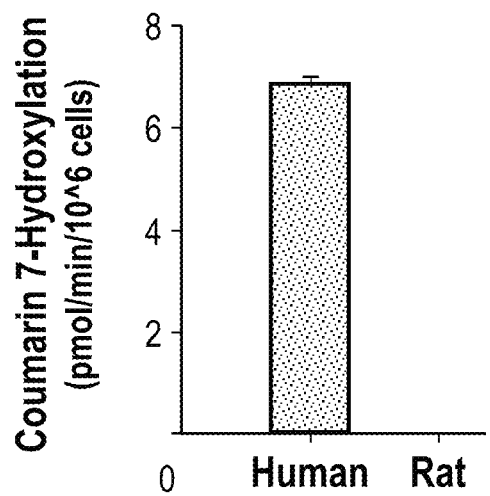
Figure 33C:
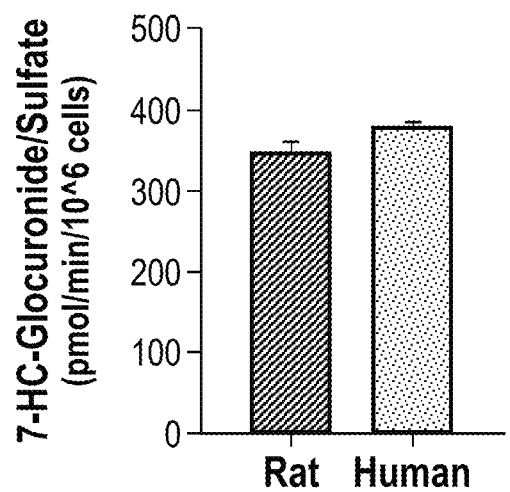

Significant variations in hepatocellular functions (i.e. CYP450 enzymes) across different species have been implicated in the inability of animal models to adequately predict adverse outcomes in clinical trials involving humans. Nonetheless, studies in live animals are required by the FDA since they provide valuable in vivo data in a preclinical setting. Therefore, the selection of an animal species (i.e. rat, mouse, monkey, guinea pig) in which the liver-specific metabolism and toxicity of a particular candidate drug are similar to that seen in humans is crucial for clinical success. In vitro human and animal models that closely resemble in-vivo functionality may find use in such a selection process. Here, to demonstrate utility in drug development, the metabolism of specific Phase I and II enzyme substrates were compared in micropatterned co-cultures utilizing either primary human or rat hepatocytes (FIG. 33). For instance, BFC was dealkylated in rat co-cultures at a rate (pmoles/min/10^6 cells) that was ~18 fold greater than the rate seen in human co-cultures. On the other hand, rat co-cultures were unable to hydroxylate coumarin, while human co-cultures did so at a rate greater than 6 pmol/min/10^ 6 cells. Lastly, we observed that both human and rat co-cultures displayed similar rates for a) CYP450-mediated dealkylation of MFC, and b) Phase II-mediated conjugation of 7-HC. Furthermore, species specific differences were previously demonstrated in omeprazole-mediated CYP1A induction by comparing the responses of micropatterned human and rat co-cultures.

Co-Cultivation of Hepatocytes with Liver-derived Non-parenchymal Cells

Figure 34A:
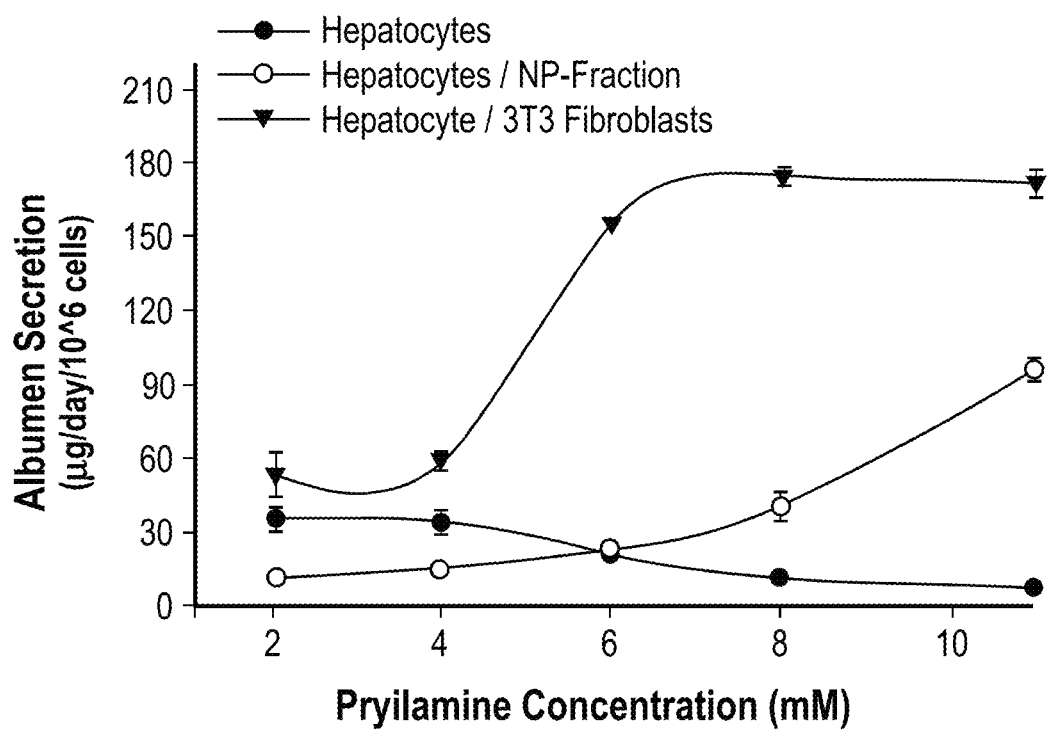
FIGS. 34A-34B depict a co-cultivation of rat hepatocytes with nonparenchymal fraction of the liver. Micropatterned co-cultures with either 3T3 fibroblasts or the whole nonparenchymal fraction of the liver (NP-fraction) were created using the stencil-based process.
Figure 34B:
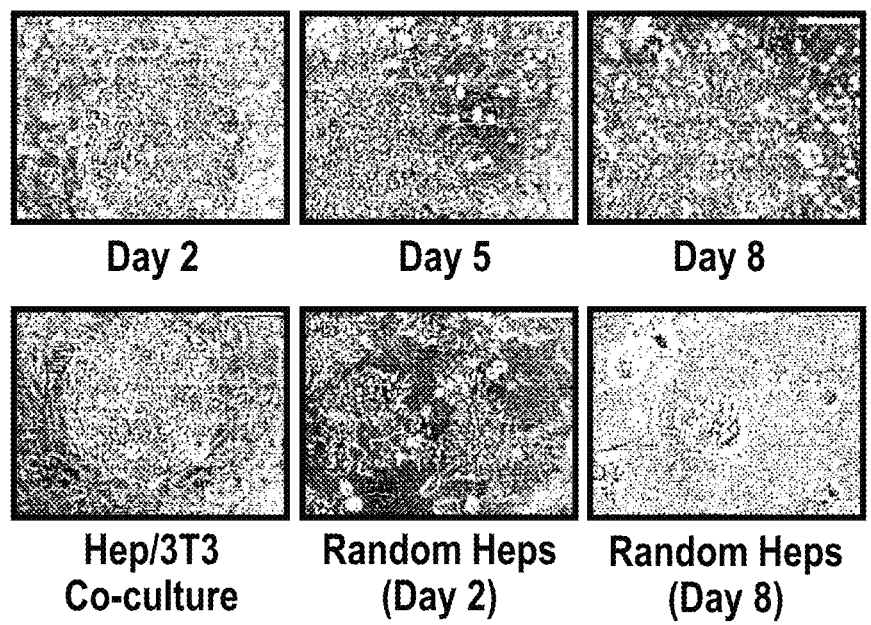

In this study, non-liver-derived 3T3 murine embryonic fibroblasts were utilized to stabilize phenotypic functions of rat hepatocytes in vitro. The 'co-culture effect', however, has been reported for nonparenchymal cells from both within and outside the liver. In this study, the 3T3 model was functionally compared with co-cultures that contained liver-derived primary nonparenchymal cells. Therefore, primary rat hepatocytes were co-cultivated with the whole non-parenchymal fraction of the rat liver (NP-fraction). In FIG. 36, albumin secretion was shown in micropatterned co-cultures containing either the NP-fraction or 3T3 fibroblasts. Cumulative albumin secretion over a period of 11 days was ~1.7 fold higher in NP-fraction co-cultures and ~5.5 fold higher in 3T3 co-cultures as compared to unstable pure hepatocyte controls. Furthermore, liver-derived non-parenchymal cells proliferated over time in co-cultures, which induced changes in hepatocyte morphology (FIG. 34B). Hepatocyte morphology in 3T3 co-cultures remained relatively stable for the duration of the experiment. Pure hepatocyte monolayers, on the other hand, adopted a spread-out, 'fibroblastic' morphology. Thus, the rat liver model developed and characterized herein represent 24-well plates with each well containing ~12,000 hepatocytes organized in 37 colonies of 500 μm diameter, for a total of 888 repeating hepatic microstructures per plate. Micropatterned co-cultures were functionally compared with their randomly distributed counterparts seeded on substrates uniformly coated with collagen (i.e. random co-cultures). Our results indicated that for the first ~2 weeks of co-culture, a variety of liver-specific functions (albumin secretion, urea synthesis, and cytochrome-P450-1A activity) were similar in value in the two models (FIGS. 20 and 21). However, after that time period, functions in random co-cultures declined to near undetectable levels within a week, whereas micropatterned co-cultures remained functional for ~10 weeks. Morphological observation revealed that the functional decline in random co-cultures was accompanied by a loss of hepatocyte viability (data not shown). The timing of the functional decline in random co-cultures was not consistent between multiple repeat trials, as a range of 3-8 weeks was observed. Micropatterned co-cultures, on the other hand, reproducibly remained functional for up to 10 weeks.

Regardless of any functional improvements, micropatterned co-cultures offer several advantages over randomly distributed ones, which include: precise control over homotypic and heterotypic interactions towards consistent modulation of phenotypic functions; and, imaging and tracking of individual hepatocyte islands over time to monitor cellular responses to specific stimuli. It should be noted though that in this work, a few studies demonstrating utility of co-cultures in drug development were carried out with 1-2 week old randomly distributed co-cultures (high functioning) partly due to the ease with which such co-cultures can be created as compared to micropatterned ones.

Nonparenchymal Cell Culture

3T3-J2 murine embryonic fibroblasts were acquired and cultured as described in chapter 2 of this dissertation. In some cases, fibroblasts were growth-arrested by incubation with 10 µg/mL Mitomycin C (Sigma, St. Louis, Mo.) in culture media for 2 hours at 37° C. The nonparenchymal fraction of the rat liver was recovered via centrifugation following digestion of the liver with collagenase. Briefly, a suspension with different types of liver cells (i.e. hepatocytes, sinusoidal endothelial cells, and kupffer.

6Hepatocyte-Nonparenchymal Co-Cultures

Primary rat hepatocytes were isolated and purified. For studies comparing species-specific responses, primary human hepatocytes were purchased in suspension from commercial vendors and cultured. Co-cultured hepatocyte-fibroblast co-cultures were generated. Briefly, collagen-coated polystyrene plates (24-well format) were seeded with hepatocytes (100,000 cells per well) in hepatocyte culture medium (500 µL per well). For co-culture experiments, 3T3 fibroblasts (1:1 ratio with hepatocytes) were seeded in their respective medium 12-24 hours after initiation of adherent hepatocyte cultures. The culture medium was replaced to hepatocyte culture medium the day after fibroblast cell seeding and subsequently replaced daily. Briefly, elastomeric polydimethylsiloxane (PDMS) stencil devices, consisting of thin membranes (~300 µm) with through-holes (500 µm with 1200 µm center-to-center spacing) at the bottom of each well of a 24-well mold were used to create collagenous domains on tissue culture polystyrene. Hepatocytes were seeded in serum-free hepatocyte culture medium on collagen-patterned substrates, resulting in a hepatocyte micropattern due to selective cell adhesion. The cells were washed with media 2 hours later to remove unattached cells and incubated with serumsupplemented hepatocyte media overnight. Growth-arrested 3T3 fibroblasts were seeded onto hepatocytes to create co-cultures as described above; however, a 3:1 fibroblast to hepatocyte ratio was used due to lack of fibroblast proliferation. In some cases, liver derived nonparenchymal cells (10:1 nonparenchymal to hepatocyte ratio) were used instead of fibroblasts to create co-cultures.

Hepatocellular Function Assays

Spent media was stored at −20° C. Urea concentration was assayed using a colorimetric endpoint assay utilizing diacetylmonoxime with acid and heat (Stanbio Labs, Boerne, Tex.). Albumin content was measured using enzyme linked immunosorbent assays (MP Biomedicals, Irvine, Calif.) with horseradish peroxidase detection and 3,3',5,5"-tetramethylbenzidine (TMB, Fitzgerald Industries, Concord, Mass.) as substrate. For some experiments, cultures were treated with 3 µM 3-Methylcholanthrene (Sigma) dissolved in hepatocyte culture medium for 3 consecutive days to induce cytochrome-P450 1A (CYP1A) enzyme levels. Control cultures were treated with solvent alone (Dimethylsulfoxide, DMSO) to measure baseline enzyme activity. CYP1A1 activity was assessed via dealkylation of ethoxy-resorufin (ER, Sigma) into fluorescent resorufin, while methoxy-resorufin (MR, Sigma) was used as a substrate for CYP1A2. Briefly, cultures were incubated with 5 µM substrate dissolved in DMEM without phenol red for 30-60 min. Resorufin fluorescence (excitation/emission: 530/590 nm) in collected supernatants was quantified by means of a fluorescence micro-plate reader (Molecular Devices, Sunnyvale, Calif.). Protocols in chapter 5 were followed to evaluate the Phase I-mediated hydroxylation of coumarin, dealkylation of 7-methoxy-4-rifluoromethylcoumarin (MFC) and 7-benzyloxy-4-trifluoromethylcoumarin (BFC), and phase II-mediated conjugation of 7-Hydroxycoumarin (7-HC) in rat co-cultures.

Staining of Functional Bile Canaliculi

Co-cultures were washed three times with phenol-red free DMEM, incubated with 6 µg/mL CFDA (5-and-6-carboxyfluorescein diacetate, mixed isomers—purchased from Invitrogen, Carlsbad, Calif.) for 10 minutes, and washed three times again prior to examination with fluorescence microscopy (excitation/emission: 495/520 nm). Specimens were observed and recorded using a Nikon Diaphot microscope equipped with a SPOT digital camera (SPOT Diagnostic Equipment, Sterling Heights, Mich.), and MetaMorph Image Analysis System (Universal Imaging, Westchester, Pa.) for digital image acquisition.

Acute and Chronic Toxicity Studies

All chemicals were purchased from Sigma. In order to evaluate the acute toxicity of compounds, cultures were incubated with various concentrations of compounds dissolved in culture medium for 24 hours. For chronic studies, culture media with fresh Hepatotoxins was added every 2 days. Cell viability at different time points was subsequently measured via the MTT assay.

Drug-Drug Interaction Studies

All chemicals were purchased from Sigma. Co-cultures were first treated with dexamethasone (1-10 µM) or ethanol (2% vol/vol) dissolved in culture medium for 2 days to induce CYP3A levels. Next, co-cultures were incubated for 24 hours with either fresh media or fresh media supplemented with one or combinations of the following compounds: Acetaminophen (5 mM in culture medium), Caffeine (5 mM), and Troleandomycin (TAO, 100 µM). TAO was specifically used to inhibit CYP3A enzymes in co-cultures. Following the 24 hour incubation period, viability was assessed using the MTT assay.

INCORPORATION BY REFERENCE

All publications, U.S. patents and U.S. published patent applications cited in this specification are herein incorporated by reference as if each individual publication or patent or patent application were specifically and individually indicated to be incorporated by reference. The citation of any publication is for its disclosure prior to the filing date and should not be construed as an admission that the present invention is not entitled to antedate such publication by virtue of prior invention. U.S. patent application publication 2001/0023073 is expressly incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A monolithic multi-well cell plate comprising a plurality of wells, each well comprising a micropatterned substrate prepared by a process comprising the steps of:
    adsorbing biomolecules onto a surface of a substrate within each well of the multi-well plate, thereby forming a coated surface of the substrate;
    compressing a micropatterned etch mask onto the coated surface of the substrate, wherein said compression step seals the etch mask to the coated surface of the substrate such that the biomolecules are protected from ablation;
    exposing the compressed micropatterned etch mask and coated surface of the substrate to a gas plasma for a period of time sufficient to ablate the exposed surfaces of the substrate, thereby ablating the exposed surfaces of the substrate,
    removing the micropatterned etch mask, whereby the biomolecules remain adsorbed, such that the micropatterned substrate is formed,
    thereby providing a multi-well plate comprising a plurality of wells, each well comprising a micropatterned substrate.

2. The multi-well plate of claim 1, wherein said multi-well cell plate is a 24-well or a 96-well or a 384-well cell plate.

3. The multi-well plate of claim 1, wherein said biomolecule is selected from the group consisting of peptides, polypeptides, nucleic acids, nucleic acid binding partners, proteins, receptors, antibodies, enzymes, carbohydrates, oligosaccharides, polysaccharides, cells, cell aggregates, cell components, lipids, arrays of ligands, non-protein ligands, liposomes, and microorganisms.

4. The multi-well plate of claim 1, wherein the process further comprises rinsing and drying said coated surface after the adsorbing step.

5. The multi-well plate of claim 1, wherein said exposing step is carried out in a plasma asher.

6. The multi-well plate of claim 1, wherein the micropatterned etch mask is one solid elastomeric piece.

7. The multi-well plate of claim 1, wherein the micropatterned etch mask comprises a plurality of pillars.

8. The multi-well plate of claim 1, wherein the micropatterned etch mask comprises chrome or elastomeric poly(dimethylsiloxane) or rubber or plastic.

9. The multi-well plate of claim 1, wherein the adsorbed molecules are different.

10. The multi-well plate of claim 9, wherein the different molecules each have a different pattern.

11. The multi-well plate of claim 1, wherein the micropatterned etch mask comprises elastomeric poly(dimethylsiloxane).

12. The multi-well plate of claim 1, wherein the micropatterned etch mask comprises an about 50 μm to about 1 mm thick piece of elastomeric poly(dimethylsiloxane).

13. The multi-well plate of claim 1, wherein said substrate surface is ceramic, metal, glass, or plastic.

14. The multi-well plate of claim 1, wherein said substrate comprises fluoropolymers, fluorinatedethylene propylene, polyvinylidene, polydimethylsiloxane, polystyrene, polycarbonate, and polyvinyl chloride, fused silica, polysilicon, or single silicon crystals.

15. The multi-well plate of claim 1, wherein said biomolecules are hyaluronic acid, collagen, fibronectin, lamanin, or matrigel.

16. The multi-well plate of claim 1, wherein the process further comprises:
    contacting said micropatterned substrate with cells.

17. The multi-well plate of claim 16, wherein said cells are hepatocytes, endothelial cells, kidney, muscle, pancreas, epithelium cells, tissue/skin cells, intestinal cells or stem-cell derived cells.

18. The multi-well plate of claim 17, wherein said cells are rat cells, human cells, mouse cells, monkey cells, or guinea pig cells.

19. The multi-well plate of claim 1, wherein the compression step is accomplished by use of a clamp.

20. The multi-well plate of claim 1, wherein the gas plasma penetrates more than 10 cm along non-linear path in forming the micropatterned substrate.

21. The multi-well plate of claim 1, wherein the substrate to be micropatterned is not directly exposed to the oxygen plasma.

22. The multi-well plate of claim 1, wherein the period of time sufficient to ablate the exposed surfaces of the substrate while preserving activity of the biomolecules is from about 5 to about 1000 seconds.

23. The multi-well plate of claim 1, wherein the period of time sufficient to ablate the exposed surfaces of the substrate while preserving activity of the biomolecules is from about 5 to about 120 seconds.

* * * * *